(12) United States Patent
Shaw et al.

(10) Patent No.: US 8,637,234 B2
(45) Date of Patent: Jan. 28, 2014

(54) MOLECULAR SCAFFOLDS FOR HIV-1 EPITOPES

(75) Inventors: George M. Shaw, Birmingham, AL (US); James E. Robinson, New Orleans, LA (US); Frederic Bibollet-Ruche, Birmingham, AL (US); Julie M. Decker, Alabaster, AL (US); Beatrice H. Hahn, Birmingham, AL (US); Peter D. Kwong, Bethesda, MD (US)

(73) Assignees: UAB Research Foundation, Birmingham, AL (US); The Administrators of Tulane Educational Fund, New Orleans, LA (US); The United States of America, as represented by the Secretary, Department of Health and Human Services, Washington, DC (US)

( * ) Notice: Subject to any disclaimer, the term of this patent is extended or adjusted under 35 U.S.C. 154(b) by 870 days.

(21) Appl. No.: 11/578,761

(22) PCT Filed: Apr. 8, 2005

(86) PCT No.: PCT/US2005/011928
§ 371 (c)(1),
(2), (4) Date: Oct. 19, 2007

(87) PCT Pub. No.: WO2005/111621
PCT Pub. Date: Nov. 24, 2005

(65) Prior Publication Data

US 2008/0096187 A1 Apr. 24, 2008

Related U.S. Application Data

(60) Provisional application No. 60/649,551, filed on Feb. 3, 2005, provisional application No. 60/606,053, filed on Aug. 31, 2004, provisional application No. 60/562,824, filed on Apr. 16, 2004.

(51) Int. Cl.

| | |
|---|---|
| *C12Q 1/70* | (2006.01) |
| *A61K 39/00* | (2006.01) |
| *A61K 39/12* | (2006.01) |
| *A61K 39/21* | (2006.01) |
| *A61K 39/38* | (2006.01) |
| *C07K 16/00* | (2006.01) |

(52) U.S. Cl.
USPC ......... 435/5; 435/339; 435/339.1; 530/388.3; 530/388.35; 424/184.1; 424/185.1; 424/186.1; 424/187.1; 424/188.1

(58) Field of Classification Search
None
See application file for complete search history.

(56) References Cited

U.S. PATENT DOCUMENTS 5,912,176 A 6/1999 Wang et al.
6,328,973 B1 12/2001 Devico et al.

FOREIGN PATENT DOCUMENTS

WO WO 03/033666 A2 4/2003

OTHER PUBLICATIONS

Shibata, et al. Generation of a Chimeric Human and Simian Immunodeficiency Virus Infectious to Monkey Peripheral Blood Mononuclear Cells. J. Virol. 1991; 65(7):3514-3520.*

(Continued)

*Primary Examiner* — Jeffrey Stucker
*Assistant Examiner* — Stuart W Snyder

(57) ABSTRACT

Methods and compositions are provided for the use of an envelope polypeptide or a functional variant thereof from a lentivirus that is not HIV-1 as a molecular scaffold for HIV-1 epitopes. The HIV-1 epitopes can be recognized by HIV-1 binding antibodies, HIV-1 neutralizing antibodies and/or CD4-induced antibodies. Thus, methods are provided for detecting HIV-1 binding antibodies in a subject infected with HTV-1. Further provided are methods to determine an epitope for an HIV-1 binding antibody; methods to assay for an HIV-1 binding antibody; methods to identify a soluble CD4 mimic; methods to neutralize an non-HIV-1 virus; diagnostic assays to monitor HIV disease in a subject or to monitor the subject's response to immunization by a HIV vaccine; and methods to alter the neutralization potential of an HIV-1 derived CD4-induced antibody. Chimeric polypeptides, chimeric polynucleotides, kits, cells and viruses are also provided.

13 Claims, 17 Drawing Sheets

(56) References Cited

OTHER PUBLICATIONS

Robert-Guroff, et al. Cross-Neutralization of Human Immunodeficiency Virus Type 1 and 2 and Simian Immunodeficiency Virus Isolates. J. Virol. 1992; 66(6):3602-3608.*

Nyambi, et al. Study of the Dynamics of Neutralization Escape Mutants in a Chimpanzee Naturally Infected with the Simian Immunodeficiency Virus SIVcpz-ant. J. Virol. 1997; 71(3):2320-2330.*

DeVico, et al. Monoclonal antibodies raised against covalently cross linked complexes of human immunodeficiency virus type 1 gp120 and CD4 receptor identify a novel complex-dependent epitope on gp120. Virology. Aug. 20, 1995; 211(2):583-8.*

Wain-Hobson, S. The HIV-quasispecies: a necessary description. Int Conf AIDS. Jun. 4-9, 1989; 5: 524 (abstract No. W.C.O.4).*

Ecker, et al. Overexpression and Purification of a Recombinant Chimeric HIV Type 2/HIV Type 1 Envelope Peptide and Application in an Accelerated Immunobased HIV Type 1/2 Antibody Detection System (AIBS): A New Rapid Serological Screening Assay. AIDS Research and Human Retroviruses. 1996; 12(12):1081-1091.*

Liao, et al. Induction of high level of specific antibody response to the neutralizing epitope ELDKWA on HIV-1 gp41 by peptide-vaccine. Peptides 21 (2000) 463-468.*

Breuer, J., et al., "Human Immunodeficiency Virus Type 2 (HIV-2) *env* Gene Analysis: Prediction of Glycoprotein Epitopes Important for Heterotypic Neutralization and Evidence for Three Genotype Clusters within the HIV-2a Subtype" (1995) *Journal of General Virology*, vol. 76, pp. 333-345.

* cited by examiner

FIG. 4A

FROM FIG. 4A

```
                                                          V3                319
7312A     FNGTRAENRTYMYWHS---KDNRTIISLNKYYNLTIHCKRPGNKTVVPTTLMSGLVFHSQP
UC1       FNGTRTENRTYMYWHS---KDNRTIISLNKYYNLTMHCRRPGNKTVIPITIMSGLNFHSQP
MAC239    FNGTRTENRTYIYWHG---RDNRTIISLNKYYNLTMKCRRPGNKTVLPVTIMSGLVFHSQP
VER-TY01   LNGSYHENRTQIWQKHRVNNNTVLILFNKHYNLSVTCRRPGNKTVLPVTIMAGLVFHSQK
YU2       LNGSLAEEEIVIRSEN-FTNNAKTIIVQLNESVVINCTRPNNNTRKSINI--GPGRALYT
HXB2      LNGSLAEEEVVIRSVN-FTDNAKTIIVQLNTSVEINCTRPNNNTRKRIRIQRGPGRAFVT
          *  *    *  *            ***    *        *  *         *

7312A     IN----KRPRQAWCWFKG-EWREAMQEVKQTLIKHP---RYKGTNDTRNITFTKPGTGSDPE
UC1       LN----TRPRQAWCWFKG-NWIEAIREVKETIIKHP---RYKGTNNTERIRLVGPSAGSDPE
MAC239    IN----DRPKQAWCWFGG-KWKDAIKEVKQTIVKHP---RYTGTNNTDKINLTAPGGG-DPE
VER-TY01   YN----MKLRQAWCHFEG-NWRGAWREVKQKIVELPKDRYKGTNNTEHIYLQRQW-G-DPE
YU2       TGEIIGDIRQAHCNLSKTQWENTLEQIAIKLKEQF----GNNKTIIFN---PSSGGDPE
HXB2      IG-KIGNMRQAHCNISRAKWNNTLKQIASKLREQF----GNNKTIIFK---QSSGGDPE
                  **      *         *          *  ***

V4                   419  422
7312A     VAYMWTNCRGEFLYCNMTWFLNMWVENRTG-----QTQHNYAPCHIKQ
UC1       VRHMWTNCRGEFFYCNMTWFLNMWVENRTG-----TTQKNYVTCHIKQ
MAC239    VTFMWTNCRGEFLYCKMNWFLNWVEDRNTANQKPKE-QHKRNYVPCHIRQ
VER-TY01   ASNLWFNCQGEFFYCKMDWFLNYLNNKTWDADHNFCSSKKKGHAPGPCVQRTYVACHIRS
YU2       IVTHSFNCGGEFFYCNSTQLFTWNDTRKLNN-----TGRNITLPCRIKQ
HXB2      IVTHSFNCGGEFFYCNSTQLFNSTWFNSTWSTEGSNNTE-GSDTITLPCRIKQ
          *  **  *   *                                  *   *

482
7312A     LPPREGQLTCNSTVTSLIANIDVDVGNN--RTNITFSAEVAELYRLE
UC1       LPPREGTLSCNSSVTSLIANIDVYYDGNDTKTNITMSAEVGELYRLE
MAC239    LPPREGDLTCNSTVTSLIANIDWIDGNQ---TNITMSAEVAELYRLE
VER-TY01   APPREGHLQCRSTVTGMTVELVNYNSKNR----TNVTLSPQIESIWAAE
YU2       TAPPREGKAMTAPPIRGQIRCSSNITGLLLTRDGGKDTNGTEIFRPGGGDMRDNWRSE
HXB2      TAPPISGQIRCSSNITGLLLTRDGGNSNNESEIFRPGGGDMRDNWRSE
          *  * *                                    *

510
7312A     LGDYKLIEVTPIGFAPTSEKRYSS-TPGRHKR
UC1       LGDYKLIEITPIGFAPTEIKRYSS-TTPRNKR
MAC239    LGDYKLVEITPIGLAPTDVKRYTTGGTSRNKR
VER-TY01   LGRYKLVEITPIGFAPTEVRRYTG-GHERQKR
YU2       LYKYKVVKIEPLGVAPTKAKRRVV----QREKR
HXB2      LYKYKVVKIEPLGVAPTKAKRRVV----QREKR
          *  *  *  *  * ***
```

SEQUENCE IDENTITY
▨ BRIDGING SHEET 17/31 (55%)
○ CHEMOKING RECEPTOR 8/16 (50%)
△ CD4 BINDING SITE 7/26 (27%)
* OVERALL gp120 111/451 (25%)

HIV-2 Alignments with Bridging Sheet, Variable Loops, and AA434 Indicated

```
7312A     ---------MCGKNLLFVASLLASAY--LIYCTKYVTVFYGVPVWRNASIPLFCATKN--
UC1       --------MAHTSNHLFILLLLISVYGFLGHKKNYVTVFYGIPAWRNATVPLFCATTN--
UC2       --------MEPGRNQLLAVILLTSAC--LIYCKQYVTVFYGVPVWRNASIPLFCATKN--
ROD-B.14  -----------MMNQLLIAILLLASAC--LVYCTQYVTVFYGVPTWKNATIPLFCATRN--
HXB2      MRVKEKYQHLWRWGWRWGTMLLGMLMICSATEKLWVTVYYGVPVWKEATTTLFCASDAKA
                      **       . :***:**:*.:**. .****:

7312A     -----RDTWGTIQCLPDNDDYQEIALN-VTEAFDAWNNTVTEQAVEDVWSLFETSIKPCV
UC1       -----RDTWGTVQCLPDNGDYTEISVN-ITEAFDAWNNTVTEQAVDDVWSLFETSIKPCV
UC2       -----RDTWGTIQCLPDNDDYQEIPLN-VTEAFDAWDNTVTEQAIEDVWRLFETSIKPCV
ROD-B.14  -----RDTWGTIQCLPDNDDYQEITLN-VTEAFDAWNNTVTEQAIEDVWHLFETSIKPCV
HXB2      YDTEVHNVWATHACVPTDPNPQEVVLVNVTENFNMWKNDMVEQMHEDIISLWDQSLKPCV
                ::.*.*  *:*  : : *:  :    :** *:  *.* .** :*: *:: *:****
                                                              V1/V2

7312A     KLTPLCVAMSCNSTTATTTPPSSTTNNTTTTEPTTGG--PEINETFPCMRTDNCTGLGEEE
UC1       KLTPLCVAMRCN----NTGTNTTTKPITTPITTTKPSENLLNDTSPCIKNDTCPGIGLEN
UC2       KLTPLCVAMNCNPVTGNN-TNATAKPTAARPTTNPSYLTIINESSTCVGADNCTGLGDEG
ROD-B.14  KLTPLCVAMKCSSTESSIGNNTTSKSTSTTTTTPTDQEQEISEDTPCARADNCSGLGKEE
HXB2      KLTPLCVSLKCTDLKNDTNTNSSSGRMIMEK----------------------------GE
          *******:: *.                                            :::
                        V1/V2 (cont'd)

7312A     MVDCQFNMTGLERDKTKQYSETWYSKDVVCESNNASDGRDRCYMNHCMTSVITESCDKHY
UC1       TVDCYFNMTGLRRDEKKQYKDTWYEKDLECNGNSTS---TICYMRTCNTSVIQESCDKHY
UC2       MVNCKFNMTGLEQDKIKGYTDTWYSDDVVCDSTNKTGTNTTCYMRHCMTSVIKESCDKHY
ROD-B.14  TINCQFNMTGLERDKKKQYNETWYSKDVVCKTNNST-NQTQCYMNHCNTSVITESCDKHY
HXB2      IKNCSFNISTSIRGKVQKEYAFFYKLDIIPIDNDTT----SYKLTSCNTSVITQACPKVS
           :* **::   :.. :      :    *.   *:   ..  : :  ****** ::* *

7312A     WDAIRFRYCAPPGFALLRCNDTNYSGFMPNCSKVVVSSCTRMMETQTSTWFGFNGTRAEN
UC1       WDSLRFRYCAPPGYALLRCNDTNYSGFMPKCSKVVVSSCTRMMETQTSTWFGFNGTRTEN
UC2       WDSMKFRYCTPPGYALLRCNDTNYSGFAPNCPKVVAASCTRMMETQTSTWFGFNGTRAEN
ROD-B.14  WDAIRFRYCAPPGYALLRCNDTNYSGFAPNCSKVVASTCTRMMETQTSTWFGFNGTRAEN
HXB2      FEPIPIHYCAPAGFAILKCNNKTFNGTGP-CTNVSTVQCTHGIRPVVSTQLLLNGSLAEE
          ::.:   ::**:*.*:*:**;:*:**;...* *  *.:*  **:*.. .** . :**: :*:
                                                V3

7312A     RTYMYWHSK-DNRTIISLNKYYNLTIHCKRPGNKTVVPITLMSGLVFHSQ--PINKRPRQ
UC1       RTYMYWHSK-DNRTIISLNKYYNLTMHCRRPGNKTVIPITIMSGLNFHSQ--PLNTRPRQ
UC2       RTYIYWHGR-DNRTIISLNKHYNLTMHCKRPGNKTVVPITLMSGHRFHSQ-AVINKKPRQ
ROD-B.14  RTYIYWHGR-DNRTIISLNKYYNLSLHCKRPGNKTVKQIMLMSGHVFHSYKPINKRPRQ
HXB2      EVVIRSVNFTDNAKTIIVQLNTSVEINCTRPNNNTRKRIRIQRGPGRAFVTIGKIGNMRQ
          ..:    .   **  .*   :: .:   .:  **.*:*   *:  *     .    **

7312A     AWCWFK-GEWREAMQEVKQTLIKHPRYKGTNDTRNITFTKPGTGSDPEVAYMWTNCRGEF
UC1       AWCWFK-GNWIEAIREVKETIIKHPRYKGTNNTERIRLVGPSAGSDPEVRHMWTNCRGEF
UC2       AWCWFK-GNWKGAMQEVKQTLAGHPRYKGTNDTSKINFVKPGVGSDPEVTYMWTNCRGEF
ROD-B.14  AWCWFK-GKWKDAMQEVKETLAKHPRYRGTNDTRNISFAAPGKGSDPEVAYMWTNCRGEF
HXB2      AHCNISRAKWNNTLKQIASKLREQFGNN------KTIIFKQSSGGDPEIVTHSFNCGGEF
          * * :.  :*  ::::: ..:  .       . : . *.***:    ** ***
```

FROM FIG. 7A

```
                                                        V4                                  434
7312A      LYCNMTWFLN----------WVENRTGQTQHNYAPCHIKQIINTWHKVGKNVYLPPREGQ
UC1        FYCNMTWFLN----------WVENRTGTTQKNYVTCHIKQIVNTWHKVGKYVYLPPREGT
UC2        FYCNMTWFLN----------WVENRTSQKQRNYAPCHIRQIINTWHKVGQIVYLPPREGE
ROD-B.14   FYCNMTWFLN----------WIENKT---HRNYAPCHIRQIINTWHKVGINVYLPPREGE
HXB2       FYCNSTQLFNSTWFNSTWSTEGSNNTEGSDTITLPCRIKQIINMWQKVGKAMYAPPISGQ
           :***  *  ::*          .*.*    .  .*:*:**:* *:*** :*  ** .*

7312A      LTCNSTVTSLIANIDVD--VGNNRTNITFSAEVAELYRLELGDYKLIEVTPIGFAPTSEK
UC1        LSCNSSVTSLIANIDVYYDGNDTKTNITMSAEVGELYRLELGDYKLVEITPIGFAPTEIK
UC2        LTCNSTVTSIIANIDT---DGN-QTNITFSAEVAELYRLELGDYKLIEITPIGFAPTSEK
ROD-B.14   LSCNSTVTSIIANIDW---QNNNQTNITFSAEVAELYRLELGDYKLVEITPIGFAPTKEK
HXB2       IRCSSNITGLLLTRDGGNSNNESEIFRPGGGDMRDNWRSELYKYKVVKIEPLGVAPTKAK
           : *.*.:*.::  . *    .:   . ...:: : :* **  .**:::: *:*.***. *

7312A      RYSSTPGRHKRGVFVLGFLGFLTTAGAAMGAASLTLSAQSRTLLAGIVQQQQQLLDVVKR
UC1        RYSSTTPRNKRGVMVLGFLGLLAMAGSAMGATSLTLSAQSRTLLAGIVQQQQQLLDVVKR
UC2        RYSSAPARNKRGVFVLGLLGFLATAGSAMGAASLTLSAQSRTLLAGIVQQQQQLLDIVKR
ROD-B.14   RYSSAHGRHTRGVFVLGFLGFLATAGSAMGAASLTLSAQSRTLLTGIVQQQQQLLDVVKR
HXB2       RRVVQREKRAVGIGAL-FLGFLGAAGSTMGAASMTLTVQARQLLSGIVQQQNNLLRAIEA
           *        :. *: .* :**:*  **::***:*:**.*:* **:*****::: ::

7312A      QQEMLRLTVWGTKNLQARVTAIEKYLKDQAQLNSWGCAFRQVCHTTVPW----VNDSLTP
UC1        QQELLRLTVWGTKNLQTRVTAIEKYLKDQALLNSWGCAFRQVCHTTVPW----PNETLTP
UC2        QQELLRLTVWGTKNLQARVTAIEKYLKDQAQLNSWGCTFRQVCHTTVPW----VNDSLTP
ROD-B.14   QQELLRLTVWGTKNLQARVTAIEKYLQDQARLNSWGCAFRQVCHTTVPW----VNDSLAP
HXB2       QQHLQLTVWGIKQLQARILAVERYLKDQQLLGIWGCSGKLICTTAVPWNASWSNKSLEQ
           **.:*:****** *:**:**  *:*:**:**  *,  ***  : :*  *:***    *.:*

7312A      DWDNMTWQQWEKQIRDLEANISESLEQAQIQQEKNMYELQKLNSWDVFGNWFDLASWVKY
UC1        DWENMTWQQWEKRVNFLDANITALLEEAQIQQERNMYELQKLNSWDVFGNWFDFTSWMAY
UC2        RWNNMTWQEWEKQVRYLEANISQSLEEAQIQQEKNMYELQKLNSWDVFGNWFDLTSWIKY
ROD-B.14   DWDNMTWQEWEKQVRYLEANISKSLEQAQIQQEKNMYELQKLNSWDIFGNWFDLTSWVKY
HXB2       IWNHTTWMEWDREINNYTSLIHSLIEESQNQQEKNEQELLELDKWASLWNWFNITNWLWY
           *:: ** :*::..,.   : *  :*:::* ***:*  **  :*:.*   : ***:::.*: *

7312A      IQYGVYIVVGIVALRVIIYVVQMIGRLRRGYRPVFSSPPGYFQQIRIHKDQEQPANEETE
UC1        IRLGLYVVAGLIVLRIVIYIMQMLARLRKGYRPVFSSPPSYTQQIPIRKHRGQPANEETE
UC2        IQYGVYIVVGIIALRIAIYVVQLLSRFRKGYRPVFSSPPGYLQQIHIHTDRGQPANEETE
ROD-B.14   IQYGVLIIVAVIALRIVIYVVQMLSRLRKGYRPVFSSPPGYIQQIHIHKDRGQPANEETE
HXB2       IKLFIMIVGGLVGLRIVFAVLSIVNRVRQGYSPLS-------FQTHLPTPRGPDRPGIE
           *: : :: .:: **:  :  .:: *.:*** *:       *  :.:   *  *

7312A      EGGGNDGGYRSWPWQIEYIHFLIRQLRNLLIWLYDGCRTLLLKT-------FQTLQPALQ
UC1        DEGGNEGAYRSWPWQIEYAHFLIRQLRNLLIWLYNGCRNLLLKT-------SQILQPALQ
UC2        GDAGDASGYDFWPWPINYIQLLIHLLTRLLTGLYSICRDLLSANSPTRRLISQNLTAIRD
ROD-B.14   EDGGSNGGDRYWP------------------------------------------------
HXB2       EEGGERDRDRSIRLVNGSLALIWDDLRSLCLFSYHRLRDLLLIVTR----IVELLGRRGWE
                                                   .*. .

7312A      PLRLLFAYLQYGIGWFQEAVQAAAGATGETLASTGRTLWEALRRTARGIIAVPRRIRQGL
UC1        PLRLSLAYLQYGISWFQEAIQAATRAARETLANTGRALWKALRRTAEAIIAIPRRIRQGL
UC2        WLRLKAAYLQYGCEWIQEAFQAIARTARETLAGAWRGLCKAVQRIGRGILAVPRRIRQGA
ROD-B.14   -------------------------------------------------------------
HXB2       ALKYWWNLLQYWSQELKNSAVSLLNATAIAVAEGTDRVIEVVQGACRAIRHIPRRIRQGL

7312A      ELALL
UC1        ELALL
UC2        EIALL                        FIG. 7B
ROD-B.14   -----
HXB2       ERILL
```

```
                                                                                                569
ST        KRGVFVLG-FLGFLTTAGAAMGAASLTLSAQSRTLLAGIVQQQQQLLDVVKRQQEMLRLT
7312A     KRGVFVLG-FLGFLTTAGAAMGAASLTLSAQSRTLLAGIVQQQQQLLDVVKRQQEMLRLT
UC1       KRGVMVLG-FLGLLAMAGSAMGATASLTLSAQSRTLLAGIVQQQQQLLDVVKRQQELLRLT
YU-2      KRAVGLGALFLGFLGAAGSTMGAASITLTVQARQLLSGIVQQQNNLLRAIEAQQHLLQLT
HXB-2c    KRAVGIALFLGFLGAAGSTMGAASMTLTVQARQLLSGIVQQQNNLLRAIEAQQHLLQLT
          ***.*  . ****::* *:****:*:. ***:*:******** ** *:.*****:*:*

629
ST        VWGTKNLQARVTAIEKYLKDQAQLNSWGCAFRQVCHTTVPW----VNDTLTPDWNNMTWQ
7312A     VWGTKNLQARVTAIEKYLKDQAQLNSWGCAFRQVCHTTVPW----VNDSLTPDWDNMTWQ
UC1       VWGTKNLQTRVTAIEKYLKDQALLNSWGCAFRQVCHTTVPW----PNETLTPDWENMTWQ
YU-2      VWGIKQLQARVLAVERYLRDQQLLGIWGCSGKLICTTTVPWNTSWSNKSLNEIWDNMTWM
HXB-2c    VWGIKQLQARILAVERYLKDQQLLGIWGCSGKLICTTAVPWNASWSNKSLEQIWNHTTWM
          *** *:**:*: *:****:**  * *** .: :* **:***    .*  :    : **

689
ST        EWEQRIRNLEANISESLEQAQIQQEKNMYELQKLNSWDVFGNWFDLTSWIKYIQYGVYIV
7312A     QWEKQIRDLEANISESLEQAQIQQEKNMYELQKLNSWDVFGNWFDLASWVKYIQYGVYIV
UC1       QWEKRVNFLDANITALLEEAQIQQERNMYELQKLNSWDVFGNWFDFTSWMAYIRLGLYVV
YU-2      KWEREIDNYTHIIYSLIEQSNQQEKNEQELLALDKWASLWNWFDITKWLWYIKIFIMIV
HXB-2c    EWDREINNYTSLIHSLIEESNQQEKNEQELLELDKWASLWNWFNITNWLWYIKLFIMIV
          .*::     :  : *:*: .: ***:*  **  *.*:*  **** . * **:  : :*
```

FROM FIG. 8A

```
                                                                                                 742
ST       VGIIVLRIVIYVVQMLSRLRKGYRPVFSSPPAYFQQIHIHKDREQPAREETEEDVGNSVG
7312A    VGIVALRVIIYVVQMIGRLRRGYRPVFSSPPGYFQQIRIHKDQEQPANEETEEGGGNDGG
UC1      AGLIVLRIVIYIMQMLARLRKGYRPVFSSPPSYTQQIPIRKHRGQPANEETEDEGGNEGA
YU-2     GGLIGLRIVFVVLSIVNRVRQGY------SPLSFQTHLPAQRGPDRP---DGIEEEGGERDR
HXB-2c   GGLVGLRIVFAVLSIVNRVRQGY------SPLSFQTHLPTPRGPDRP---EGIEEEGGERDR
         .*.: .**::.: ::*.:: *:*:.**     **  .    ::   .     *: .*:*****
                                                                                                 795
ST       DNWWPWPIRYIHFLIRQLIRLLNRLYNICRDLLSRSFQTLQLISQSLRRALTAVRDWLRF
7312A    YRSWPWQIEYIHFLIRQLIRQLRNLLIWLYDGCRTLLLKTFQTLQPALQPLR--------LLF
UC1      YRSWPWQIEYAHFLIRQLRNLLIWLYNGCRNLLLKTSQILQPALQPLR--------------L
YU-2     DRSGPLVDGFLAIIWDLRSLCLFSYHRLRDLLIVTRIVELLGRRGWG--------------VLKY
HXB-2c   DRSIRLVNGSLALIWDDLRSLCLFSYHRLRDLLLIVTRIVELLGRRGWE--------------ALKY
         .:   :  .  * *  * * *       *. * .  **    ** *
                                                                                                 855
ST       NTAYLQYGGEWIQEAFRAFARATGETTLTNAWRGFWGTLGQIGRGILAVPRRIRQGAEIAL
7312A    --AYLQYGIGWFQEAVQAAAAGATGETLASTGRTLWEALRRTARGIIAVPRRIRQGLEAL
UC1      SLAYLQYGISWFQEAIQAATRAARETLANTGRAIWKALRRTAEAIIAIPRRIRQGLELAL
YU-2     WWNLLQYWIQELKNSAVSLLNATAIAVAEGTDRVIEILQRAFRAVLHIPVRIRQGLERAL
HXB-2c   WWNLLQYWSQELKNSAVSLLNATAIAVAEGTDRVIEVVQGACRAIRHIPRRIRQGLERIL
         . :   *   * :    .:  : :    ::  .       *  ::* *****  *
ST       L
7312A    L
UC1      L
YU-2     L
HXB-2c   L
         *
```

FIG. 8B

```
              647                                                      687
7312A     ...QIQQEKNMYELQKLNSWDVFGNWFDLASWVKYIQYGVYIV...
7312A-C1  ...QIQQEKNMYELLALDKWASLWNWFDITKWLWYIKYGVYIV...
7312A-C2  ...QIQQEKNMYELQALDKWASLWNWFDITKWLWYIKYGVYIV...
7312A-C3  ...QIQQEKNMYELLALDKWASLMNWFDLASWVKYIQYGVYIV...
7312A-C4  ...QIQQEKNMYELQKLNSWDVFGNWFDITKWLWYIKYGVYIV...
7312A-C5  ...QIQQEKNMYELQKLNSWDVFGNWFDITSWVKYIQYGVYIV...
7312A-C6  ...QIQQEKNMYELQALDKWAVFGNWFDLASWVKYIQYGVYIV...
```

Fig. 11

SEQUENCE LISTING

```
<160> NUMBER OF SEQ ID NOS: 39

<210> SEQ ID NO 1
<211> LENGTH: 365
<212> TYPE: PRT
<213> ORGANISM: Homo sapiens

<400> SEQUENCE: 1

Lys Lys Val Val Leu Gly Lys Lys Gly Asp Thr Val Glu Leu Thr Cys
 1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
```

```
                35                  40                  45
Ser Lys Leu Asn Asp Arg Ala Asp Ser Arg Ser Leu Trp Asp Gln
 50                  55                  60

Gly Asn Phe Pro Leu Ile Ile Lys Asn Leu Lys Ile Glu Asp Ser Asp
 65                  70                  75                  80

Thr Tyr Ile Cys Glu Val Asp Gln Lys Glu Val Gln Leu Leu
                 85                  90                  95

Val Phe Gly Leu Thr Ala Asn Ser Asp Thr His Leu Leu Gln Gly Gln
                100                 105                 110

Ser Leu Thr Leu Thr Leu Glu Ser Pro Pro Gly Ser Ser Pro Ser Val
                115                 120                 125

Gln Cys Arg Ser Pro Arg Gly Lys Asn Ile Gln Gly Gly Lys Thr Leu
                130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Val Tyr Lys Lys Glu Gly Glu
                180                 185                 190

Gln Val Glu Phe Ser Phe Pro Leu Ala Phe Thr Val Glu Lys Leu Thr
                195                 200                 205

Gly Ser Gly Glu Leu Trp Trp Gln Ala Glu Arg Ala Ser Ser Ser Lys
                210                 215                 220

Ser Trp Ile Thr Phe Asp Leu Lys Asn Lys Glu Val Ser Val Lys Arg
225                 230                 235                 240

Val Thr Gln Asp Pro Lys Leu Gln Met Gly Lys Lys Leu Pro Leu His
                245                 250                 255

Leu Thr Leu Pro Gln Ala Leu Pro Gln Tyr Ala Gly Ser Gly Asn Leu
                260                 265                 270

Thr Leu Ala Leu Glu Ala Lys Thr Gly Lys Leu His Gln Glu Val Asn
                275                 280                 285

Leu Val Val Met Arg Ala Thr Gln Leu Gln Lys Asn Leu Thr Cys Glu
                290                 295                 300

Val Trp Gly Pro Thr Ser Pro Lys Leu Met Leu Ser Leu Lys Leu Glu
305                 310                 315                 320

Asn Lys Glu Ala Lys Val Ser Lys Arg Glu Lys Ala Val Trp Val Leu
                325                 330                 335

Asn Pro Glu Ala Gly Met Trp Gln Cys Leu Leu Ser Asp Ser Gly Gln
                340                 345                 350

Val Leu Leu Glu Ser Asn Ile Lys Val Leu Pro Thr Trp
                355                 360                 365

<210> SEQ ID NO 2
<211> LENGTH: 857
<212> TYPE: PRT
<213> ORGANISM: Human immunodeficiency type 2 7312A isolate

<400> SEQUENCE: 2

Met Cys Gly Lys Asn Leu Leu Phe Val Ala Ser Leu Leu Ala Ser Ala
 1               5                  10                  15

Tyr Leu Ile Tyr Cys Thr Lys Tyr Val Thr Val Phe Tyr Gly Val Pro
                20                  25                  30

Val Trp Arg Asn Ala Ser Ile Pro Leu Phe Cys Ala Thr Lys Asn Arg
                35                  40                  45

Asp Thr Trp Gly Thr Ile Gln Cys Leu Pro Asp Asn Asp Asp Tyr Gln
```

```
            50                  55                  60
Glu Ile Ala Leu Asn Val Thr Glu Ala Phe Asp Ala Trp Asn Asn Thr
65                  70                  75                  80

Val Thr Glu Gln Ala Val Glu Asp Val Trp Ser Leu Phe Glu Thr Ser
                85                  90                  95

Ile Lys Pro Cys Val Lys Leu Thr Pro Leu Cys Val Ala Met Ser Cys
            100                 105                 110

Asn Ser Thr Thr Ala Thr Thr Thr Pro Ser Thr Thr Asn Asn Thr
            115                 120                 125

Thr Thr Thr Glu Pro Thr Thr Gly Gly Pro Glu Ile Asn Glu Thr Phe
130                 135                 140

Pro Cys Met Arg Thr Asp Asn Cys Thr Gly Leu Gly Glu Glu Glu Met
145                 150                 155                 160

Val Asp Cys Gln Phe Asn Met Thr Gly Leu Glu Arg Asp Lys Thr Lys
                165                 170                 175

Gln Tyr Ser Glu Thr Trp Tyr Ser Lys Asp Val Val Cys Glu Ser Asn
            180                 185                 190

Asn Ala Ser Asp Gly Arg Asp Arg Cys Tyr Met Asn His Cys Asn Thr
            195                 200                 205

Ser Val Ile Thr Glu Ser Cys Asp Lys His Tyr Trp Asp Ala Ile Arg
210                 215                 220

Phe Arg Tyr Cys Ala Pro Pro Gly Phe Ala Leu Leu Arg Cys Asn Asp
225                 230                 235                 240

Thr Asn Tyr Ser Gly Phe Met Pro Asn Cys Ser Lys Val Val Ser
                245                 250                 255

Ser Cys Thr Arg Met Met Glu Thr Gln Thr Ser Thr Trp Phe Gly Phe
            260                 265                 270

Asn Gly Thr Arg Ala Glu Asn Arg Thr Tyr Met Tyr Trp His Ser Lys
            275                 280                 285

Asp Asn Arg Thr Ile Ile Ser Leu Asn Lys Tyr Tyr Asn Leu Thr Ile
290                 295                 300

His Cys Lys Arg Pro Gly Asn Lys Thr Val Val Pro Ile Thr Leu Met
305                 310                 315                 320

Ser Gly Leu Val Phe His Ser Gln Pro Ile Asn Lys Arg Pro Arg Gln
                325                 330                 335

Ala Trp Cys Trp Phe Lys Gly Glu Trp Arg Glu Ala Met Gln Glu Val
            340                 345                 350

Lys Gln Thr Leu Ile Lys His Pro Arg Tyr Lys Gly Thr Asn Asp Thr
            355                 360                 365

Arg Asn Ile Thr Phe Thr Lys Pro Gly Thr Gly Ser Asp Pro Glu Val
370                 375                 380

Ala Tyr Met Trp Thr Asn Cys Arg Gly Glu Phe Leu Tyr Cys Asn Met
385                 390                 395                 400

Thr Trp Phe Leu Asn Trp Val Glu Asn Arg Thr Gly Gln Thr Gln His
                405                 410                 415

Asn Tyr Ala Pro Cys His Ile Lys Gln Ile Ile Asn Thr Trp His Lys
            420                 425                 430

Val Gly Lys Asn Val Tyr Leu Pro Pro Arg Glu Gly Gln Leu Thr Cys
            435                 440                 445

Asn Ser Thr Val Thr Ser Leu Ile Ala Asn Ile Asp Val Asp Val Gly
            450                 455                 460

Asn Asn Arg Thr Asn Ile Thr Phe Ser Ala Glu Val Ala Glu Leu Tyr
465                 470                 475                 480
```

```
Arg Leu Glu Leu Gly Asp Tyr Lys Leu Ile Glu Val Thr Pro Ile Gly
            485                 490                 495

Phe Ala Pro Thr Ser Glu Lys Arg Tyr Ser Ser Thr Pro Gly Arg His
        500                 505                 510

Lys Arg Gly Val Phe Val Leu Gly Phe Leu Gly Phe Leu Thr Thr Ala
    515                 520                 525

Gly Ala Ala Met Gly Ala Ala Ser Leu Thr Leu Ser Ala Gln Ser Arg
530                 535                 540

Thr Leu Leu Ala Gly Ile Val Gln Gln Gln Gln Gln Leu Leu Asp Val
545                 550                 555                 560

Val Lys Arg Gln Gln Glu Met Leu Arg Leu Thr Val Trp Gly Thr Lys
                565                 570                 575

Asn Leu Gln Ala Arg Val Thr Ala Ile Glu Lys Tyr Leu Lys Asp Gln
            580                 585                 590

Ala Gln Leu Asn Ser Trp Gly Cys Ala Phe Arg Gln Val Cys His Thr
        595                 600                 605

Thr Val Pro Trp Val Asn Asp Ser Leu Thr Pro Asp Trp Asp Asn Met
    610                 615                 620

Thr Trp Gln Gln Trp Glu Lys Gln Ile Arg Asp Leu Glu Ala Asn Ile
625                 630                 635                 640

Ser Glu Ser Leu Glu Gln Ala Gln Ile Gln Gln Glu Lys Asn Met Tyr
                645                 650                 655

Glu Leu Gln Lys Leu Asn Ser Trp Asp Val Phe Gly Asn Trp Phe Asp
            660                 665                 670

Leu Ala Ser Trp Val Lys Tyr Ile Gln Tyr Gly Val Tyr Ile Val Val
        675                 680                 685

Gly Ile Val Ala Leu Arg Val Ile Ile Tyr Val Val Gln Met Ile Gly
    690                 695                 700

Arg Leu Arg Arg Gly Tyr Arg Pro Val Phe Ser Ser Pro Pro Gly Tyr
705                 710                 715                 720

Phe Gln Gln Ile Arg Ile His Lys Asp Gln Glu Gln Pro Ala Asn Glu
                725                 730                 735

Glu Thr Glu Glu Gly Gly Gly Asn Asp Gly Gly Tyr Arg Ser Trp Pro
            740                 745                 750

Trp Gln Ile Glu Tyr Ile His Phe Leu Ile Arg Gln Leu Arg Asn Leu
        755                 760                 765

Leu Ile Trp Leu Tyr Asp Gly Cys Arg Thr Leu Leu Leu Lys Thr Phe
    770                 775                 780

Gln Thr Leu Gln Pro Ala Leu Gln Pro Leu Arg Leu Leu Phe Ala Tyr
785                 790                 795                 800

Leu Gln Tyr Gly Ile Gly Trp Phe Gln Glu Ala Val Gln Ala Ala Ala
                805                 810                 815

Gly Ala Thr Gly Glu Thr Leu Ala Ser Thr Gly Arg Thr Leu Trp Glu
            820                 825                 830

Ala Leu Arg Arg Thr Ala Arg Gly Ile Ile Ala Val Pro Arg Arg Ile
        835                 840                 845

Arg Gln Gly Leu Glu Leu Ala Leu Leu
    850                 855

<210> SEQ ID NO 3
<211> LENGTH: 779
<212> TYPE: PRT
<213> ORGANISM: Simian immunodeficiency virus SmPBJ1.9

<400> SEQUENCE: 3
```

```
Met Arg Cys Asn Lys Ser Glu Thr Asp Arg Trp Gly Leu Thr Gly Thr
1               5                   10                  15
Pro Ala Pro Thr Thr Thr Gln Thr Thr Thr Gln Ala Ser Thr Thr
            20                  25                  30
Pro Thr Ser Pro Ile Thr Ala Lys Val Val Asn Asp Ser Asp Pro Cys
            35                  40                  45
Ile Lys Ile Asn Asn Cys Thr Gly Leu Glu Gln Glu Pro Met Val Ser
50                  55                  60
Cys Lys Phe Asn Met Thr Gly Leu Lys Arg Asp Lys Lys Arg Glu Tyr
65                  70                  75                  80
Asn Glu Thr Trp Tyr Ser Arg Asp Leu Val Cys Glu Gln Asn Asn Asn
                85                  90                  95
Glu Thr Asp Ser Lys Cys Tyr Met Asn His Cys Asn Thr Ser Val Ile
                100                 105                 110
Gln Glu Ser Cys Asp Lys His Tyr Trp Asp Ala Ile Arg Phe Arg Tyr
                115                 120                 125
Cys Ala Pro Pro Gly Tyr Ala Leu Leu Arg Cys Asn Asp Ser Asn Tyr
130                 135                 140
Ser Gly Phe Ala Pro Asn Cys Thr Lys Val Val Val Thr Ser Cys Thr
145                 150                 155                 160
Arg Met Met Glu Thr Gln Thr Ser Thr Trp Phe Gly Phe Asn Gly Thr
                165                 170                 175
Arg Ala Glu Asn Arg Thr Tyr Ile Tyr Trp His Gly Arg Ser Asn Arg
                180                 185                 190
Thr Ile Ile Ser Leu Asn Lys Tyr Tyr Asn Leu Thr Met Arg Cys Arg
                195                 200                 205
Arg Pro Gly Asn Lys Thr Val Leu Pro Val Thr Ile Met Ser Gly Leu
210                 215                 220
Val Phe His Ser Gln Pro Ile Asn Glu Arg Pro Lys Gln Ala Trp Cys
225                 230                 235                 240
Trp Phe Gly Gly Glu Trp Lys Lys Ala Ile Gln Glu Val Lys Glu Thr
                245                 250                 255
Leu Val Lys His Pro Arg Tyr Thr Gly Thr Asn Lys Thr Glu Gln Ile
                260                 265                 270
Lys Leu Thr Ala Pro Gly Gly Gly Asp Pro Glu Val Thr Phe Met Trp
                275                 280                 285
Thr Asn Cys Arg Gly Glu Phe Leu Tyr Cys Lys Met Asn Trp Phe Leu
                290                 295                 300
Asn Trp Val Glu Glu Ile Gln Asn Gly Ser Arg Trp Thr Ser Gln Asn
305                 310                 315                 320
Gln Lys Glu Arg Gln Arg Arg Asn Tyr Val Pro Cys His Ile Arg Gln
                325                 330                 335
Ile Ile Asn Thr Trp His Lys Val Gly Lys Asn Val Tyr Leu Pro Pro
                340                 345                 350
Arg Glu Gly Asp Leu Thr Cys Asn Ser Thr Val Thr Ser Leu Ile Ala
                355                 360                 365
Glu Ile Asp Trp Ile Asn Gly Asn Glu Thr Asn Ile Thr Met Ser Ala
                370                 375                 380
Glu Val Ala Glu Leu Tyr Arg Leu Glu Leu Gly Asp Tyr Lys Leu Val
385                 390                 395                 400
Glu Ile Thr Pro Ile Ala Phe Ala Pro Thr Ser Val Lys Arg Tyr Thr
                405                 410                 415
Thr Thr Gly Ala Ser Arg Asn Lys Arg Gly Val Phe Val Leu Gly Phe
                420                 425                 430
```

```
Leu Gly Phe Leu Ala Thr Ala Gly Ser Ala Met Gly Ala Ala Ser Val
            435                 440                 445

Thr Leu Ser Ala Gln Ser Arg Thr Leu Leu Ala Gly Ile Val Gln Gln
    450                 455                 460

Gln Gln Gln Leu Leu Asp Val Val Lys Arg Gln Glu Leu Leu Arg
465                 470                 475                 480

Leu Thr Val Trp Gly Ala Lys Asn Leu Gln Thr Arg Val Thr Ala Ile
                485                 490                 495

Glu Lys Tyr Leu Lys Asp Gln Ala Gln Leu Asn Ser Trp Gly Cys Ala
                500                 505                 510

Phe Arg Gln Val Cys His Thr Thr Val Pro Trp Pro Asn Asp Thr Leu
            515                 520                 525

Thr Pro Asn Trp Asn Asn Met Thr Trp Gln Glu Trp Glu Lys Gln Val
    530                 535                 540

Asn Phe Leu Glu Ala Asn Ile Thr Gln Ser Leu Glu Glu Ala Gln Ile
545                 550                 555                 560

Gln Gln Glu Lys Asn Thr Tyr Glu Leu Gln Lys Leu Asn Ser Trp Asp
                565                 570                 575

Ile Phe Gly Asn Trp Phe Asp Leu Thr Ser Trp Ile Lys Tyr Ile Gln
                580                 585                 590

Tyr Gly Val Leu Ile Val Leu Gly Val Ile Gly Leu Arg Ile Val Ile
            595                 600                 605

Tyr Val Val Gln Met Leu Ala Arg Leu Arg Gln Gly Tyr Arg Pro Val
    610                 615                 620

Phe Ser Ser Pro Pro Ala Tyr Val Gln Gln Ile Pro Ile Gln Thr Gly
625                 630                 635                 640

Gln Glu Leu Pro Thr Lys Glu Gly Glu Gly Asp Gly Gly Arg
                645                 650                 655

Gly Gly Asn Arg Ser Trp Pro Trp Gln Ile Glu Tyr Ile His Phe Leu
                660                 665                 670

Ile Arg Gln Leu Ile Arg Leu Leu Thr Trp Leu Phe Ser Ser Cys Arg
            675                 680                 685

Asp Trp Leu Leu Arg Asn Cys Gln Thr Leu Gln Pro Val Leu Gln Ser
    690                 695                 700

Leu Ser Arg Thr Leu Gln Arg Ala Arg Glu Val Ile Arg Val Gln Ile
705                 710                 715                 720

Ala Tyr Leu Gln Tyr Gly Trp Arg Tyr Leu Gln Glu Ala Ala Gln Ala
                725                 730                 735

Trp Trp Lys Phe Val Arg Glu Thr Leu Ala Ser Ala Trp Arg Asp Leu
                740                 745                 750

Trp Glu Thr Leu Gly Arg Val Gly Arg Gly Ile Leu Ala Ile Pro Arg
            755                 760                 765

Arg Ile Arg Gln Gly Leu Glu Leu Thr Leu Leu
    770                 775

<210> SEQ ID NO 4
<211> LENGTH: 768
<212> TYPE: PRT
<213> ORGANISM: Simian immunodeficiency virus agmVer155

<400> SEQUENCE: 4

Met Thr Lys Phe Leu Gly Ile Phe Ile Val Leu Gly Ile Gly Ile Gly
1               5                   10                  15

Ile Gly Ile Ser Thr Lys Gln Gln Trp Ile Thr Val Phe Tyr Gly Val
                20                  25                  30
```

```
Pro Val Trp Lys Asn Ser Ser Val Gln Ala Phe Cys Met Thr Pro Thr
            35                  40                  45

Thr Arg Leu Trp Ala Thr Thr Asn Cys Ile Pro Asp Asp His Asp Tyr
     50                  55                  60

Thr Glu Val Pro Leu Asn Ile Thr Glu Pro Phe Glu Ala Trp Ala Asp
 65                  70                  75                  80

Arg Asn Pro Leu Val Ala Gln Ala Gly Ser Asn Ile His Leu Leu Phe
                 85                  90                  95

Glu Gln Thr Leu Lys Pro Cys Val Lys Leu Ser Pro Leu Cys Ile Lys
            100                 105                 110

Met Asn Cys Val Glu Leu Lys Gly Ser Ala Thr Ser Thr Pro Ala Thr
            115                 120                 125

Ser Thr Thr Ala Gly Thr Lys Leu Pro Cys Val Arg Asn Lys Thr Asp
            130                 135                 140

Ser Asn Leu Gln Ser Cys Asn Asp Thr Ile Ile Glu Lys Glu Met Asn
145                 150                 155                 160

Asp Glu Ala Ala Ser Asn Cys Thr Phe Ala Met Ala Gly Tyr Ile Arg
                165                 170                 175

Asp Gln Lys Lys Asn Tyr Ser Val Val Trp Asn Asp Ala Glu Ile Phe
            180                 185                 190

Cys Lys Arg Ser Thr Ser His Asn Gly Thr Lys Glu Cys Tyr Met Ile
            195                 200                 205

His Cys Asn Asp Ser Val Ile Lys Glu Ala Cys Asp Lys Thr Tyr Trp
            210                 215                 220

Asp Glu Leu Arg Leu Arg Tyr Cys Ala Pro Ala Gly Tyr Ala Leu Leu
225                 230                 235                 240

Lys Cys Asn Asp Trp Asp Tyr Ala Gly Phe Lys Pro Glu Cys Ser Asn
                245                 250                 255

Val Ser Val Val His Cys Thr Thr Leu Met Asn Thr Thr Val Thr Thr
            260                 265                 270

Gly Leu Leu Leu Asn Gly Ser Tyr Ser Glu Asn Arg Thr Gln Ile Trp
            275                 280                 285

Gln Lys His Gly Val Ser Asn Asp Ser Val Leu Ile Leu Leu Asn Lys
            290                 295                 300

His Tyr Asn Leu Thr Val Thr Cys Lys Arg Pro Gly Asn Lys Thr Val
305                 310                 315                 320

Leu Pro Val Thr Ile Met Ala Gly Leu Val Phe His Ser Gln Lys Tyr
                325                 330                 335

Asn Thr Arg Leu Arg Gln Ala Trp Cys His Phe Gln Gly Asn Trp Lys
            340                 345                 350

Gly Ala Trp Lys Glu Val Gln Glu Ile Val Lys Leu Pro Lys Glu
            355                 360                 365

Arg Tyr Gln Gly Thr Asn Asp Thr Asn Lys Ile Phe Leu Gln Arg Gln
     370                 375                 380

Phe Gly Asp Pro Glu Ala Ala Asn Leu Trp Phe Asn Cys Gln Gly Glu
385                 390                 395                 400

Phe Phe Tyr Cys Lys Met Asp Trp Phe Leu Asn Tyr Leu Asn Asn Leu
                405                 410                 415

Thr Val Asp Ala Asp His Asn His Cys Lys Asn Ala Gly Lys Gly
            420                 425                 430

Arg Ser Pro Gly Pro Cys Val Gln Arg Thr Tyr Val Ala Cys His Ile
            435                 440                 445

Arg Ser Val Ile Asn Asp Trp Tyr Thr Ile Ser Lys Lys Thr Tyr Ala
```

-continued

```
                450                 455                 460
Pro Pro Arg Glu Gly His Leu Gln Cys Thr Ser Thr Val Thr Gly Met
465                 470                 475                 480

Thr Val Glu Leu Asn Tyr Asn Asn Gln Asn Arg Thr Asn Val Thr Leu
                485                 490                 495

Ser Pro Gln Ile Glu Thr Ile Trp Ala Ala Glu Leu Gly Arg Tyr Lys
                500                 505                 510

Leu Val Glu Ile Thr Pro Ile Gly Phe Ala Pro Thr Glu Val Arg Arg
                515                 520                 525

Tyr Thr Gly Gly Gln Glu Arg Gln Lys Arg Val Pro Phe Val Leu Gly
                530                 535                 540

Phe Leu Gly Phe Leu Gly Ala Ala Gly Thr Ala Met Gly Ala Ala Ala
545                 550                 555                 560

Thr Ala Leu Thr Val Gln Ser Gln His Leu Leu Ala Gly Ile Leu Gln
                565                 570                 575

Gln Gln Lys Asn Leu Leu Ala Ala Val Gly Ala Gln Gln Gln Met Leu
                580                 585                 590

Lys Leu Thr Ile Trp Gly Val Lys Asn Leu Asn Ala Arg Val Thr Ala
                595                 600                 605

Leu Glu Lys Tyr Leu Ala Asp Gln Ala Arg Leu Asn Ala Trp Gly Cys
                610                 615                 620

Ala Trp Lys Gln Val Cys His Thr Thr Val Pro Trp Thr Trp Asn Asn
625                 630                 635                 640

Thr Pro Glu Trp Asn Asn Met Thr Trp Leu Glu Trp Glu Lys Gln Ile
                645                 650                 655

Glu Gly Leu Glu Gly Asn Ile Thr Lys Gln Leu Glu Gln Ala Arg Glu
                660                 665                 670

Gln Glu Glu Lys Asn Leu Asp Ala Tyr Gln Lys Leu Ser Asp Trp Ser
                675                 680                 685

Ser Phe Trp Ser Trp Phe Asp Phe Ser Lys Trp Leu Asn Ile Leu Lys
                690                 695                 700

Ile Gly Phe Leu Ala Val Ile Gly Val Ile Gly Leu Arg Leu Leu Tyr
705                 710                 715                 720

Thr Leu Tyr Thr Cys Ile Ala Arg Val Arg Gln Gly Tyr Ser Pro Leu
                725                 730                 735

Ser Pro Gln Ile His Ile His Pro Trp Lys Gly Gln Pro Asp Asn Ala
                740                 745                 750

Gly Glu Pro Glu Glu Gly Gly Arg Thr Gly Lys Ser Lys Ser Thr His
                755                 760                 765
```

<210> SEQ ID NO 5
<211> LENGTH: 879
<212> TYPE: PRT
<213> ORGANISM: Simian immunodeficiency virus agmTAN

<400> SEQUENCE: 5

```
Met Gly Pro Leu Arg Gly Lys Gly Val Leu Leu Val Ile Leu Gly Leu
1               5                   10                  15

Ser Leu Ile Gly Leu Leu Tyr Gly Thr Gln Tyr Ile Thr Val Phe Tyr
                20                  25                  30

Gly Ile Pro Val Trp Lys Asn Ser Ser Val Gln Ala Phe Cys Met Thr
                35                  40                  45

Pro Asn Thr Asn Leu Trp Ala Thr Thr Asn Cys Ile Pro Asp Asp His
                50                  55                  60

Asp Tyr Thr Glu Val Gln Leu Asn Val Ser Glu Lys Phe Glu Ala Trp
```

```
              65                  70                  75                  80
Lys Asp Arg Asn Pro Leu Val Ala Gln Ala Glu Ser Asn Ile His Leu
                        85                  90                  95

Leu Phe Glu Ser Thr Leu Lys Pro Cys Val Lys Leu Thr Pro Met Cys
            100                 105                 110

Ile Lys Met Asn Cys Thr Lys Leu Thr Ser Thr Ala Pro Thr Ser Ser
            115                 120                 125

Thr Pro Thr Ser Ser Thr Thr Asp Pro Cys Pro Asn Thr Asp Glu
        130                 135                 140

Ser Ser Cys Asn Ala Thr Leu Val Thr Asn Ser Met Asp Tyr Glu Asn
145                 150                 155                 160

Ser Ser Ile Cys Ser Phe Ala Met Ala Gly Tyr Arg Arg Asp Val Lys
                165                 170                 175

Lys Lys Tyr Asn Ser Thr Trp Tyr Asp Gln Glu Leu Val Cys Glu Lys
            180                 185                 190

Glu Asn Asn Thr Thr Gly Thr Arg Gly Cys Tyr Met Ile His Cys Asn
            195                 200                 205

Asp Ser Val Ile Lys Glu Ala Cys Glu Lys Thr Tyr Trp Asp Thr Leu
    210                 215                 220

Arg Leu Arg Tyr Cys Ala Pro Ala Gly Phe Ala Ile Leu Lys Cys Lys
225                 230                 235                 240

Asp Thr Asn Tyr Thr Gly Phe Gly Val Cys Arg Asn Val Ser Val Val
                245                 250                 255

Ser Cys Thr Gly Leu Met Asn Thr Thr Val Ser Ser Ala Phe Gly Ile
            260                 265                 270

Asn Gly Ser Gln Ala Glu Asn Arg Thr Glu Ile Trp Gln Lys His Gly
            275                 280                 285

Val Ser Asn Asn Ser Val Ile Ile Lys Leu Asn Lys His Tyr Lys Leu
    290                 295                 300

Lys Ile Val Cys Arg Arg Pro Gly Asn Lys Thr Val Leu Pro Val Thr
305                 310                 315                 320

Ile Met Ala Gly Leu Val Phe His Ser Gln Gln Tyr Asn Thr Lys Leu
                325                 330                 335

Arg Gln Ala Trp Cys His Phe Gln Gly Asp Trp Lys Gly Ala Trp Arg
            340                 345                 350

Glu Val Arg Lys Thr Ile Val Glu Leu Pro Lys Glu Lys Tyr Arg Gly
            355                 360                 365

Thr Asn Asn Thr Arg Gln Ile Trp Leu Ser Arg Gln Trp Gly Asp Pro
    370                 375                 380

Glu Ala Ala Asn Ile Trp Leu Asn Cys Gln Gly Glu Phe Phe Tyr Cys
385                 390                 395                 400

Thr Pro Asp Trp Phe Val Asn Trp Leu Asn Asn Glu Ser Asn Ser Gly
                405                 410                 415

Arg Asn Val Asp Val Glu Gly Asn Asn Cys Thr Gly Lys Asp Lys
            420                 425                 430

Arg Cys Tyr Lys Arg Thr Tyr Val Pro Cys His Ile Arg Ser Ile Val
            435                 440                 445

Asn Asp Trp Tyr Thr Leu Ser Lys Lys Thr Tyr Ala Pro Pro Arg Glu
    450                 455                 460

Gly His Leu Glu Cys Thr Ser Thr Val Thr Ser Met Met Val Ser Leu
465                 470                 475                 480

Asp Tyr Asn Ser Lys Glu Arg Thr Asn Val Thr Leu Thr Ala Asn Leu
                485                 490                 495
```

```
Glu Asn Ile Trp Ala Tyr Glu Leu Gly Arg Tyr Lys Leu Ile Glu Ile
                500                 505                 510

Glu Pro Ile Gly Phe Ala Pro Thr Glu Ile Arg Arg Tyr Val Gly Pro
            515                 520                 525

Thr Arg Glu Lys Arg Val Pro Phe Val Leu Gly Phe Leu Gly Phe Leu
        530                 535                 540

Gly Ala Gly Ala Ala Met Gly Ala Thr Ala Leu Thr Val
545                 550                 555                 560

Gln Ser Gln Gln Leu Leu Ala Gly Ile Leu Gln Gln Gln Lys Asn Leu
                565                 570                 575

Leu Ala Ala Val Glu Gln Gln Gln Met Leu Lys Leu Thr Ile Trp
            580                 585                 590

Gly Val Lys Asn Leu Asn Ala Arg Val Thr Ala Leu Glu Lys Tyr Leu
        595                 600                 605

Glu Asp Gln Thr Arg Leu Asn Leu Trp Gly Cys Ala Phe Lys Gln Val
    610                 615                 620

Cys His Thr Thr Val Pro Trp Thr Phe Asn Asn Thr Pro Asp Trp Asp
625                 630                 635                 640

Asn Met Thr Trp Gln Glu Trp Glu Ser Gln Ile Thr Ala Leu Glu Gly
                645                 650                 655

Asn Ile Ser Thr Thr Leu Val Lys Ala Tyr Glu Gln Glu Gln Lys Asn
            660                 665                 670

Met Asp Thr Tyr Gln Lys Leu Gly Asp Trp Thr Ser Trp Trp Asn Ile
        675                 680                 685

Phe Asp Val Ser Ser Trp Phe Trp Ile Lys Trp Gly Phe Tyr Ile
    690                 695                 700

Val Ile Gly Leu Ile Leu Phe Arg Met Ala Trp Leu Ile Trp Gly Cys
705                 710                 715                 720

Ile Ala Arg Val Arg Gln Gly Tyr Phe Pro Leu Ser Pro Gln Ile Asn
                725                 730                 735

Ile Arg Leu Gly Arg Glu Gln Pro Asp Asn Ala Gly Gly Glu Asp Lys
            740                 745                 750

Asp Ser Ser Ser Arg Asp Lys Ser Pro Pro Ser Val Lys Glu Ser
        755                 760                 765

Leu Leu Pro Asn Arg Gly Gly Ile Gln Ala Glu Glu Arg Ala Trp Arg
    770                 775                 780

Gln His Leu Thr Asn Trp Cys Leu Thr Ile Ser Ser Trp Leu Leu Arg
785                 790                 795                 800

Leu Tyr Gln Ile Leu Arg Arg Ser Leu Thr Thr Leu Gln Leu Leu
                805                 810                 815

Arg Gln Glu Cys Gln Tyr Ile Gln Tyr Gly Trp Gln Gln Phe Lys Glu
            820                 825                 830

Gly Ala Ala Arg Ser Phe Glu Ala Leu Ala Ser Ala Ala Gln Ser Ala
        835                 840                 845

Ser Arg Thr Leu Trp Asn Ala Cys Arg Ser Ala Tyr Arg Ala Ile Leu
    850                 855                 860

Glu His Pro Arg Arg Met Arg Gln Glu Leu Glu Arg Trp Phe Asn
865                 870                 875

<210> SEQ ID NO 6
<211> LENGTH: 390
<212> TYPE: PRT
<213> ORGANISM: Homo sapiens

<400> SEQUENCE: 6
```

```
Met Asn Arg Gly Val Pro Phe Arg His Leu Leu Val Leu Gln Leu
 1               5                  10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
 50                  55                  60

Gln Gly Ser Phe Leu Thr Lys Gly Pro Ser Lys Leu Asn Asp Arg Ala
 65              70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
             100                 105                 110

Asp Gln Lys Glu Glu Val Gln Leu Leu Val Phe Gly Leu Thr Ala Asn
         115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp
385                 390

<210> SEQ ID NO 7
<211> LENGTH: 857
<212> TYPE: PRT
<213> ORGANISM: Human immunodeficiency virus type 2 UC1
```

```
<400> SEQUENCE: 7

Met Ala His Thr Ser Asn His Leu Phe Ile Leu Leu Leu Leu Ile Ser
 1               5                   10                  15

Val Tyr Gly Phe Leu Gly His Lys Lys Asn Tyr Val Thr Val Phe Tyr
            20                  25                  30

Gly Ile Pro Ala Trp Arg Asn Ala Thr Val Pro Leu Phe Cys Ala Thr
        35                  40                  45

Thr Asn Arg Asp Thr Trp Gly Thr Val Gln Cys Leu Pro Asp Asn Gly
    50                  55                  60

Asp Tyr Thr Glu Ile Ser Val Asn Ile Thr Glu Ala Phe Asp Ala Trp
65                  70                  75                  80

Asn Asn Thr Val Thr Glu Gln Ala Val Asp Asp Val Trp Ser Leu Phe
                85                  90                  95

Glu Thr Ser Ile Lys Pro Cys Val Lys Leu Thr Pro Leu Cys Val Ala
            100                 105                 110

Met Arg Cys Asn Asn Thr Gly Thr Asn Thr Thr Lys Pro Ile Thr
        115                 120                 125

Thr Pro Ile Thr Thr Lys Pro Ser Glu Asn Leu Leu Asn Asp Thr
    130                 135                 140

Ser Pro Cys Ile Lys Asn Asp Thr Cys Pro Gly Ile Gly Leu Glu Asn
145                 150                 155                 160

Thr Val Asp Cys Tyr Phe Asn Met Thr Gly Leu Arg Arg Asp Glu Lys
                165                 170                 175

Lys Gln Tyr Lys Asp Thr Trp Tyr Glu Lys Asp Leu Glu Cys Asn Gly
            180                 185                 190

Asn Ser Thr Ser Thr Ile Cys Tyr Met Arg Thr Cys Asn Thr Ser Val
        195                 200                 205

Ile Gln Glu Ser Cys Asp Lys His Tyr Trp Asp Ser Leu Arg Phe Arg
    210                 215                 220

Tyr Cys Ala Pro Pro Gly Tyr Ala Leu Leu Arg Cys Asn Asp Thr Asn
225                 230                 235                 240

Tyr Ser Gly Phe Met Pro Lys Cys Ser Lys Val Val Ser Ser Cys
                245                 250                 255

Thr Arg Met Met Glu Thr Gln Thr Ser Thr Trp Phe Gly Phe Asn Gly
            260                 265                 270

Thr Arg Thr Glu Asn Arg Thr Tyr Met Tyr Trp His Ser Lys Asp Asn
        275                 280                 285

Arg Thr Ile Ile Ser Leu Asn Lys Tyr Tyr Asn Leu Thr Met His Cys
    290                 295                 300

Arg Arg Pro Gly Asn Lys Thr Val Ile Pro Ile Thr Ile Met Ser Gly
305                 310                 315                 320

Leu Asn Phe His Ser Gln Pro Leu Asn Thr Arg Pro Arg Gln Ala Trp
                325                 330                 335

Cys Trp Phe Lys Gly Asn Trp Ile Glu Ala Ile Arg Glu Val Lys Glu
            340                 345                 350

Thr Ile Ile Lys His Pro Arg Tyr Lys Gly Thr Asn Asn Thr Glu Arg
        355                 360                 365

Ile Arg Leu Val Gly Pro Ser Ala Gly Ser Asp Pro Glu Val Arg His
    370                 375                 380

Met Trp Thr Asn Cys Arg Gly Glu Phe Phe Tyr Cys Asn Met Thr Trp
385                 390                 395                 400

Phe Leu Asn Trp Val Glu Asn Arg Thr Gly Thr Thr Gln Lys Asn Tyr
                405                 410                 415
```

```
Val Thr Cys His Ile Lys Gln Ile Val Asn Thr Trp His Lys Val Gly
            420                 425                 430

Lys Tyr Val Tyr Leu Pro Pro Arg Glu Gly Thr Leu Ser Cys Asn Ser
        435                 440                 445

Ser Val Thr Ser Leu Ile Ala Asn Ile Asp Val Tyr Tyr Asp Gly Asn
450                 455                 460

Asp Thr Lys Thr Asn Ile Thr Met Ser Ala Glu Val Gly Glu Leu Tyr
465                 470                 475                 480

Arg Leu Glu Leu Gly Asp Tyr Lys Leu Val Glu Ile Thr Pro Ile Gly
                485                 490                 495

Phe Ala Pro Thr Glu Ile Lys Arg Tyr Ser Ser Thr Thr Pro Arg Asn
            500                 505                 510

Lys Arg Gly Val Met Val Leu Gly Phe Leu Gly Leu Leu Ala Met Ala
                515                 520                 525

Gly Ser Ala Met Gly Ala Thr Ser Leu Thr Leu Ser Ala Gln Ser Arg
530                 535                 540

Thr Leu Leu Ala Gly Ile Val Gln Gln Gln Gln Gln Leu Leu Asp Val
545                 550                 555                 560

Val Lys Arg Gln Gln Glu Leu Leu Arg Leu Thr Val Trp Gly Thr Lys
                565                 570                 575

Asn Leu Gln Thr Arg Val Thr Ala Ile Glu Lys Tyr Leu Lys Asp Gln
                580                 585                 590

Ala Leu Leu Asn Ser Trp Gly Cys Ala Phe Arg Gln Val Cys His Thr
                595                 600                 605

Thr Val Pro Trp Pro Asn Glu Thr Leu Thr Pro Asp Trp Glu Asn Met
610                 615                 620

Thr Trp Gln Gln Trp Glu Lys Arg Val Asn Phe Leu Asp Ala Asn Ile
625                 630                 635                 640

Thr Ala Leu Leu Glu Glu Ala Gln Ile Gln Gln Glu Arg Asn Met Tyr
                645                 650                 655

Glu Leu Gln Lys Leu Asn Ser Trp Asp Val Phe Gly Asn Trp Phe Asp
                660                 665                 670

Phe Thr Ser Trp Met Ala Tyr Ile Arg Leu Gly Leu Tyr Val Val Ala
            675                 680                 685

Gly Leu Ile Val Leu Arg Ile Val Ile Tyr Ile Met Gln Met Leu Ala
690                 695                 700

Arg Leu Arg Lys Gly Tyr Arg Pro Val Phe Ser Ser Pro Ser Tyr
705                 710                 715                 720

Thr Gln Gln Ile Pro Ile Arg Lys His Arg Gly Gln Pro Ala Asn Glu
            725                 730                 735

Glu Thr Glu Asp Glu Gly Gly Asn Glu Gly Ala Tyr Arg Ser Trp Pro
            740                 745                 750

Trp Gln Ile Glu Tyr Ala His Phe Leu Ile Arg Gln Leu Arg Asn Leu
            755                 760                 765

Leu Ile Trp Leu Tyr Asn Gly Cys Arg Asn Leu Leu Leu Lys Thr Ser
770                 775                 780

Gln Ile Leu Gln Pro Ala Leu Gln Pro Leu Arg Leu Ser Leu Ala Tyr
785                 790                 795                 800

Leu Gln Tyr Gly Ile Ser Trp Phe Gln Glu Ala Ile Gln Ala Ala Thr
                805                 810                 815

Arg Ala Ala Arg Glu Thr Leu Ala Asn Thr Gly Arg Ala Leu Trp Lys
            820                 825                 830

Ala Leu Arg Arg Thr Ala Glu Ala Ile Ile Ala Ile Pro Arg Arg Ile
```

```
                   835                 840                 845
Arg Gln Gly Leu Glu Leu Ala Leu Leu
    850                 855

<210> SEQ ID NO 8
<211> LENGTH: 865
<212> TYPE: PRT
<213> ORGANISM: Human immunodeficiency virus type 2 UC2

<400> SEQUENCE: 8

Met Glu Pro Gly Arg Asn Gln Leu Leu Ala Val Ile Leu Leu Thr Ser
1               5                   10                  15

Ala Cys Leu Ile Tyr Cys Lys Gln Tyr Val Thr Val Phe Tyr Gly Val
                20                  25                  30

Pro Val Trp Arg Asn Ala Ser Ile Pro Leu Phe Cys Ala Thr Lys Asn
            35                  40                  45

Arg Asp Thr Trp Gly Thr Ile Gln Cys Leu Pro Asp Asn Asp Asp Tyr
    50                  55                  60

Gln Glu Ile Pro Leu Asn Val Thr Glu Ala Phe Asp Ala Trp Asp Asn
65                  70                  75                  80

Thr Val Thr Glu Gln Ala Ile Glu Asp Val Trp Arg Leu Phe Glu Thr
                85                  90                  95

Ser Ile Lys Pro Cys Val Lys Leu Thr Pro Leu Cys Val Ala Met Asn
            100                 105                 110

Cys Asn Pro Val Thr Gly Asn Asn Thr Asn Ala Thr Ala Lys Pro Thr
    115                 120                 125

Ala Ala Arg Pro Thr Thr Asn Pro Ser Tyr Leu Thr Ile Ile Asn Glu
130                 135                 140

Ser Ser Thr Cys Val Gly Ala Asp Asn Cys Thr Gly Leu Gly Asp Glu
145                 150                 155                 160

Gly Met Val Asn Cys Lys Phe Asn Met Thr Gly Leu Glu Gln Asp Lys
                165                 170                 175

Ile Lys Gly Tyr Thr Asp Thr Trp Tyr Ser Asp Val Val Cys Asp
            180                 185                 190

Ser Thr Asn Lys Thr Gly Thr Asn Thr Thr Cys Tyr Met Arg His Cys
    195                 200                 205

Asn Thr Ser Val Ile Lys Glu Ser Cys Asp Lys His Tyr Trp Asp Ser
210                 215                 220

Met Lys Phe Arg Tyr Cys Thr Pro Pro Gly Tyr Ala Leu Leu Arg Cys
225                 230                 235                 240

Asn Asp Thr Asn Tyr Ser Gly Phe Ala Pro Asn Cys Pro Lys Val Val
                245                 250                 255

Ala Ala Ser Cys Thr Arg Met Met Glu Thr Gln Thr Ser Thr Trp Phe
            260                 265                 270

Gly Phe Asn Gly Thr Arg Ala Glu Asn Arg Thr Tyr Ile Tyr Trp His
    275                 280                 285

Gly Arg Asp Asn Arg Thr Ile Ile Ser Leu Asn Lys His Tyr Asn Leu
290                 295                 300

Thr Met His Cys Lys Arg Pro Gly Asn Lys Thr Val Val Pro Ile Thr
305                 310                 315                 320

Leu Met Ser Gly His Arg Phe His Ser Gln Ala Val Ile Asn Lys Lys
                325                 330                 335

Pro Arg Gln Ala Trp Cys Trp Phe Lys Gly Asn Trp Lys Gly Ala Met
            340                 345                 350

Gln Glu Val Lys Gln Thr Leu Ala Gly His Pro Arg Tyr Lys Gly Thr
```

-continued

```
            355                 360                 365
Asn Asp Thr Ser Lys Ile Asn Phe Val Lys Pro Gly Val Gly Ser Asp
    370                 375                 380

Pro Glu Val Thr Tyr Met Trp Thr Asn Cys Arg Gly Glu Phe Phe Tyr
385                 390                 395                 400

Cys Asn Met Thr Trp Phe Leu Asn Trp Val Glu Asn Arg Thr Ser Gln
                405                 410                 415

Lys Gln Arg Asn Tyr Ala Pro Cys His Ile Arg Gln Ile Ile Asn Thr
        420                 425                 430

Trp His Lys Val Gly Gln Tyr Val Tyr Leu Pro Pro Arg Glu Gly Glu
            435                 440                 445

Leu Thr Cys Asn Ser Thr Val Thr Ser Ile Ile Ala Asn Ile Asp Thr
                450                 455                 460

Asp Gly Asn Gln Thr Asn Ile Thr Phe Ser Ala Glu Val Ala Glu Leu
465                 470                 475                 480

Tyr Arg Leu Glu Leu Gly Asp Tyr Lys Leu Ile Glu Ile Thr Pro Ile
                485                 490                 495

Gly Phe Ala Pro Thr Ser Glu Lys Arg Tyr Ser Ser Ala Pro Ala Arg
                500                 505                 510

Asn Lys Arg Gly Val Phe Val Leu Gly Leu Leu Gly Phe Leu Ala Thr
        515                 520                 525

Ala Gly Ser Ala Met Gly Ala Ala Ser Leu Thr Leu Ser Ala Gln Ser
    530                 535                 540

Arg Thr Leu Leu Ala Gly Ile Val Gln Gln Gln Gln Gln Leu Leu Asp
545                 550                 555                 560

Ile Val Lys Arg Gln Gln Glu Leu Leu Arg Leu Thr Val Trp Gly Thr
                565                 570                 575

Lys Asn Leu Gln Ala Arg Val Thr Ala Ile Glu Lys Tyr Leu Lys Asp
                580                 585                 590

Gln Ala Gln Leu Asn Ser Trp Gly Cys Thr Phe Arg Gln Val Cys His
    595                 600                 605

Thr Thr Val Pro Trp Val Asn Asp Ser Leu Thr Pro Arg Trp Asn Asn
    610                 615                 620

Met Thr Trp Gln Glu Trp Glu Lys Gln Val Arg Tyr Leu Glu Ala Asn
625                 630                 635                 640

Ile Ser Gln Ser Leu Glu Glu Ala Gln Ile Gln Gln Glu Lys Asn Met
                645                 650                 655

Tyr Glu Leu Gln Lys Leu Asn Ser Trp Asp Val Phe Gly Asn Trp Phe
                660                 665                 670

Asp Leu Thr Ser Trp Ile Lys Tyr Ile Gln Tyr Gly Val Tyr Ile Val
            675                 680                 685

Val Gly Ile Ile Ala Leu Arg Ile Ala Ile Tyr Val Val Gln Leu Leu
    690                 695                 700

Ser Arg Phe Arg Lys Gly Tyr Arg Pro Val Phe Ser Ser Pro Pro Gly
705                 710                 715                 720

Tyr Leu Gln Gln Ile His Ile His Thr Asp Arg Gly Gln Pro Ala Asn
                725                 730                 735

Glu Glu Thr Glu Gly Asp Ala Gly Asp Ala Ser Gly Tyr Asp Phe Trp
                740                 745                 750

Pro Trp Pro Ile Asn Tyr Ile Gln Leu Leu Ile His Leu Leu Thr Arg
            755                 760                 765

Leu Leu Thr Gly Leu Tyr Ser Ile Cys Arg Asp Leu Leu Ser Ala Asn
        770                 775                 780
```

```
Ser Pro Thr Arg Arg Leu Ile Ser Gln Asn Leu Thr Ala Ile Arg Asp
785                 790                 795                 800

Trp Leu Arg Leu Lys Ala Ala Tyr Leu Gln Tyr Gly Cys Glu Trp Ile
            805                 810                 815

Gln Glu Ala Phe Gln Ala Ile Ala Arg Thr Ala Arg Glu Thr Leu Ala
        820                 825                 830

Gly Ala Trp Arg Gly Leu Cys Lys Ala Val Gln Arg Ile Gly Arg Gly
            835                 840                 845

Ile Leu Ala Val Pro Arg Arg Ile Arg Gln Gly Ala Glu Ile Ala Leu
850                 855                 860

Leu
865

<210> SEQ ID NO 9
<211> LENGTH: 443
<212> TYPE: PRT
<213> ORGANISM: Human immunodeficiency virus type2 ROD/D.14

<400> SEQUENCE: 9

Met Met Asn Gln Leu Leu Ile Ala Ile Leu Leu Ala Ser Ala Cys Leu
1               5                   10                  15

Val Tyr Cys Thr Gln Tyr Val Thr Val Phe Tyr Gly Val Pro Thr Trp
            20                  25                  30

Lys Asn Ala Thr Ile Pro Leu Phe Cys Ala Thr Arg Asn Arg Asp Thr
        35                  40                  45

Trp Gly Thr Ile Gln Cys Leu Pro Asp Asn Asp Asp Tyr Gln Glu Ile
    50                  55                  60

Thr Leu Asn Val Thr Glu Ala Phe Asp Ala Trp Asn Asn Thr Val Thr
65                  70                  75                  80

Glu Gln Ala Ile Glu Asp Val Trp His Leu Phe Glu Thr Ser Ile Lys
                85                  90                  95

Pro Cys Val Lys Leu Thr Pro Leu Cys Val Ala Met Lys Cys Ser Ser
            100                 105                 110

Thr Glu Ser Ser Ile Gly Asn Asn Thr Thr Ser Lys Ser Thr Ser Thr
        115                 120                 125

Thr Thr Thr Thr Pro Thr Asp Gln Glu Gln Glu Ile Ser Glu Asp Thr
    130                 135                 140

Pro Cys Ala Arg Ala Asp Asn Cys Ser Gly Leu Gly Lys Glu Glu Thr
145                 150                 155                 160

Ile Asn Cys Gln Phe Asn Met Thr Gly Leu Glu Arg Asp Lys Lys Lys
                165                 170                 175

Gln Tyr Asn Glu Thr Trp Tyr Ser Lys Asp Val Val Cys Lys Thr Asn
            180                 185                 190

Asn Ser Thr Asn Gln Thr Gln Cys Tyr Met Asn His Cys Asn Thr Ser
        195                 200                 205

Val Ile Thr Glu Ser Cys Asp Lys His Tyr Trp Asp Ala Ile Arg Phe
    210                 215                 220

Arg Tyr Cys Ala Pro Pro Gly Tyr Ala Leu Leu Arg Cys Asn Asp Thr
225                 230                 235                 240

Asn Tyr Ser Gly Phe Ala Pro Asn Cys Ser Lys Val Val Ala Ser Thr
                245                 250                 255

Cys Thr Arg Met Met Glu Thr Gln Thr Ser Thr Trp Phe Gly Phe Asn
            260                 265                 270

Gly Thr Arg Ala Glu Asn Arg Thr Tyr Ile Tyr Trp His Gly Arg Asp
        275                 280                 285
```

```
Asn Arg Thr Ile Ile Ser Leu Asn Lys Tyr Tyr Asn Leu Ser Leu His
        290                 295                 300

Cys Lys Arg Pro Gly Asn Lys Thr Val Lys Gln Ile Met Leu Met Ser
305                 310                 315                 320

Gly His Val Phe His Ser His Tyr Lys Pro Ile Asn Lys Arg Pro Arg
                    325                 330                 335

Gln Ala Trp Cys Trp Phe Lys Gly Lys Trp Lys Asp Ala Met Gln Glu
                340                 345                 350

Val Lys Glu Thr Leu Ala Lys His Pro Arg Tyr Arg Gly Thr Asn Asp
            355                 360                 365

Thr Arg Asn Ile Ser Phe Ala Ala Pro Gly Lys Gly Ser Asp Pro Glu
        370                 375                 380

Val Ala Tyr Met Trp Thr Asn Cys Arg Gly Glu Phe Phe Tyr Cys Asn
385                 390                 395                 400

Met Thr Trp Phe Leu Asn Trp Ile Glu Asn Lys Thr His Arg Asn Tyr
                    405                 410                 415

Ala Pro Cys His Ile Arg Gln Ile Ile Asn Thr Trp His Lys Val Gly
                420                 425                 430

Ile Asn Val Tyr Leu Pro Pro Arg Glu Gly Glu
            435                 440

<210> SEQ ID NO 10
<211> LENGTH: 856
<212> TYPE: PRT
<213> ORGANISM: Human immunodeficiency virus type HXB2

<400> SEQUENCE: 10

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
                20                  25                  30

Lys Leu Trp Val Thr Val Tyr Tyr Gly Val Pro Val Trp Lys Glu Ala
            35                  40                  45

Thr Thr Thr Leu Phe Cys Ala Ser Asp Ala Lys Ala Tyr Asp Thr Glu
        50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
210                 215                 220
```

-continued

```
Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
            245                 250                 255

Thr Gln Leu Leu Leu Asn Gly Ser Leu Ala Glu Glu Val Val Ile
        260                 265                 270

Arg Ser Val Asn Phe Thr Asp Asn Ala Lys Thr Ile Ile Val Gln Leu
    275                 280                 285

Asn Thr Ser Val Glu Ile Asn Cys Thr Arg Pro Asn Asn Asn Thr Arg
290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
            325                 330                 335

Lys Trp Asn Asn Thr Leu Lys Gln Ile Ala Ser Lys Leu Arg Glu Gln
        340                 345                 350

Phe Gly Asn Asn Lys Thr Ile Ile Phe Lys Gln Ser Ser Gly Gly Asp
    355                 360                 365

Pro Glu Ile Val Thr His Ser Phe Asn Cys Gly Gly Glu Phe Phe Tyr
370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
            405                 410                 415

Pro Cys Arg Ile Lys Gln Ile Ile Asn Met Trp Gln Lys Val Gly Lys
        420                 425                 430

Ala Met Tyr Ala Pro Pro Ile Ser Gly Gln Ile Arg Cys Ser Ser Asn
    435                 440                 445

Ile Thr Gly Leu Leu Leu Thr Arg Asp Gly Gly Asn Ser Asn Asn Glu
        450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
            485                 490                 495

Ala Pro Thr Lys Ala Lys Arg Arg Val Val Gln Arg Glu Lys Arg Ala
        500                 505                 510

Val Gly Ile Gly Ala Leu Phe Leu Gly Phe Leu Gly Ala Ala Gly Ser
    515                 520                 525

Thr Met Gly Ala Ala Ser Met Thr Leu Thr Val Gln Ala Arg Gln Leu
530                 535                 540

Leu Ser Gly Ile Val Gln Gln Asn Asn Leu Leu Arg Ala Ile Glu
545                 550                 555                 560

Ala Gln Gln His Leu Leu Gln Leu Thr Val Trp Gly Ile Lys Gln Leu
            565                 570                 575

Gln Ala Arg Ile Leu Ala Val Glu Arg Tyr Leu Lys Asp Gln Gln Leu
        580                 585                 590

Leu Gly Ile Trp Gly Cys Ser Gly Lys Leu Ile Cys Thr Thr Ala Val
    595                 600                 605

Pro Trp Asn Ala Ser Trp Ser Asn Lys Ser Leu Glu Gln Ile Trp Asn
610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
            645                 650                 655
```

Glu Gln Glu Leu Leu Glu Leu Asp Lys Trp Ala Ser Leu Trp Asn Trp
                660                 665                 670

Phe Asn Ile Thr Asn Trp Leu Trp Tyr Ile Lys Leu Phe Ile Met Ile
            675                 680                 685

Val Gly Gly Leu Val Gly Leu Arg Ile Val Phe Ala Val Leu Ser Ile
        690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
                740                 745                 750

Leu Ala Leu Ile Trp Asp Asp Leu Arg Ser Leu Cys Leu Phe Ser Tyr
            755                 760                 765

His Arg Leu Arg Asp Leu Leu Leu Ile Val Thr Arg Ile Val Glu Leu
            770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
                835                 840                 845

Gln Gly Leu Glu Arg Ile Leu Leu
                850                 855

<210> SEQ ID NO 11
<211> LENGTH: 879
<212> TYPE: PRT
<213> ORGANISM: Simian immunodeficiency virus (Mac239)
<220> FEATURE:
<221> NAME/KEY: VARIANT
<222> LOCATION: 176, 792
<223> OTHER INFORMATION: Xaa = Any Amino Acid

<400> SEQUENCE: 11

Met Gly Cys Leu Gly Asn Gln Leu Leu Ile Ala Ile Leu Leu Leu Ser
 1               5                  10                  15

Val Tyr Gly Ile Tyr Cys Thr Leu Tyr Val Thr Val Phe Tyr Gly Val
            20                  25                  30

Pro Ala Trp Arg Asn Ala Thr Ile Pro Leu Phe Cys Ala Thr Lys Asn
            35                  40                  45

Arg Asp Thr Trp Gly Thr Thr Gln Cys Leu Pro Asp Asn Gly Asp Tyr
        50                  55                  60

Ser Glu Met Ala Leu Asn Val Thr Glu Ser Phe Asp Ala Trp Asn Asn
65                  70                  75                  80

Thr Val Thr Glu Gln Ala Ile Glu Asp Val Trp Gln Leu Phe Glu Thr
                85                  90                  95

Ser Ile Arg Pro Cys Val Lys Leu Ser Pro Leu Cys Ile Thr Met Arg
            100                 105                 110

Cys Asn Lys Ser Glu Thr Asp Arg Trp Gly Leu Thr Lys Ser Ile Thr
        115                 120                 125

Thr Thr Ala Ser Thr Thr Ser Thr Thr Ala Ser Ala Lys Val Asp Met
    130                 135                 140

Val Asn Glu Thr Ser Ser Cys Ile Ala Gln Asp Asn Cys Thr Gly Leu

```
            145                 150                 155                 160
Glu Gln Glu Gln Met Ile Ser Cys Lys Phe Asn Met Thr Gly Leu Xaa
                165                 170                 175
Arg Asp Lys Lys Lys Glu Tyr Asn Gly Thr Trp Tyr Ser Ala Asp Leu
                180                 185                 190
Val Cys Glu Gln Gly Asn Asn Thr Gly Asn Glu Ser Arg Cys Tyr Met
                195                 200                 205
Asn His Cys Asn Thr Ser Val Ile Gln Glu Ser Cys Asp Lys His Tyr
                210                 215                 220
Trp Asp Ala Ile Arg Phe Arg Tyr Cys Ala Pro Pro Gly Tyr Ala Leu
225                 230                 235                 240
Leu Arg Cys Asn Asp Thr Asn Tyr Ser Gly Phe Met Pro Lys Cys Ser
                245                 250                 255
Lys Val Val Ser Ser Cys Thr Arg Met Met Glu Thr Gln Thr Ser
                260                 265                 270
Thr Trp Phe Gly Phe Asn Gly Thr Arg Ala Glu Asn Arg Thr Tyr Ile
                275                 280                 285
Tyr Trp His Gly Arg Asp Asn Arg Thr Ile Ile Ser Leu Asn Lys Tyr
                290                 295                 300
Tyr Asn Leu Thr Met Lys Cys Arg Arg Pro Gly Asn Lys Thr Val Leu
305                 310                 315                 320
Pro Val Thr Ile Met Ser Gly Leu Val Phe His Ser Gln Pro Ile Asn
                325                 330                 335
Asp Arg Pro Lys Gln Ala Trp Cys Trp Phe Gly Gly Lys Trp Lys Asp
                340                 345                 350
Ala Ile Lys Glu Val Lys Gln Thr Ile Val Lys His Pro Arg Tyr Thr
                355                 360                 365
Gly Thr Asn Asn Thr Asp Lys Ile Asn Leu Thr Ala Pro Arg Gly Gly
                370                 375                 380
Asp Pro Glu Val Thr Phe Met Trp Thr Asn Cys Arg Gly Glu Phe Leu
385                 390                 395                 400
Tyr Cys Lys Met Asn Trp Phe Leu Asn Trp Val Glu Asp Arg Asn Thr
                405                 410                 415
Ala Asn Gln Lys Pro Lys Glu Gln His Lys Arg Asn Tyr Val Pro Cys
                420                 425                 430
His Ile Arg Gln Ile Ile Asn Thr Trp His Lys Val Gly Lys Asn Val
                435                 440                 445
Tyr Leu Pro Pro Arg Glu Gly Asp Leu Thr Cys Asn Ser Thr Val Thr
450                 455                 460
Ser Leu Ile Ala Asn Ile Asp Trp Ile Asp Gly Asn Gln Thr Asn Ile
465                 470                 475                 480
Thr Met Ser Ala Glu Val Ala Glu Leu Tyr Arg Leu Glu Leu Gly Asp
                485                 490                 495
Tyr Lys Leu Val Glu Ile Thr Pro Ile Gly Leu Ala Pro Thr Asx Val
                500                 505                 510
Lys Arg Tyr Thr Thr Gly Gly Thr Ser Arg Asn Lys Arg Gly Val Phe
                515                 520                 525
Val Leu Gly Phe Leu Gly Phe Leu Ala Thr Ala Gly Ser Ala Met Gly
                530                 535                 540
Ala Ala Ser Leu Thr Leu Thr Ala Gln Ser Arg Thr Leu Leu Ala Gly
545                 550                 555                 560
Ile Val Gln Gln Gln Gln Gln Leu Leu Asp Val Val Lys Arg Gln Gln
                565                 570                 575
```

```
Glu Leu Leu Arg Leu Thr Val Trp Gly Thr Lys Asn Leu Gln Thr Arg
            580                 585                 590

Val Thr Ala Ile Glu Lys Tyr Leu Lys Asp Gln Ala Gln Leu Asn Ala
            595                 600                 605

Trp Gly Cys Ala Phe Arg Gln Val Cys His Thr Thr Val Pro Trp Pro
            610                 615                 620

Asn Ala Ser Leu Thr Pro Lys Trp Asn Asn Glu Thr Trp Gln Glu Trp
625                 630                 635                 640

Glu Arg Lys Val Asp Phe Leu Glu Glu Asn Ile Thr Ala Leu Leu Glu
            645                 650                 655

Glu Ala Gln Ile Gln Gln Glu Lys Asn Met Tyr Glu Leu Gln Lys Leu
            660                 665                 670

Asn Ser Trp Asp Val Phe Gly Asn Trp Phe Asp Leu Ala Ser Trp Ile
            675                 680                 685

Lys Tyr Ile Gln Tyr Gly Val Tyr Ile Val Val Gly Val Ile Leu Leu
            690                 695                 700

Arg Ile Val Ile Tyr Ile Val Gln Met Leu Ala Lys Leu Arg Gln Gly
705                 710                 715                 720

Tyr Arg Pro Val Phe Ser Ser Pro Pro Ser Tyr Phe Gln Gln Thr His
            725                 730                 735

Ile Gln Gln Asp Pro Ala Leu Pro Thr Arg Glu Gly Lys Glu Gly Asp
            740                 745                 750

Gly Gly Glu Gly Gly Gly Asn Ser Ser Trp Pro Trp Gln Ile Glu Tyr
            755                 760                 765

Ile His Phe Leu Ile Arg Gln Leu Ile Arg Leu Leu Thr Trp Leu Phe
            770                 775                 780

Ser Asn Cys Arg Thr Leu Leu Xaa Arg Val Tyr Gln Ile Leu Gln Pro
785                 790                 795                 800

Ile Leu Gln Arg Leu Ser Ala Thr Leu Gln Arg Ile Arg Glu Val Leu
            805                 810                 815

Arg Thr Glu Leu Ala Tyr Leu Gln Tyr Gly Trp Ser Tyr Phe His Glu
            820                 825                 830

Ala Val Gln Ala Val Trp Arg Ser Ala Thr Glu Thr Leu Ala Gly Ala
            835                 840                 845

Trp Gly Asp Leu Trp Glu Thr Leu Arg Arg Gly Gly Arg Trp Ile Leu
850                 855                 860

Ala Ile Pro Arg Arg Ile Arg Gln Gly Leu Glu Leu Thr Leu Leu
865                 870                 875

<210> SEQ ID NO 12
<211> LENGTH: 865
<212> TYPE: PRT
<213> ORGANISM: Simian immunodeficiency virus Ver-Ty01
<220> FEATURE:
<221> NAME/KEY: VARIANT
<222> LOCATION: 770
<223> OTHER INFORMATION: Xaa = Any Amino Acid

<400> SEQUENCE: 12

Met Arg Tyr Thr Ile Ile Thr Leu Gly Ile Val Ile Gly Ile Gly Ile
1               5                   10                  15

Ile Val Leu Ser Lys Gln Trp Ile Thr Val Phe Tyr Gly Ile Pro Val
            20                  25                  30

Trp Lys Asn Ser Ser Val Gln Ala Phe Cys Met Thr Pro Thr Thr Ser
            35                  40                  45

Leu Trp Ala Thr Thr Asn Cys Ile Pro Asp Asp His Asp Tyr Thr Glu
            50                  55                  60
```

```
Val Pro Leu Asn Ile Thr Glu Pro Phe Glu Ala Trp Gly Asp Arg Asn
 65                  70                  75                  80

Pro Leu Ile Ala Gln Ala Ala Ser Asn Ile His Leu Leu Phe Glu Gln
                 85                  90                  95

Thr Met Lys Pro Cys Val Lys Leu Ser Pro Leu Cys Ile Lys Met Asn
            100                 105                 110

Cys Val Glu Leu Asn Ser Thr Arg Glu Arg Ala Thr Thr Pro Thr Thr
            115                 120                 125

Thr Pro Lys Ser Thr Gly Leu Pro Cys Val Gly Pro Thr Ser Gly Glu
            130                 135                 140

Asn Leu Gln Ser Cys Asn Ala Ser Ile Ile Glu Arg Glu Met Glu Asp
145                 150                 155                 160

Glu Pro Ala Ser Asn Cys Thr Phe Ala Met Ala Gly Tyr Val Arg Asp
                165                 170                 175

Gln Lys Lys Asn Tyr Tyr Ser Val Val Trp Asn Asp Ala Glu Ile Tyr
            180                 185                 190

Cys Lys Asn Lys Thr Asn Ser Thr Ser Lys Glu Cys Tyr Met Ile His
            195                 200                 205

Cys Asn Asp Ser Val Ile Lys Glu Ala Cys Asp Lys Thr Tyr Trp Asp
210                 215                 220

Gln Leu Arg Leu Arg Tyr Cys Ala Pro Ala Gly Tyr Ala Leu Leu Lys
225                 230                 235                 240

Cys Asn Asp Glu Asp Tyr Asn Gly Tyr Lys Gln Asn Cys Ser Asn Val
                245                 250                 255

Ser Val Val His Cys Thr Gly Leu Met Asn Thr Thr Val Thr Thr Gly
                260                 265                 270

Leu Leu Leu Asn Gly Ser Tyr His Glu Asn Arg Thr Gln Ile Trp Gln
            275                 280                 285

Lys His Arg Val Asn Asn Asn Thr Val Leu Ile Leu Phe Asn Lys His
            290                 295                 300

Tyr Asn Leu Ser Val Thr Cys Arg Arg Pro Gly Asn Lys Thr Val Leu
305                 310                 315                 320

Pro Val Thr Ile Met Ala Gly Leu Val Phe His Ser Gln Lys Tyr Asn
                325                 330                 335

Met Lys Leu Arg Gln Ala Trp Cys His Phe Glu Gly Asn Trp Arg Gly
            340                 345                 350

Ala Trp Arg Glu Val Lys Gln Lys Ile Val Glu Leu Pro Lys Asp Arg
            355                 360                 365

Tyr Lys Gly Thr Asn Asn Thr Glu His Ile Tyr Leu Gln Arg Gln Trp
370                 375                 380

Gly Asp Pro Glu Ala Ser Asn Leu Trp Phe Asn Cys Gln Gly Glu Phe
385                 390                 395                 400

Phe Tyr Cys Lys Met Asp Trp Phe Leu Asn Tyr Leu Asn Asn Lys Thr
                405                 410                 415

Trp Asp Ala Tyr His Asn Phe Cys Ser Ser Lys Lys Gly His Ala
            420                 425                 430

Pro Gly Pro Cys Val Gln Arg Thr Tyr Val Ala Tyr His Ile Arg Ser
            435                 440                 445

Val Ile Asn Asp Ser Tyr Thr Leu Ser Lys Thr Tyr Ala Pro Pro
            450                 455                 460

Arg Glu Gly His Leu Gln Cys Arg Ser Thr Val Thr Gly Met Thr Val
465                 470                 475                 480

Glu Leu Asn Tyr Asn Ser Lys Asn Arg Thr Asn Val Thr Leu Ser Pro
```

```
                    485                 490                 495
Gln Ile Glu Ser Ile Trp Ala Ala Glu Leu Gly Arg Tyr Lys Leu Val
                500                 505                 510

Glu Ile Thr Pro Ile Gly Phe Ala Pro Thr Glu Val Arg Arg Tyr Thr
            515                 520                 525

Gly Gly His Glu Arg Gln Lys Arg Val Pro Phe Val Leu Gly Phe Leu
        530                 535                 540

Gly Phe Leu Gly Ala Ala Gly Thr Ala Met Gly Ala Ala Ser Ser
545                 550                 555                 560

Leu Thr Val Gln Ser Arg His Leu Leu Ala Gly Ile Leu Gln Gln Gln
                565                 570                 575

Lys Asn Leu Leu Ala Ala Val Glu Ala Gln Gln Gln Met Leu Lys Leu
                580                 585                 590

Thr Ile Trp Gly Val Lys Asn Leu Asn Ala Arg Val Thr Ala Leu Glu
                595                 600                 605

Lys Tyr Leu Glu Asp Gln Ala Arg Leu Asn Ser Trp Gly Cys Ala Trp
            610                 615                 620

Lys Gln Val Cys His Thr Thr Val Glu Trp Pro Trp Thr Asn Arg Thr
625                 630                 635                 640

Pro Asp Trp Gln Asn Met Thr Trp Leu Glu Trp Glu Arg Gln Ile Ala
                645                 650                 655

Asp Leu Glu Ser Asn Ile Thr Gly Gln Leu Val Lys Ala Arg Glu Gln
            660                 665                 670

Glu Glu Lys Asn Leu Asp Ala Tyr Gln Lys Leu Thr Ser Trp Ser Asp
        675                 680                 685

Phe Trp Ser Trp Phe Asp Phe Ser Lys Trp Leu Asn Ile Leu Lys Met
690                 695                 700

Gly Phe Leu Val Ile Val Gly Ile Ile Gly Leu Arg Leu Leu Tyr Thr
705                 710                 715                 720

Val Tyr Gly Cys Ile Val Arg Val Arg Gln Gly Tyr Val Pro Leu Ser
                725                 730                 735

Pro Gln Ile His Ile His Gln Val Gly Lys Gly Arg Pro Asp Asn Ala
            740                 745                 750

Asp Glu Pro Gly Glu Gly Gly Asp Asn Ser Arg Ile Lys Leu Glu Ser
        755                 760                 765

Trp Xaa Lys Asp Ser Lys Ser Arg Cys Met Gln Leu Thr Ala Trp Leu
    770                 775                 780

Thr Arg Leu Asn Thr Trp Leu Tyr Asn Ser Cys Leu Thr Leu Leu Ile
785                 790                 795                 800

Gln Leu Arg Lys Ala Phe Gln Tyr Leu Gln Tyr Gly Leu Ala Glu Leu
                805                 810                 815

Lys Thr Gly Ala Gln Glu Ile Leu Gln Thr Leu Ala Gly Val Ala Gln
            820                 825                 830

Asn Ala Cys His Gln Ile Trp Leu Ala Cys Arg Ser Ala Tyr Arg Asn
        835                 840                 845

Ile Val Asn Ser Pro Arg Arg Val Arg Gln Gly Leu Glu Glu Ile Leu
    850                 855                 860

Asn
865

<210> SEQ ID NO 13
<211> LENGTH: 843
<212> TYPE: PRT
<213> ORGANISM: Human immunodeficiency virus type 1 (YU2 isolate)
```

<400> SEQUENCE: 13

```
Met Arg Ala Thr Glu Ile Arg Lys Asn Tyr Gln His Leu Trp Lys Gly
  1               5                  10                  15

Gly Thr Leu Leu Leu Gly Met Leu Met Ile Cys Ser Ala Ala Glu Gln
             20                  25                  30

Leu Trp Val Thr Val Tyr Tyr Gly Val Pro Val Trp Lys Glu Ala Thr
         35                  40                  45

Thr Thr Leu Phe Cys Ala Ser Asp Ala Lys Ala Tyr Asp Thr Glu Val
 50                  55                  60

His Asn Val Trp Ala Thr His Ala Cys Val Pro Thr Asp Pro Asn Pro
 65                  70                  75                  80

Gln Glu Val Lys Leu Glu Asn Val Thr Glu Asn Phe Asn Met Trp Lys
             85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Arg Asn Ala Thr Asn Thr Thr Ser Ser Ser Trp
130                 135                 140

Glu Thr Met Glu Lys Gly Glu Ile Lys Asn Cys Ser Phe Asn Ile Thr
145                 150                 155                 160

Thr Ser Ile Arg Asp Lys Val Gln Lys Glu Tyr Ala Leu Phe Tyr Asn
                165                 170                 175

Leu Asp Val Val Pro Ile Asp Asn Ala Ser Tyr Arg Leu Ile Ser Cys
            180                 185                 190

Asn Thr Ser Val Ile Thr Gln Ala Cys Pro Lys Val Ser Phe Glu Pro
        195                 200                 205

Ile Pro Ile His Tyr Cys Ala Pro Ala Gly Phe Ala Ile Leu Lys Cys
210                 215                 220

Asn Asp Lys Lys Phe Asn Gly Thr Gly Pro Cys Thr Asn Val Ser Thr
225                 230                 235                 240

Val Gln Cys Thr His Gly Ile Arg Pro Val Val Ser Thr Gln Leu Leu
                245                 250                 255

Leu Asn Gly Ser Leu Ala Glu Glu Ile Val Ile Arg Ser Glu Asn
            260                 265                 270

Phe Thr Asn Asn Ala Lys Thr Ile Ile Val Gln Leu Asn Glu Ser Val
        275                 280                 285

Val Ile Asn Cys Thr Arg Pro Asn Asn Thr Arg Lys Ser Ile Asn
290                 295                 300

Ile Gly Pro Gly Arg Ala Leu Tyr Thr Thr Gly Glu Ile Ile Gly Asp
305                 310                 315                 320

Ile Arg Gln Ala His Cys Asn Leu Ser Lys Thr Gln Trp Glu Asn Thr
                325                 330                 335

Leu Glu Gln Ile Ala Ile Lys Leu Lys Glu Gln Phe Gly Asn Asn Lys
            340                 345                 350

Thr Ile Ile Phe Asn Pro Ser Ser Gly Gly Asp Pro Glu Ile Val Thr
        355                 360                 365

His Ser Phe Asn Cys Gly Gly Glu Phe Phe Tyr Cys Asn Ser Thr Gln
    370                 375                 380

Leu Phe Thr Trp Asn Asp Thr Arg Lys Leu Asn Asn Thr Gly Arg Asn
385                 390                 395                 400

Ile Thr Leu Pro Cys Arg Ile Lys Gln Ile Ile Asn Met Trp Gln Glu
                405                 410                 415
```

```
Val Gly Lys Ala Met Tyr Ala Pro Pro Ile Arg Gly Gln Ile Arg Cys
            420                 425                 430

Ser Ser Asn Ile Thr Gly Leu Leu Thr Arg Asp Gly Gly Lys Asp
            435                 440                 445

Thr Asn Gly Thr Glu Ile Phe Arg Pro Gly Gly Gly Asp Met Arg Asp
450                         455                 460

Asn Trp Arg Ser Glu Leu Tyr Lys Tyr Lys Val Val Lys Ile Glu Pro
465                 470                 475                 480

Leu Gly Val Ala Pro Thr Lys Ala Lys Arg Arg Val Val Gln Arg Glu
                485                 490                 495

Lys Arg Ala Val Gly Leu Gly Ala Leu Phe Leu Gly Phe Leu Gly Ala
                500                 505                 510

Ala Gly Ser Thr Met Gly Ala Ala Ser Ile Thr Leu Thr Val Gln Ala
            515                 520                 525

Arg Gln Leu Leu Ser Gly Ile Val Gln Gln Gln Asn Asn Leu Leu Arg
            530                 535                 540

Ala Ile Glu Ala Gln Gln His Leu Leu Gln Leu Thr Val Trp Gly Ile
545                 550                 555                 560

Lys Gln Leu Gln Ala Arg Val Leu Ala Val Glu Arg Tyr Leu Arg Asp
                565                 570                 575

Gln Gln Leu Leu Gly Ile Trp Gly Cys Ser Gly Lys Leu Ile Cys Thr
            580                 585                 590

Thr Thr Val Pro Trp Asn Thr Ser Trp Ser Asn Lys Ser Leu Asn Glu
            595                 600                 605

Ile Trp Asp Asn Met Thr Trp Met Lys Trp Glu Arg Glu Ile Asp Asn
610                 615                 620

Tyr Thr His Ile Ile Tyr Ser Leu Ile Glu Gln Ser Gln Asn Gln Gln
625                 630                 635                 640

Glu Lys Asn Glu Gln Glu Leu Leu Ala Leu Asp Lys Trp Ala Ser Leu
                645                 650                 655

Trp Asn Trp Phe Asp Ile Thr Lys Trp Leu Trp Tyr Ile Lys Ile Phe
                660                 665                 670

Ile Met Ile Val Gly Gly Leu Ile Gly Leu Arg Ile Val Phe Val Val
            675                 680                 685

Leu Ser Ile Val Asn Arg Val Arg Gln Gly Tyr Ser Pro Leu Ser Phe
690                 695                 700

Gln Thr His Leu Pro Ala Gln Arg Gly Pro Asp Arg Pro Asp Gly Ile
705                 710                 715                 720

Glu Glu Glu Gly Gly Glu Arg Asp Arg Asp Arg Ser Gly Pro Leu Val
                725                 730                 735

Asp Gly Phe Leu Ala Ile Ile Trp Val Asp Leu Arg Ser Leu Cys Leu
                740                 745                 750

Phe Ser Tyr His Arg Leu Arg Asp Leu Leu Leu Ile Val Thr Arg Ile
            755                 760                 765

Val Glu Leu Leu Gly Arg Arg Gly Trp Gly Val Leu Lys Tyr Trp Trp
            770                 775                 780

Asn Leu Leu Gln Tyr Trp Ile Gln Glu Leu Lys Asn Ser Ala Val Ser
785                 790                 795                 800

Leu Leu Asn Ala Thr Ala Ile Ala Val Ala Glu Gly Thr Asp Arg Val
                805                 810                 815

Ile Glu Ile Leu Gln Arg Ala Phe Arg Ala Val Leu His Ile Pro Val
                820                 825                 830

Arg Ile Arg Gln Gly Leu Glu Arg Ala Leu Leu
            835                 840
```

<210> SEQ ID NO 14
<211> LENGTH: 859
<212> TYPE: PRT
<213> ORGANISM: Human immunodeficiency virus type 2 (ST isolate)

<400> SEQUENCE: 14

Met Cys Gly Arg Asn Gln Leu Phe Val Ala Ser Leu Ala Ser Ala
1               5                   10                  15

Cys Leu Ile Tyr Cys Val Gln Tyr Val Thr Val Phe Tyr Gly Val Pro
            20                  25                  30

Val Trp Arg Asn Ala Ser Ile Pro Leu Phe Cys Ala Thr Lys Asn Arg
        35                  40                  45

Asp Thr Trp Gly Thr Ile Gln Cys Leu Pro Asp Asn Asp Asp Tyr Gln
    50                  55                  60

Glu Ile Ala Leu Asn Val Thr Glu Ala Phe Asp Ala Trp Asn Asn Thr
65                  70                  75                  80

Val Thr Glu Gln Ala Val Glu Asp Val Trp Ser Leu Phe Glu Thr Ser
                85                  90                  95

Ile Lys Pro Cys Val Lys Leu Thr Pro Leu Cys Val Ala Met Arg Cys
            100                 105                 110

Asn Ser Thr Thr Ala Lys Asn Thr Thr Ser Thr Pro Thr Thr Thr Thr
        115                 120                 125

Thr Ala Asn Thr Thr Ile Gly Glu Asn Ser Ser Cys Ile Arg Thr Asp
    130                 135                 140

Asn Cys Thr Gly Leu Gly Glu Glu Glu Met Val Asp Cys Gln Phe Asn
145                 150                 155                 160

Met Thr Gly Leu Glu Arg Asp Lys Lys Lys Leu Tyr Asn Glu Thr Trp
                165                 170                 175

Tyr Ser Lys Asp Val Val Cys Glu Ser Asn Asp Thr Lys Lys Glu Lys
            180                 185                 190

Thr Cys Tyr Met Asn His Cys Asn Thr Ser Val Ile Thr Glu Ser Cys
        195                 200                 205

Asp Lys His Tyr Trp Asp Thr Met Arg Phe Arg Tyr Cys Ala Pro Pro
    210                 215                 220

Gly Phe Ala Leu Leu Arg Cys Asn Asp Thr Asn Tyr Ser Gly Phe Glu
225                 230                 235                 240

Pro Asn Cys Ser Lys Val Val Ala Ala Thr Cys Thr Arg Met Met Glu
                245                 250                 255

Thr Gln Thr Ser Thr Trp Phe Gly Phe Asn Gly Thr Arg Ala Glu Asn
            260                 265                 270

Arg Thr Tyr Ile Tyr Trp His Gly Arg Asp Asn Arg Thr Ile Ile Ser
        275                 280                 285

Leu Asn Lys Phe Tyr Asn Leu Thr Val His Cys Lys Arg Pro Gly Asn
    290                 295                 300

Lys Thr Val Val Pro Ile Thr Leu Met Ser Gly Leu Val Phe His Ser
305                 310                 315                 320

Gln Pro Ile Asn Arg Arg Pro Arg Gln Ala Trp Cys Trp Phe Lys Gly
                325                 330                 335

Glu Trp Lys Glu Ala Met Lys Glu Val Lys Leu Thr Leu Ala Lys His
            340                 345                 350

Pro Arg Tyr Lys Gly Thr Asn Asp Thr Glu Lys Ile Arg Phe Ile Ala
        355                 360                 365

Pro Gly Glu Arg Ser Asp Pro Glu Val Ala Tyr Met Trp Thr Asn Cys
    370                 375                 380

```
Arg Gly Glu Phe Leu Tyr Cys Asn Met Thr Trp Phe Leu Asn Trp Val
385                 390                 395                 400

Glu Asn Arg Thr Asn Gln Thr Gln His Asn Tyr Val Pro Cys His Ile
            405                 410                 415

Lys Gln Ile Ile Asn Thr Trp His Lys Val Gly Lys Asn Val Tyr Leu
        420                 425                 430

Pro Pro Arg Glu Gly Gln Leu Thr Cys Asn Ser Thr Val Thr Ser Ile
            435                 440                 445

Ile Ala Asn Ile Asp Gly Gly Glu Asn Gln Thr Asn Ile Thr Phe Ser
        450                 455                 460

Ala Glu Val Ala Glu Leu Tyr Arg Leu Glu Leu Gly Asp Tyr Lys Leu
465                 470                 475                 480

Ile Glu Val Thr Pro Ile Gly Phe Ala Pro Thr Pro Val Lys Arg Tyr
            485                 490                 495

Ser Ser Ala Pro Val Arg Asn Lys Arg Gly Val Phe Val Leu Gly Phe
            500                 505                 510

Leu Gly Phe Leu Thr Thr Ala Gly Ala Ala Met Gly Ala Ala Ser Leu
        515                 520                 525

Thr Leu Ser Ala Gln Ser Arg Thr Leu Leu Ala Gly Ile Val Gln Gln
    530                 535                 540

Gln Gln Gln Leu Leu Asp Val Val Lys Arg Gln Gln Glu Met Leu Arg
545                 550                 555                 560

Leu Thr Val Trp Gly Thr Lys Asn Leu Gln Ala Arg Val Thr Ala Ile
            565                 570                 575

Glu Lys Tyr Leu Lys Asp Gln Ala Gln Leu Asn Ser Trp Gly Cys Ala
            580                 585                 590

Phe Arg Gln Val Cys His Thr Thr Val Pro Trp Val Asn Asp Thr Leu
        595                 600                 605

Thr Pro Asp Trp Asn Asn Met Thr Trp Gln Glu Trp Glu Gln Arg Ile
    610                 615                 620

Arg Asn Leu Glu Ala Asn Ile Ser Glu Ser Leu Glu Gln Ala Gln Ile
625                 630                 635                 640

Gln Gln Glu Lys Asn Met Tyr Glu Leu Gln Lys Leu Asn Ser Trp Asp
            645                 650                 655

Val Phe Gly Asn Trp Phe Asp Leu Thr Ser Trp Ile Lys Tyr Ile Gln
            660                 665                 670

Tyr Gly Val Tyr Ile Val Val Gly Ile Ile Val Leu Arg Ile Val Ile
        675                 680                 685

Tyr Val Val Gln Met Leu Ser Arg Leu Arg Lys Gly Tyr Arg Pro Val
690                 695                 700

Phe Ser Ser Pro Pro Ala Tyr Phe Gln Gln Ile His Ile His Lys Asp
705                 710                 715                 720

Arg Glu Gln Pro Ala Arg Glu Glu Thr Glu Glu Asp Val Gly Asn Ser
            725                 730                 735

Val Gly Asp Asn Trp Trp Pro Trp Pro Ile Arg Tyr Ile His Phe Leu
            740                 745                 750

Ile Arg Gln Leu Ile Arg Leu Leu Asn Arg Leu Tyr Asn Ile Cys Arg
        755                 760                 765

Asp Leu Leu Ser Arg Ser Phe Gln Thr Leu Gln Leu Ile Ser Gln Ser
    770                 775                 780

Leu Arg Arg Ala Leu Thr Ala Val Arg Asp Trp Leu Arg Phe Asn Thr
785                 790                 795                 800

Ala Tyr Leu Gln Tyr Gly Gly Glu Trp Ile Gln Glu Ala Phe Arg Ala
```

```
                    805                 810                 815
Phe Ala Arg Ala Thr Gly Glu Thr Leu Thr Asn Ala Trp Arg Gly Phe
                820                 825                 830

Trp Gly Thr Leu Gly Gln Ile Gly Arg Gly Ile Leu Ala Val Pro Arg
            835                 840                 845

Arg Ile Arg Gln Gly Ala Glu Ile Ala Leu Leu
        850                 855

<210> SEQ ID NO 15
<211> LENGTH: 6
<212> TYPE: PRT
<213> ORGANISM: Artificial Sequence
<220> FEATURE:
<223> OTHER INFORMATION: Oligonucleotide primer

<400> SEQUENCE: 15

Asn Trp Phe Asp Ile Thr
1               5

<210> SEQ ID NO 16
<211> LENGTH: 10
<212> TYPE: PRT
<213> ORGANISM: Artificial Sequence
<220> FEATURE:
<223> OTHER INFORMATION: Oligonucleotide primer

<400> SEQUENCE: 16

Glu Leu Leu Ala Leu Asp Lys Trp Ala Ser
1               5                   10

<210> SEQ ID NO 17
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 17
tagagccctg aagcatcca ggaag                                      25

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 18
ttgctacttg tgattgctcc atgt                                      24

<210> SEQ ID NO 19
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 19
gatcaagctt taggcatctc ctatggcagg aagaag                         36

<210> SEQ ID NO 20
<211> LENGTH: 33
<212> TYPE: DNA
<213> ORGANISM: Artificial Sequence
<220> FEATURE:
<223> OTHER INFORMATION: Oligonucleotide primer
```

<400> SEQUENCE: 20
agctggatcc gtctcgagat actgctccca ccc         33

<210> SEQ ID NO 21
<211> LENGTH: 2574
<212> TYPE: DNA
<213> ORGANISM: Human immunodeficiency virus type 2 isolate 7312a
<220> FEATURE:
<221> NAME/KEY: misc_feature
<222> LOCATION: (0)...(0)
<223> OTHER INFORMATION: gp120 envelope (GenBank Acc No. L36874)

<400> SEQUENCE: 21

```
atgtgtggta agaatctact atttgttgcc agcttgctag ctagtgctta cttaatatat      60
tgcaccaaat atgtgactgt tttctatggc gtgcccgtgt ggagaaatgc atccattccc     120
ctcttttgtg caactaagaa cagagatact tggggaacca tacagtgctt gccagacaat     180
gatgattatc aagaaatagc cctgaatgtg acagaggctt cgatgcatg gaataataca      240
gtaacagaac aggcagtaga agatgtctgg agtctatttg agacatcaat aaaaccatgc     300
gtcaaactaa caccttctatg tgtagcaatg agttgtaaca gcaccaccgc caccactaca   360
ccaccaagca ccactaacaa cacaaccaca acagagccca acaggagg gccagagata      420
aatgaaactt ttccatgcat gcgcacagac aactgcacag gattgggaga ggaagagatg    480
gtcgattgtc agttcaacat gacaggatta gagagagata agacaaaaca atatagtgaa    540
acatggtact caaagatgt agtttgtgag tcaaataacg ccagtgatgg gagagacaga    600
tgctacatga atcattgcaa cacatcagtc atcacagaat catgcgacaa gcactactgg    660
gatgctataa ggttagata ctgtgcacca ccgggttttg ctctgctaag atgtaatgac     720
accaactatt caggctttat gcccaactgt agtaaggtag tagtgtcctc ttgcacaaga    780
atgatggaaa cacagacctc tacatggttt ggcttcaatg gtacaaggc agaaaatagg     840
acatatatgt attggcatag taaagataat aggactatta aagcttgaa taagtattat     900
aatttaacaa tacattgtaa gaggccagga acaagacag ttgtaccaat aacactcatg     960
tcagggttag tgttccattc ccagcctatc aataaaagac ctaggcaagc atggtgctgg   1020
ttcaaaggcg agtggaggga agccatgcag gaggtgaaac aaaccccttat aaaacatccc   1080
aggtataaag gaaccaatga cacaaggaat attacctta caaaaccagg aacaggctca    1140
gacccagaag tggcatacat gtggactaac tgcagaggag aatttctcta ctgcaacatg   1200
acttggttcc tcaattgggt agaaaacaga acgggtcaga cacagcacaa ttatgcgccg   1260
tgccatataa acaaataat taatacctgg cacaaggtag aaaaaatgt gtatttgcct    1320
cctagggaag gacaattgac ctgcaactca acagtgacca gcttgattgc taacattgac   1380
gtagacgtag taataaccg gacaaatatt accttagtg cagaggtggc agaactgtac    1440
cgattagaat tgggagatta taattaata gaagtgcaca caattggttt cgcacctaca   1500
tcagaaaaaaa gatactcctc tactccgggg agacataaaa gaggtgtatt cgtgctaggg   1560
ttcttggggtt ttctcacgac agcaggagct gcaatgggcg cggcgtcctt gacgctgtcg   1620
gctcagtctc ggactttact ggccgggata gtgcagcaac agcaacagct gttagacgtg   1680
gtcaagagac aacaagaaat gttgcgactg accgtctggg gaacaaaaaa tctccaggca   1740
agagtcactg ctattgagaa atacttaaag gaccaggcgc aactaaattc atggggatgt   1800
gcgtttaggc aagtctgcca cactactgta ccatgggtaa atgacagctt gacacctgat   1860
tgggacaaca tgacgtggca acaatgggaa aaacaaatcc gcgacctgga ggcaaatatc   1920
```

-continued

```
agtgaaagtc tagaacaggc acaaatccag caagaaaaga acatgtatga attacaaaaa    1980
ttaaatagct gggatgtttt tggcaactgg tttgatttag cctcctgggt caaatatatt    2040
cagtatggag tttatatagt agtaggaata gtagctctca gagtaataat atatgtagta    2100
caaatgatag gtagacttag aagaggctat aggcctgttt tctcttcccc ccccggttac    2160
ttccaacaga tccgtatcca caaggaccag gaacagccag ccaacgaaga aacagaagaa    2220
ggaggtggaa acgacggggg ctacagatct tggccctggc agatcgaata catccacttc    2280
ctaattcgcc agctgaggaa cctcttgatt tggctatacg acggctgcag aaccttactg    2340
ttgaagacct tccaaacccct ccaaccagct ctccaaccac tcaggctcct gtttgcgtac    2400
ctccaatatg ggatcggctg gttccaagaa gcagtccaag cagcagcggg ggctacggga    2460
gagactcttg cgagcacagg gaggaccta tgggaggctc tcaggaggac ggcgagggga    2520
atcatcgcag tccccagaag aatcagacag gggcttgaac tcgccctcct gtga          2574
```

<210> SEQ ID NO 22
<211> LENGTH: 2670
<212> TYPE: DNA
<213> ORGANISM: Simian immunodeficiency virus SmPBJ1.9
<220> FEATURE:
<221> NAME/KEY: misc_feature
<222> LOCATION: (0)...(0)
<223> OTHER INFORMATION: gp120 envelope sequence

<400> SEQUENCE: 22

```
atgggatgtc ttgggaatca gctgcttatc gcgctcttgc tattaagtgc ttcagggatt      60
tattgtgttc aatatgtaac agtattctat ggtataccag catggaggaa tgcgacagtt     120
cccctcttct gtgcaaccaa ggatagggac acttggggaa caacacaatg cttgccagat     180
aatggtgatt gctcagaatt ggcaattaat gtcacagagg cttttgatgc ttgggataat     240
acagtcacag aacaagcaat agaggatgta tggaacctct tgaaacatc cattaagccc      300 tgtgtaaaac tcacccccact atgtataaca atgaggtgta ataaaagtga gacagacaga    360
tggggtttaa caggaacacc agcaccaaca acaacacaaa caacaacaac acaagcatca    420
acaacaccaa catcaccaat aacagcaaag gttgtaaatg acagtgatcc ttgtataaaa    480
attaataatt gtacaggctt ggaacaggag cccatggtaa gttgtaaatt taacatgaca    540
gggttaaaaa gagacaaaaa gagagaatat aatgaaacat ggtattcaag agatttagtt    600
tgtgaacaaa ataacaatga aactgacagt aaatgctata tgaaccattg taacaccagt    660
gttattcaag aatcctgtga caaacattat tgggatgcta ttagatttag atattgtgca    720
ccgccaggtt atgctttgct taggtgtaat gattcaaatt attcaggctt tgctcctaac    780
tgtactaagg tagtagttac ttcatgcaca agaatgatgg aaacacaaac ctctacttgg    840
tttggtttca atggtactag agcagaaaat agaacataca tttattggca tggcagaagc    900
aatagaacca taattagctt aaataagtat tataatctaa caatgagatg tagaagacca    960
ggaaataaga cagtcttacc agtcaccatt atgtcaggt tggtcttcca ttcgcaaccc   1020
ataaatgaga gaccaaaaca ggcctggtgc tggtttggag gagaatggaa aaaggccatc   1080
caggaagtga aggaaacctt ggtcaaacat cccaggtata cggaactaa taagactgaa   1140 caaattaagc taacagctcc aggaggagga gatccagaag ttactttcat gtggacaaat   1200
tgtcgaggag aattcttata ttgcaaaatg aattggtttc ttaattgggt agaagagata   1260
caaaatggtt ctagatggac aagtcaaaac cagaaagagc gacaaggag aaattatgtg   1320 ccatgtcata ttagacagat aatcaacacg tggcacaaag taggcaaaaa tgtgtatttg   1380
```

| | |
|---|---|
| cctcctaggg aaggagacct gacatgtaat tccactgtaa ctagcctcat agcagaaata | 1440 |
| gattggatca atggcaatga gaccaatatc accatgagtg cagaggtggc agaactgtat | 1500 |
| cgattggagt tgggagatta caaattagta gagattactc caattgcctt cgcccccaca | 1560 |
| agtgtaaaaa ggtacaccac aactggtgcc tcaagaaata aaagagpggt ctttgtgcta | 1620 |
| gggttcttgg gttttctcgc gacagcaggt tctgcaatgg gcgcggcgtc cgtgacgctg | 1680 |
| tcggctcagt cccggacttt gttggctggg atagtgcagc aacagcaaca gctgttggat | 1740 |
| gtggtcaaga gacaacaaga attgttgcga ctgaccgtct ggggagctaa gaacctccag | 1800 |
| actagagtca ctgctatcga gaagtaccta aaggatcagg cgcagctaaa ttcatgggga | 1860 |
| tgtgcttta ggcaggtctg ccacactact gtaccatggc caaatgacac attgacacct | 1920 |
| aactggaaca atatgacttg gcaagagtgg gaaaaacagg tgaacttcct agaggcaaat | 1980 |
| ataactcaat cattggaaga agcacaaatt cagcaagaaa agaatacgta tgaattgcaa | 2040 |
| aaattaaata gctgggatat ttttggcaat tggtttgacc ttacttcttg gataaaatat | 2100 |
| atacaatatg gtgtactgat agttctagga gtaataggat taagaatagt gatatatgta | 2160 |
| gtgcagatgt tagctaggtt aagacagggt tataggccag tgttctcttc ccctcccgct | 2220 |
| tatgttcagc agatccctat ccagacgggc caggaactgc aaccaaaga aggagaagaa | 2280 |
| ggagacggtg gaggcagagg tggcaacaga tcttggcctt ggcagataga atatattcat | 2340 |
| ttcctgatcc gccagttgat acgcctcttg acttggctat tcagcagttg cagagattgg | 2400 |
| ctattgagga actgccaaac cctccagcca gtgctccaga gcctctcaag gacgctgcag | 2460 |
| agagcccgtg aagtcatcag agttcagata gcctacctac agtatgggtg gcgttacctc | 2520 |
| caagaagcag cgcaggcgtg gtggaaattt gtacgagaga ctcttgcaag gcgtggagga | 2580 |
| gacttatggg agactctggg aagggttgga aggggaatac tcgcaatccc aagacgcatc | 2640 |
| aggcaagggc ttgagctcac tctcttgtga | 2670 |

<210> SEQ ID NO 23
<211> LENGTH: 2307
<212> TYPE: DNA
<213> ORGANISM: Simian immunodeficiency virus agmVer155
<220> FEATURE:
<221> NAME/KEY: misc_feature
<222> LOCATION: (0)...(0)
<223> OTHER INFORMATION: gp120 envelope (GenBank Acc. No. M29975)

<400> SEQUENCE: 23

| | |
|---|---|
| atgacaaagt tcttaggaat ttttatagta ttaggaatag ggataggaat agggataagt | 60 |
| acaaaacagc agtggataac agtgttctat ggagtaccag tatggaaaaa cagctcagtc | 120 |
| caagcttttt gcatgacacc tactactagg ttgtgggcaa ctactaattg cataccagat | 180 |
| gatcatgact atacagaagt accactgaat ataacagagc catttgaagc atgggcagac | 240 |
| agaaatccct tagtagcaca agcaggaagt aacattcacc tgctgtttga acagacatta | 300 |
| aagccctgtg taaagctatc acctctatgt atcaaaatga attgtgtaga gttaaaaggc | 360 |
| tccgcaacct ctaccccagc aacctctact acggcaggaa ccaaactacc ctgtgttaga | 420 |
| aataaaacag actccaacct acagtcatgc aacgacacca tcatagaaaa ggagatgaat | 480 |
| gacgaggcag cgtcaaactg cacctttgct atggctgggt acattaggga ccaaaagaag | 540 |
| aattactcag tagtatggaa tgatgcagaa atcttttgta agcgtagtac atcgcataat | 600 |
| gggacaaaag agtgctatat gatccactgt aatgattcag ttataaagga agcttgtgat | 660 |
| aagacatatt gggatgaatt aagactaaga tattgtgctc cagcaggata cgctttgctt | 720 |

| | |
|---|---|
| aaatgtaatg attgggatta tgcaggattt aagccagaat gttctaatgt ttcagtagtg | 780 |
| cattgcacaa ctttaatgaa tacaacagta accactggtc tgttattgaa tggaagctat | 840 |
| tcagaaaatc gaacccagat ctggcaaaaa catggagtga gcaatgactc agtgttaatc | 900 |
| ttgctcaata agcattataa cctgacagtt acatgcaaaa ggccagggaa taagacagtc | 960 |
| ttgccagtaa cgataatggc aggattagtc ttccactcac agaagtataa tacaagacta | 1020 |
| aggcaggcct ggtgccactt ccagggcaat tggaaaggag cttggaagga agtacaagag | 1080 |
| gaaatagtaa aattaccaaa agaacggtac caaggcacca atgatacaaa caaaatcttt | 1140 |
| ttgcaaagac aatttggaga cccagaagca gcaaatctat ggttcaactg tcaaggggaa | 1200 |
| ttcttctact gtaaaatgga ctggttttta aattatctga ataatttaac agtggatgct | 1260 |
| gatcataatc attgtaaaaa caacgcaggg aaaggtcgaa gtccaggtcc ctgtgtacag | 1320 |
| agaacttatg ttgcctgcca tatccgatct gtcataaatg attggtatac tatatcaaag | 1380 |
| aaaacatatg ctccaccaag agaaggacat ttgcagtgca cgtccacagt tactgggatg | 1440 |
| acagtagagc taaactataa taaccagaac aggacaaatg taacattgag tccccagata | 1500 |
| gaaaccatct gggcggcaga attgggcaga tacaaattgg tagagattac accaattgga | 1560 |
| tttgcaccca cagaagtcag gcgatacacg ggaggccaag agaggcaaaa acgagtcccg | 1620 |
| ttcgtgctag ggttcctagg cttcttggga gctgctggga ctgcaatggg agcagcggcg | 1680 |
| acagccctga cggtccagtc tcagcattta cttgctggga tattgcagca gcagaagaat | 1740 |
| ctgctggcgg ctgtgggagc tcaacagcag atgttgaagc tgaccatttg gggtgtgaaa | 1800 |
| aacctcaatg cccgcgtcac agctcttgag aagtacctgg cggatcaggc acggttaaac | 1860 |
| gcttgggggt gcgcgtggaa acaagtatgt catacaacag taccctggac gtggaataat | 1920 |
| acaccagagt ggaataatat gacctggttg gagtgggaaa acagataga aggattggag | 1980 |
| ggcaacataa caaacaatt ggaacaggca agggaacaag aggaaaagaa tttggatgct | 2040 |
| tatcaaaagt tgtcagactg gtcgagtttt tggtcttggt tcgattttc aaaatggctg | 2100 |
| aacattttaa agataggctt tttggcagta ataggcgtta tagggttaag attgctttac | 2160 |
| acattatata cttgcatagc tagggttagg cagggttact ctcctttatc tcctcagatc | 2220 |
| catatccatc cgtggaaggg acagccagac aacgcaggag agccagaaga aggtggaaga | 2280 |
| acaggcaaaa gcaaatctac gcattag | 2307 |

<210> SEQ ID NO 24
<211> LENGTH: 2640
<212> TYPE: DNA
<213> ORGANISM: Simian immunodeficiency virus agm TAN1
<220> FEATURE:
<221> NAME/KEY: misc_feature
<222> LOCATION: (0)...(0)
<223> OTHER INFORMATION: gp120 envelope (GenBank Acc. No. U58991)

<400> SEQUENCE: 24

| | |
|---|---|
| atgggaccat taaggggaaa aggggtatta ttagtaattt tgggattaag cttaatagga | 60 |
| ctgttatatg ggacacagta tattacagtg ttttatggta tcccagtatg gaaaaacagc | 120 |
| tcagtgcaag ctttctgtat gacacctaat accaaccttt gggcaacaac taattgtata | 180 |
| ccagatgatc atgattatac tgaagtacag ttaaatgtct ctgagaaatt tgaagcatgg | 240 |
| aaggacagga atccattagt ggcacaggcg gagagtaaca tacatttgct ctttgaaagc | 300 |
| actctgaagc catgcgtaaa actgacacct atgtgcataa agatgaattg tactaaatta | 360 |
| acaagtaccg cccctacatc aagtacccct acatcaagca gcactacgga tccctgtcca | 420 |

```
aataccgacg aaagtagctg taacgccacc ttagttacaa atagcatgga ttatgagaat    480
agttctatat gctcctttgc tatggcagga tataggagag atgtaaaaaa gaaatataat    540
agtacttggt atgatcagga gttggtatgt gagaaggaaa acaacaccac aggcacgaga    600
ggttgttaca tgattcactg caacgactct gtaataaaag aagcttgtga gaaaacttat    660
tgggatacct taagattaag atactgtgca ccagcaggct ttgctatctt aaaatgtaag    720
gatactaatt atacaggatt tggtgtttgt agaaatgttt cagtagttag ttgtactgga    780
ttgatgaata ctacagtgag ctcagcattt ggcataaatg gcagtcaggc agaaaacaga    840
acagaaatat ggcaaaagca tggagtgagc aataattctg tgataataaa actaaataaa    900
cattataagt tgaagatagt gtgtagaaga ccaggaaata agacagtctt accagtaacc    960
atcatggcag gtctcgtgtt ccactcacaa caatataata caaaattaag acaagcatgg   1020
tgccatttcc agggtgattg gaaaggagcc tggagggaag tgagaaaaac aatagtggag   1080
cttccaaaag agaaatatcg agggacaaat aacacaaggc agatttggct aagtagacaa   1140
tggggagatc cagaagcagc taacatttgg ctcaattgcc aaggagagtt tttctattgt   1200
actcctgatt ggtttgttaa ttggctgaat aatgagtcta atagtggaag aaatgtagat   1260
gtagaaggta ataattgcac cactggaaag gataaacgct gctacaaaag gacatatgtc   1320
ccctgccata ttaggtcaat tgtcaatgac tggtacacgc tcagtaagaa aacctatgca   1380
ccaccaaggg aaggacactt agaatgcaca tcaacagtga catctatgat ggtatcactg   1440
gattataaca gcaaagaaag gactaatgtg acattgacag ctaatttgga gaacatatgg   1500
gcttatgaat tgggaagata taagctcata gaaattgaac caatcggttt cgcgccaaca   1560
gagataagaa gatatgttgg gccaactcga gaaaagaggg tgcccttcgt gttgggggttc  1620 ctaggctttt tgggggcagc tggagctgca atgggtgcaa cagcgacagc gttgacggtc   1680
cagtcccagc aattacttgc agggatattg cagcagcaga agaatctgct ggcggcagtt   1740
gagcagcagc agcagatgct aaagctcacc atttggggtg tgaaaaacct caatgcccgc   1800
gtcactgccc ttgaaaaata cctagaggat cagacacggc taaatttgtg gggatgtgca   1860
ttcaaacagg tgtgtcacac tacggtgccg tggactttca acaatacacc agactgggac   1920
aatatgacct ggcaggaatg ggagagccaa ataactgcct tggaaggaaa tattagtact   1980
actcttgtca agcatatga gcaagagcag aaaaatatgg atacttatca aaagttaggt   2040
gattggactt cttggtggaa catctttgac gtctcatcat ggttctggtg gattaaatgg   2100
ggattttata tagtaatagg acttatattg tttaggatgg cttggcttat ttggggatgc   2160
atagctaggg ttaggcaggg ttactttcct ttgtctcctc agatcaatat ccgcctgggg   2220
agggaacagc cagacaacgc aggaggagaa gacaaagatt ccagcagcag cagagacaag   2280
tcgccgccct cagtgaaaga atctttattg cccaacagag gagggatcca agcggaggag   2340
agagcttggc ggcagcattt gaccaattgg tgcttgacaa tcagcagttg gttattgaga   2400
ctttaccaga tcctccgcag gagcctcacg actcttcttc aactgcttag acaggagtgc   2460
caatacattc agtatgggtg gcagcaattc aaagagggag cagcaaggtc tttttgaggct  2520 ttggcgagcg ctgcgcaaag cgccagtcgt acgctatgga atgcttgcag atccgcttat   2580
cgggcaatcc tcgaacatcc aagaagaatg cgacaagaac tggaacggtg gttcaactag   2640
```

<210> SEQ ID NO 25
<211> LENGTH: 1032
<212> TYPE: DNA
<213> ORGANISM: Human Immunodeficiency Virus Type 2 7312A

```
<220> FEATURE:
<221> NAME/KEY: misc_feature
<222> LOCATION: (0)...(0)
<223> OTHER INFORMATION: gp41 from HIV-2 7

```
Leu Asn Ser Trp Gly Cys Ala Phe Arg Gln Val Cys His Thr Thr Val
                85                  90                  95 cca tgg gta aat gac agc ttg aca cct gat tgg gac aac atg acg tgg       336
Pro Trp Val Asn Asp Ser Leu Thr Pro Asp Trp Asp Asn Met Thr Trp
            100                 105                 110 caa caa tgg gaa aaa caa atc cgc gac ctg gag gca aat atc agt gaa       384
Gln Gln Trp Glu Lys Gln Ile Arg Asp Leu Glu Ala Asn Ile Ser Glu
            115                 120                 125 agt cta gaa cag gca caa atc cag caa gaa aag aac atg tat gaa tta       432
Ser Leu Glu Gln Ala Gln Ile Gln Gln Glu Lys Asn Met Tyr Glu Leu
130             135                 140 ttg gca tta gat aaa tgg gca agt ttg tgg aat tgg ttt gac ata aca       480
Leu Ala Leu Asp Lys Trp Ala Ser Leu Trp Asn Trp Phe Asp Ile Thr
145             150                 155                 160 aaa tgg ctg tgg tat ata aaa tat ggc gtc tat ata gta gta gga ata       528
Lys Trp Leu Trp Tyr Ile Lys Tyr Gly Val Tyr Ile Val Val Gly Ile
                165                 170                 175 gta gct ctc aga gta ata ata tat gta gta caa atg ata ggt aga ctt       576
Val Ala Leu Arg Val Ile Ile Tyr Val Val Gln Met Ile Gly Arg Leu
            180                 185                 190 aga aga ggc tat agg cct gtt ttc tct tcc ccc ccc ggt tac ttc caa       624
Arg Arg Gly Tyr Arg Pro Val Phe Ser Ser Pro Pro Gly Tyr Phe Gln
            195                 200                 205 cag atc cgt atc cac aag gac cag gaa cag cca gcc aac gaa gaa aca       672
Gln Ile Arg Ile His Lys Asp Gln Glu Gln Pro Ala Asn Glu Glu Thr
            210                 215                 220 gaa gaa gga ggt gga aac gac ggg ggc tac aga tct tgg ccc tgg cag       720
Glu Glu Gly Gly Gly Asn Asp Gly Gly Tyr Arg Ser Trp Pro Trp Gln
225             230                 235                 240 atc gaa tac atc cac ttc cta att cgc cag ctg agg aac ctc ttg att       768
Ile Glu Tyr Ile His Phe Leu Ile Arg Gln Leu Arg Asn Leu Leu Ile
                245                 250                 255 tgg cta tac gac ggc tgc aga acc tta ctg ttg aag acc ttc caa acc       816
Trp Leu Tyr Asp Gly Cys Arg Thr Leu Leu Leu Lys Thr Phe Gln Thr
            260                 265                 270 ctc caa cca gct ctc caa cca ctc agg ctc ctg ttt gcg tac ctc caa       864
Leu Gln Pro Ala Leu Gln Pro Leu Arg Leu Leu Phe Ala Tyr Leu Gln
            275                 280                 285 tat ggg atc ggc tgg ttc caa gaa gca gtc caa gca gca gcg ggg gct       912
Tyr Gly Ile Gly Trp Phe Gln Glu Ala Val Gln Ala Ala Ala Gly Ala
290             295                 300 acg gga gag act ctt gcg agc aca ggg agg acc tta tgg gag gct ctc       960
Thr Gly Glu Thr Leu Ala Ser Thr Gly Arg Thr Leu Trp Glu Ala Leu
305             310                 315                 320 agg agg acg gcg agg gga atc atc gca gtc ccc aga aga atc aga cag      1008
Arg Arg Thr Ala Arg Gly Ile Ile Ala Val Pro Arg Arg Ile Arg Gln
                325                 330                 335 ggg ctt gaa ctc gcc ctc ctg tga                                      1032
Gly Leu Glu Leu Ala Leu Leu  *
            340
```

<210> SEQ ID NO 27
<211> LENGTH: 343
<212> TYPE: PRT
<213> ORGANISM: Artificial Sequence
<220> FEATURE:
<223> OTHER INFORMATION: chimeric polypeptide comprising gp41 from HIV-2 7312A and a heterologous MPER epitope from HIV-1 (construct C1 of Figure 11)

<400> SEQUENCE: 27

Gly

|  | 1 |  |  | 5 |  |  |  |  | 10 |  |  |  |  | 15 |  |
|---|---|---|---|---|---|---|---|---|---|---|---|---|---|---|---|
| Ala | Met | Gly | Ala | Ala | Ser | Leu | Thr | Leu | Ser | Ala | Gln | Ser | Arg | Thr | Leu |
|  |  |  | 20 |  |  |  |  | 25 |  |  |  |  | 30 |  |  |

Leu Ala Gly Ile Val Gln Gln Gln Gln Leu Leu Asp Val Val Lys
            35                40                45

Arg Gln Gln Glu Met Leu Arg Leu Thr Val Trp Gly Thr Lys Asn Leu
 50               55               60

Gln Ala Arg Val Thr Ala Ile Glu Lys Tyr Leu Lys Asp Gln Ala Gln
 65               70               75               80

Leu Asn Ser Trp Gly Cys Ala Phe Arg Gln Val Cys His Thr Val
                85               90               95

Pro Trp Val Asn Asp Ser Leu Thr Pro Asp Trp Asp Asn Met Thr Trp
            100              105              110

Gln Gln Trp Glu Lys Gln Ile Arg Asp Leu Glu Ala Asn Ile Ser Glu
            115              120              125

Ser Leu Glu Gln Ala Gln Ile Gln Gln Glu Lys Asn Met Tyr Glu Leu
    130              135              140

Leu Ala Leu Asp Lys Trp Ala Ser Leu Trp Asn Trp Phe Asp Ile Thr
145              150              155              160

Lys Trp Leu Trp Tyr Ile Lys Tyr Gly Val Tyr Ile Val Gly Ile
                165              170              175

Val Ala Leu Arg Val Ile Ile Tyr Val Val Gln Met Ile Gly Arg Leu
            180              185              190

Arg Arg Gly Tyr Arg Pro Val Phe Ser Ser Pro Gly Tyr Phe Gln
                195              200              205

Gln Ile Arg Ile His Lys Asp Gln Glu Gln Pro Ala Asn Glu Glu Thr
    210              215              220

Glu Glu Gly Gly Gly Asn Asp Gly Gly Tyr Arg Ser Trp Pro Trp Gln
225              230              235              240

Ile Glu Tyr Ile His Phe Leu Ile Arg Gln Leu Arg Asn Leu Leu Ile
                245              250              255

Trp Leu Tyr Asp Gly Cys Arg Thr Leu Leu Lys Thr Phe Gln Thr
            260              265              270

Leu Gln Pro Ala Leu Gln Pro Leu Arg Leu Leu Phe Ala Tyr Leu Gln
    275              280              285

Tyr Gly Ile Gly Trp Phe Gln Glu Ala Val Gln Ala Ala Gly Ala
    290              295              300

Thr Gly Glu Thr Leu Ala Ser Thr Gly Arg Thr Leu Trp Glu Ala Leu
305              310              315              320

Arg Arg Thr Ala Arg Gly Ile Ile Ala Val Pro Arg Arg Ile Arg Gln
            325              330              335

Gly Leu Glu Leu Ala Leu Leu
            340

```
<210> SEQ ID NO 28
<211> LENGTH: 1032
<212> TYPE: DNA
<213> ORGANISM: Artificial Sequence
<220> FEATURE:
<223> OTHER INFORMATION: chimeric polynucleotide comprising the
      nucleotide sequence encoding gp41 from HIV-2 7312A and a
      heterologous MPER epitope from HIV-1 (construct C2
      of Figure 11)
<220> FEATURE:
<221> NAME/KEY: CDS
<222> LOCATION: (1)...(1032)

<400> SEQUENCE: 28
```

| | | |
|---|---|---|
| ggt gta ttc gtg cta ggg ttc ttg ggt ttt ctc acg aca gca gga gct<br>Gly Val Phe Val Leu Gly Phe Leu Gly Phe Leu Thr Thr Ala Gly Ala<br>1               5                   10                  15 | | 48 |
| gca atg ggc gcg gcg tcc ttg acg ctg tcg gct cag tct cgg act tta<br>Ala Met Gly Ala Ala Ser Leu Thr Leu Ser Ala Gln Ser Arg Thr Leu<br>            20                  25                  30 | | 96 |
| ctg gcc ggg ata gtg cag caa cag caa cag ctg tta gac gtg gtc aag<br>Leu Ala Gly Ile Val Gln Gln Gln Gln Gln Leu Leu Asp Val Val Lys<br>        35                  40                  45 | | 144 |
| aga caa caa gaa atg ttg cga ctg acc gtc tgg gga aca aaa aat ctc<br>Arg Gln Gln Glu Met Leu Arg Leu Thr Val Trp Gly Thr Lys Asn Leu<br>50                  55                  60 | | 192 |
| cag gca aga gtc act gct att gag aaa tac tta aag gac cag gcg caa<br>Gln Ala Arg Val Thr Ala Ile Glu Lys Tyr Leu Lys Asp Gln Ala Gln<br>65                  70                  75                  80 | | 240 |
| cta aat tca tgg gga tgt gcg ttt agg caa gtc tgc cac act act gta<br>Leu Asn Ser Trp Gly Cys Ala Phe Arg Gln Val Cys His Thr Thr Val<br>                85                  90                  95 | | 288 |
| cca tgg gta aat gac agc ttg aca cct gat tgg gac aac atg acg tgg<br>Pro Trp Val Asn Asp Ser Leu Thr Pro Asp Trp Asp Asn Met Thr Trp<br>            100                 105                 110 | | 336 |
| caa caa tgg gaa aaa caa atc cgc gac ctg gag gca aat atc agt gaa<br>Gln Gln Trp Glu Lys Gln Ile Arg Asp Leu Glu Ala Asn Ile Ser Glu<br>        115                 120                 125 | | 384 |
| agt cta gaa cag gca caa atc cag caa gaa aag aac atg tat gaa tta<br>Ser Leu Glu Gln Ala Gln Ile Gln Gln Glu Lys Asn Met Tyr Glu Leu<br>    130                 135                 140 | | 432 |
| caa gca tta gat aaa tgg gca agt ttg tgg aat tgg ttt gac ata aca<br>Gln Ala Leu Asp Lys Trp Ala Ser Leu Trp Asn Trp Phe Asp Ile Thr<br>145                 150                 155                 160 | | 480 |
| aaa tgg ctg tgg tat ata aaa tat ggc gtc tat ata gta gta gga ata<br>Lys Trp Leu Trp Tyr Ile Lys Tyr Gly Val Tyr Ile Val Val Gly Ile<br>                165                 170                 175 | | 528 |
| gta gct ctc aga gta ata ata tat gta gta caa atg ata ggt aga ctt<br>Val Ala Leu Arg Val Ile Ile Tyr Val Val Gln Met Ile Gly Arg Leu<br>            180                 185                 190 | | 576 |
| aga aga ggc tat agg cct gtt ttc tct tcc ccc ccc ggt tac ttc caa<br>Arg Arg Gly Tyr Arg Pro Val Phe Ser Ser Pro Pro Gly Tyr Phe Gln<br>        195                 200                 205 | | 624 |
| cag atc cgt atc cac aag gac cag gaa cag cca gcc aac gaa gaa aca<br>Gln Ile Arg Ile His Lys Asp Gln Glu Gln Pro Ala Asn Glu Glu Thr<br>    210                 215                 220 | | 672 |
| gaa gaa gga ggt gga aac gac ggg ggc tac aga tct tgg ccc tgg cag<br>Glu Glu Gly Gly Gly Asn Asp Gly Gly Tyr Arg Ser Trp Pro Trp Gln<br>225                 230                 235                 240 | | 720 |
| atc gaa tac atc cac ttc cta att cgc cag ctg agg aac ctc ttg att<br>Ile Glu Tyr Ile His Phe Leu Ile Arg Gln Leu Arg Asn Leu Leu Ile<br>                245                 250                 255 | | 768 |
| tgg cta tac gac ggc tgc aga acc tta ctg ttg aag acc ttc caa acc<br>Trp Leu Tyr Asp Gly Cys Arg Thr Leu Leu Leu Lys Thr Phe Gln Thr<br>            260                 265                 270 | | 816 |
| ctc caa cca gct ctc caa cca ctc agg ctc ctg ttt gcg tac ctc caa<br>Leu Gln Pro Ala Leu Gln Pro Leu Arg Leu Leu Phe Ala Tyr Leu Gln<br>        275                 280                 285 | | 864 |
| tat ggg atc ggc tgg ttc caa gaa gca gtc caa gca gca gcg ggg gct<br>Tyr Gly Ile Gly Trp Phe Gln Glu Ala Val Gln Ala Ala Ala Gly Ala<br>    290                 295                 300 | | 912 |
| acg gga gag act ctt gcg agc aca ggg agg acc tta tgg gag gct ctc<br>Thr Gly Glu Thr Leu Ala Ser Thr Gly Arg Thr Leu Trp Glu Ala Leu<br>305                 310                 315                 320 | | 960 |

```
                                                              -continued agg agg acg gcg agg gga atc atc gca gtc ccc aga aga atc aga cag       1008
Arg Arg Thr Ala Arg Gly Ile Ile Ala Val Pro Arg Arg Ile Arg Gln
            325                 330                 335 ggg ctt gaa ctc gcc ctc ctg tga                                       1032
Gly Leu Glu Leu Ala Leu Leu  *
340

<210> SEQ ID NO 29
<211> LENGTH: 343
<212> TYPE: PRT
<213> ORGANISM: Artificial Sequence
<220> FEATURE:
<223> OTHER INFORMATION: chimeric polypeptide encoding gp41 from HIV-2
      7312A and a heterologous MPER epitope from HIV-1
      (construct C2 of Figure 11)

<400> SEQUENCE: 29

Gly Val Phe Val Leu Gly Phe Leu Gly Phe Leu Thr Thr Ala Gly Ala
 1               5                  10                  15

Ala Met Gly Ala Ala Ser Leu Thr Leu Ser Ala Gln Ser Arg Thr Leu
            20                  25                  30

Leu Ala Gly Ile Val Gln Gln Gln Gln Leu Leu Asp Val Val Lys
        35                  40                  45

Arg Gln Gln Glu Met Leu Arg Leu Thr Val Trp Gly Thr Lys Asn Leu
 50                  55                  60

Gln Ala Arg Val Thr Ala Ile Glu Lys Tyr Leu Lys Asp Gln Ala Gln
65                  70                  75                  80

Leu Asn Ser Tr

```
Arg Arg Thr Ala Arg Gly Ile Ile Ala Val Pro Arg Arg Ile Arg Gln
            325                 330                 335
Gly Leu Glu Leu Ala Leu Leu
        340

<210> SEQ ID NO 30
<211> LENGTH: 1032
<212> TYPE: DNA
<213> ORGANISM: Artificial Sequence
<220> FEATURE:
<223> OTHER INFORMATION: chimeric polynucleotide comprising the
      nucleotide sequence encoding gp41 from HIV-2 7312A and a
      heterologous MPER epitope from HIV-1 (construct C3
      of Figure 11)
<220> FEATURE:
<221> NAME/KEY: CDS
<222> LOCATION: (1)...(1032)

<400> SEQUENCE: 30 ggt gta ttc gtg cta ggg ttc ttg ggt ttt ctc acg aca gca gga gct      48
Gly Val Phe Val Leu Gly Phe Leu Gly Phe Leu Thr Thr Ala Gly Ala
 1               5                  10                  15 gca atg ggc gcg gcg tcc ttg acg ctg tcg gct cag tct cgg act tta      96
Ala Met Gly Ala Ala Ser Leu Thr Leu Ser Ala Gln Ser Arg Thr Leu
            20                  25                  30 ctg gcc ggg ata gtg cag caa cag caa cag ctg tta gac gtg gtc aag     144
Leu Ala Gly Ile Val Gln Gln Gln Gln Gln Leu Leu Asp Val Val Lys
        35                  40                  45 aga caa caa gaa atg ttg cga ctg acc gtc tgg gga aca aaa aat ctc     192
Arg Gln Gln Glu Met Leu Arg Leu Thr Val Trp Gly Thr Lys Asn Leu
    50                  55                  60 cag gca aga gtc act gct att gag aaa tac tta aag gac cag gcg caa     240
Gln Ala Arg Val Thr Ala Ile Glu Lys Tyr Leu Lys Asp Gln Ala Gln
65                  70                  75                  80 cta aat tca tgg gga tgt gcg ttt agg caa gtc tgc cac act act gta     288
Leu Asn Ser Trp Gly Cys Ala Phe Arg Gln Val Cys His Thr Thr Val
                85                  90                  95 cca tgg gta aat gac agc ttg aca cct gat tgg gac aac atg acg tgg     336
Pro Trp Val Asn Asp Ser Leu Thr Pro Asp Trp Asp Asn Met Thr Trp
            100                 105                 110 caa caa tgg gaa aaa caa atc cgc gac ctg gag gca aat atc agt gaa     384
Gln Gln Trp Glu Lys Gln Ile Arg Asp Leu Glu Ala Asn Ile Ser Glu
        115                 120                 125 agt cta gaa cag gca caa atc cag caa gaa aag aac atg tat gaa tta     432
Ser Leu Glu Gln Ala Gln Ile Gln Gln Glu Lys Asn Met Tyr Glu Leu
    130                 135                 140 caa gca tta gat aaa tgg gca agt ttg tgg aat tgg ttt gac ata aca     480
Gln Ala Leu Asp Lys Trp Ala Ser Leu Trp Asn Trp Phe Asp Ile Thr
145                 150                 155                 160 aaa tgg ctg tgg tat ata aaa tat ggc gtc tat ata gta gta gga ata     528
Lys Trp Leu Trp Tyr Ile Lys Tyr Gly Val Tyr Ile Val Val Gly Ile
                165                 170                 175 gta gct ctc aga gta ata ata tat gta gta caa atg ata ggt aga ctt     576
Val Ala Leu Arg Val Ile Ile Tyr Val Val Gln Met Ile Gly Arg Leu
            180                 185                 190 aga aga ggc tat agg cct gtt ttc tct tcc ccc ccc ggt tac ttc caa     624
Arg Arg Gly Tyr Arg Pro Val Phe Ser Ser Pro Pro Gly Tyr Phe Gln
        195                 200                 205 cag atc cgt atc cac aag gac cag gaa cag cca gcc aac gaa gaa aca     672
Gln Ile Arg Ile His Lys Asp Gln Glu Gln Pro Ala Asn Glu Glu Thr
    210                 215                 220 gaa gaa gga ggt gga aac gac ggg ggc tac aga tct tgg ccc tgg cag     720
Glu Glu Gly Gly Gly Asn Asp Gly Gly Tyr Arg Ser Trp Pro Trp Gln
```

```
Glu Glu Gly Gly Gly Asn Asp Gly Gly Tyr Arg Ser Trp Pro Trp Gln
225                 230                 235                 240 atc gaa tac atc cac ttc cta att cgc cag ctg agg aac ctc ttg att       768
Ile Glu Tyr Ile His Phe Leu Ile Arg Gln Leu Arg Asn Leu Leu Ile
            245                 250                 255 tgg cta tac gac ggc tgc aga acc tta ctg ttg aag acc ttc caa acc       816
Trp Leu Tyr Asp Gly Cys Arg Thr Leu Leu Leu Lys Thr Phe Gln Thr
                260                 265                 270 ctc caa cca gct ctc caa cca ctc agg ctc ctg ttt gcg tac ctc caa       864
Leu Gln Pro Ala Leu Gln Pro Leu Arg Leu Leu Phe Ala Tyr Leu Gln
            275                 280                 285 tat ggg atc ggc tgg ttc caa gaa gca gtc caa gca gca gcg ggg gct       912
Tyr Gly Ile Gly Trp Phe Gln Glu Ala Val Gln Ala Ala Ala Gly Ala
        290                 295                 300 acg gga gag act ctt gcg agc aca ggg agg acc tta tgg gag gct ctc       960
Thr Gly Glu Thr Leu Ala Ser Thr Gly Arg Thr Leu Trp Glu Ala Leu
305                 310                 315                 320 agg agg acg gcg agg gga atc atc gca gtc ccc aga aga atc aga cag      1008
Arg Arg Thr Ala Arg Gly Ile Ile Ala Val Pro Arg Arg Ile Arg Gln
                325                 330                 335 ggg ctt gaa ctc gcc ctc ctg tga                                      1032
Gly Leu Glu Leu Ala Leu Leu *
            340

<210> SEQ ID NO 31
<211> LENGTH: 343
<212> TYPE: PRT
<213> ORGANISM: Artificial Sequence
<220> FEATURE:
<223> OTHER INFORMATION: chimeric polypeptide encoding gp41 from HIV-2
      7312A and a heterologous MPER epitope from HIV-1
      (construct C3 of Figure 11)

<400> SEQUENCE: 31

Gly Val Phe Val Leu Gly Phe Leu Gly Phe Leu Thr Thr Ala Gly Ala
1               5                   10                  15

Ala Met Gly Ala Ala Ser Leu Thr Leu Ser Ala Gln Ser Arg Thr Leu
            20                  25                  30

Leu Ala Gly Ile Val Gln Gln Gln Gln Leu Leu Asp Val Val Lys
        35                  40                  45

Arg Gln Gln Glu Met Leu Arg Leu Thr Val Trp Gly Thr Lys Asn Leu
50                  55                  60

Gln Ala Arg Val Thr Ala Ile Glu Lys Tyr Leu Lys Asp Gln Ala Gln
65                  70                  75                  80

Leu Asn Ser Trp Gly Cys Ala Phe Arg Gln Val Cys His Thr Thr Val
            85                  90                  95

Pro Trp Val Asn Asp Ser Leu Thr Pro Asp Trp Asp Asn Met Thr Trp
        100                 105                 110

Gln Gln Trp Glu Lys Gln Ile Arg Asp Leu Glu Ala Asn Ile Ser Glu
    115                 120                 125

Ser Leu Glu Gln Ala Gln Ile Gln Gln Glu Lys Asn Met Tyr Glu Leu
        130                 135                 140

Leu Ala Leu Asp Lys Trp Ala Ser Leu Trp Asn Trp Phe Asp Leu Ala
145                 150                 155                 160

Ser Trp Val Lys Tyr Ile Gln Tyr Gly Val Tyr Ile Val Val Gly Ile
            165                 170                 175

Val Ala Leu Arg Val Ile Ile Tyr Val Val Gln Met Ile Gly Arg Leu
        180                 185                 190

Arg Arg Gly Tyr Arg Pro Val Phe Ser Ser Pro Pro Gly Tyr Phe Gln
```

```
                        195                 200                 205
Gln Ile Arg Ile His Lys Asp Gln Glu Gln Pro Ala Asn Glu Glu Thr
    210                 215                 220

Glu Glu Gly Gly Gly Asn Asp Gly Gly Tyr Arg Ser Trp Pro Trp Gln
225                 230                 235                 240

Ile Glu Tyr Ile His Phe Leu Ile Arg Gln Leu Arg Asn Leu Leu Ile
                245                 250                 255

Trp Leu Tyr Asp Gly Cys Arg Thr Leu Leu Lys Thr Phe Gln Thr
            260                 265                 270

Leu Gln Pro Ala Leu Gln Pro Leu Arg Leu Leu Phe Ala Tyr Leu Gln
        275                 280                 285

Tyr Gly Ile Gly Trp Phe Gln Glu Ala Val Gln Ala Ala Gly Ala
    290                 295                 300

Thr Gly Glu Thr Leu Ala Ser Thr Gly Arg Thr Leu Trp Glu Ala Leu
305                 310                 315                 320

Arg Arg Thr Ala Arg Gly Ile Ile Ala Val Pro Arg Arg Ile Arg Gln
                325                 330                 335

Gly Leu Glu Leu Ala Leu Leu
            340

<210> SEQ ID NO 32
<211> LENGTH: 1032
<212> TYPE: DNA
<213> ORGANISM: Artificial Sequence
<220> FEATURE:
<223> OTHER INFORMATION: chimeric polynucleotide comprising the
      nucleotide sequence encoding gp41 from HIV-2 7312A and a
      heterologous MPER epitope from HIV-1 (construct C4
      of Figure 11)
<220> FEATURE:
<221> NAME/KEY: CDS
<222> LOCATION: (1)...(1032)

<400> SEQUENCE: 32 ggt gta ttc gtg cta ggg ttc ttg ggt ttt ctc acg a

```
ttg gca tta gat aaa tgg gca agt ttg tgg aac tgg ttt gat tta gcc      480
Leu Ala Leu Asp Lys Trp Ala Ser Leu Trp Asn Trp Phe Asp Leu Ala
145                 150                 155                 160 tcc tgg gtc aaa tat att cag tat gga gtt tat ata gta gta gga ata      528
Ser Trp Val Lys Tyr Ile Gln Tyr Gly Val Tyr Ile Val Val Gly Ile
                165                 170                 175 gta gct ctc aga gta ata ata tat gta gta caa atg ata ggt aga ctt      576
Val Ala Leu Arg Val Ile Ile Tyr Val Val Gln Met Ile Gly Arg Leu
            180                 185                 190 aga aga ggc tat agg cct gtt ttc tct tcc ccc ccc ggt tac ttc caa      624
Arg Arg Gly Tyr Arg Pro Val Phe Ser Ser Pro Pro Gly Tyr Phe Gln
        195                 200                 205 cag atc cgt atc cac aag gac cag gaa cag cca gcc aac gaa gaa aca      672
Gln Ile Arg Ile His Lys Asp Gln Glu Gln Pro Ala Asn Glu Glu Thr
    210                 215                 220 gaa gaa gga ggt gga aac gac ggg ggc tac aga tct tgg ccc tgg cag      720
Glu Glu Gly Gly Gly Asn Asp Gly Gly Tyr Arg Ser Trp Pro Trp Gln
225                 230                 235                 240 atc gaa tac atc cac ttc cta att cgc cag ctg agg aac ctc ttg att      768
Ile Glu Tyr Ile His Phe Leu Ile Arg Gln Leu Arg Asn Leu Leu Ile
                245                 250                 255 tgg cta tac gac ggc tgc aga acc tta ctg ttg aag acc ttc caa acc      816
Trp Leu Tyr Asp Gly Cys Arg Thr Leu Leu Leu Lys Thr Phe Gln Thr
                260                 265                 270 ctc caa cca gct ctc caa cca ctc agg ctc ctg ttt gcg tac ctc caa      864
Leu Gln Pro Ala Leu Gln Pro Leu Arg Leu Leu Phe Ala Tyr Leu Gln
            275                 280                 285 tat ggg atc ggc tgg ttc caa gaa gca gtc caa gca gca gcg ggg gct      912
Tyr Gly Ile Gly Trp Phe Gln Glu Ala Val Gln Ala Ala Ala Gly Ala
        290                 295                 300 acg gga gag act ctt gcg agc aca ggg agg acc tta tgg gag gct ctc      960
Thr Gly Glu Thr Leu Ala Ser Thr Gly Arg Thr Leu Trp Glu Ala Leu
305                 310                 315                 320 agg agg acg gcg agg gga atc atc gca gtc ccc aga aga atc aga cag     1008
Arg Arg Thr Ala Arg Gly Ile Ile Ala Val Pro Arg Arg Ile Arg Gln
                325                 330                 335 ggg ctt gaa ctc gcc ctc ctg tga                                     1032
Gly Leu Glu Leu Ala Leu Leu  *
                340

<210> SEQ ID NO 33
<211> LENGTH: 343
<212> TYPE: PRT
<213> ORGANISM: Artificial Sequence
<220> FEATURE:
<223> OTHER INFORMATION: chimeric polypeptide encoding gp41 from HIV-2

```
Leu Asn Ser Trp Gly Cys Ala Phe Arg Gln Val Cys His Thr Thr Val
                85                  90                  95
Pro Trp Val Asn Asp Ser Leu Thr Pro Asp Trp Asp Asn Met Thr Trp
            100                 105                 110
Gln Gln Trp Glu Lys Gln Ile Arg Asp Leu Glu Ala Asn Ile Ser Glu
        115                 120                 125
Ser Leu Glu Gln Ala Gln Ile Gln Gln Glu Lys Asn Met Tyr Glu Leu
    130                 135                 140
Gln Lys Leu Asn Ser Trp Asp Val Phe Gly Asn Trp Phe Asp Ile Thr
145                 150                 155                 160
Lys Trp Leu Trp Tyr Ile Lys Tyr Gly Val Tyr Ile Val Val Gly Ile
                165                 170                 175
Val Ala Leu Arg Val Ile Ile Tyr Val Val Gln Met Ile Gly Arg Leu
            180                 185                 190
Arg Arg Gly Tyr Arg Pro Val Phe Ser Ser Pro Pro Gly Tyr Phe Gln
        195                 200                 205
Gln Ile Arg Ile His Lys Asp Gln Glu Gln Pro Ala Asn Glu Glu Thr
    210                 215                 220
Glu Glu Gly Gly Gly Asn Asp Gly Gly Tyr Arg Ser Trp Pro Trp Gln
225                 230                 235                 240
Ile Glu Tyr Ile His Phe Leu Ile Arg Gln Leu Arg Asn Leu Leu Ile
                245                 250                 255
Trp Leu Tyr Asp Gly Cys Arg Thr Leu Leu Leu Lys Thr Phe Gln Thr
            260                 265                 270
Leu Gln Pro Ala Leu Gln Pro Leu Arg Leu Leu Phe Ala Tyr Leu Gln
        275                 280                 285
Tyr Gly Ile Gly Trp Phe Gln Glu Ala Val Gln Ala Ala Ala Gly Ala
    290                 295                 300
Thr Gly Glu Thr Leu Ala Ser Thr Gly Arg Thr Leu Trp Glu Ala Leu
305                 310                 315                 320
Arg Arg Thr Ala Arg Gly Ile Ile Ala Val Pro Arg Ile Arg Gln
                325                 330                 335
Gly Leu Glu Leu Ala Leu Leu
                340
```

<210> SEQ ID NO 34
<211> LENGTH: 1032
<212> TYPE: DNA
<213> ORGANISM: Artificial Sequence
<220> FEATURE:
<223> OTHER INFORMATION: chimeric polynucleotide comprising the
      nucleotide sequence encoding gp41 from HIV-2 7312A and a
      heterologous MPER epitope from HIV-1 (construct C5
      of Figure 11)
<220> FEATURE:
<221> NAME/KEY: CDS
<222> LOCATION: (1)...(1032)

<400> SEQUENCE: 34

```
ggt gta ttc gtg cta ggg ttc ttg ggt ttt ctc acg aca gca gga gct    48
Gly Val Phe Val Leu Gly Phe Leu Gly Phe Leu Thr Thr Ala Gly Ala
 1               5                  10                  15 gca atg ggc gcg gcg tcc ttg acg ctg tcg gct cag tct cgg act tta    96
Ala Met Gly Ala Ala Ser Leu Thr Leu Ser Ala Gln Ser Arg Thr Leu
             20                  25                  30 ctg gcc ggg ata gtg cag caa cag caa cag ctg tta gac gtg gtc aag   144
Leu Ala Gly Ile Val Gln Gln Gln Gln Gln Leu Leu Asp Val Val Lys
         35                  40                  45 aga caa caa gaa atg ttg cga ctg acc gtc tgg gga aca aaa aat ctc   192
```

```
                                     Arg Gln Gln Glu Met Leu Arg Leu Thr Val Trp Gly Thr Lys Asn Leu
                                      50                  55                  60 cag gca aga gtc act gct att gag aaa tac tta aag gac cag gcg caa              240
Gln Ala Arg Val Thr Ala Ile Glu Lys Tyr Leu Lys Asp Gln Ala Gln
 65                  70                  75                  80 cta aat tca tgg gga tgt gcg ttt agg caa gtc tgc cac act act gta              288
Leu Asn Ser Trp Gly Cys Ala Phe Arg Gln Val Cys His Thr Thr Val
                 85                  90                  95 cca tgg gta aat gac agc ttg aca cct gat tgg gac aac atg acg tgg              336
Pro Trp Val Asn Asp Ser Leu Thr Pro Asp Trp Asp Asn Met Thr Trp
            100                 105                 110 caa caa tgg gaa aaa caa atc cgc gac ctg gag gca aat atc agt gaa              384
Gln Gln Trp Glu Lys Gln Ile Arg Asp Leu Glu Ala Asn Ile Ser Glu
        115                 120                 125 agt cta gaa cag gca caa atc cag caa gaa aag aac atg tat gaa tta              432
Ser Leu Glu Gln Ala Gln Ile Gln Gln Glu Lys Asn Met Tyr Glu Leu
    130                 135                 140 caa aaa tta aat agc tgg gat gtt ttt ggc aac tgg ttt gat ata acc              480
Gln Lys Leu Asn Ser Trp Asp Val Phe Gly Asn Trp Phe Asp Ile Thr
145                 150                 155                 160 tcc tgg gtc aaa tat att cag tat gga gtt tat ata gta gta gga ata              528
Ser Trp Val Lys Tyr Ile Gln Tyr Gly Val Tyr Ile Val Val Gly Ile
                165                 170                 175 gta gct ctc aga gta ata ata tat gta gta caa atg ata ggt aga ctt              576
Val Ala Leu Arg Val Ile Ile Tyr Val Val Gln Met Ile Gly Arg Leu
            180                 185                 190 aga aga ggc tat agg cct gtt ttc tct tcc ccc ccc ggt tac ttc caa              624
Arg Arg Gly Tyr Arg Pro Val Phe Ser Ser Pro Pro Gly Tyr Phe Gln
        195                 200                 205 cag atc cgt atc cac aag gac cag gaa cag cca gcc aac gaa gaa aca              672
Gln Ile Arg Ile His Lys Asp Gln Glu Gln Pro Ala Asn Glu Glu Thr
    210                 215                 220 gaa gaa gga ggt gga aac gac ggg ggc tac aga tct tgg ccc tgg cag              720
Glu Glu Gly Gly Gly Asn Asp Gly Gly Tyr Arg Ser Trp Pro Trp Gln
225                 230                 235                 240 atc gaa tac atc cac ttc cta att cgc cag ctg agg aac ctc ttg att              768
Ile Glu Tyr Ile His Phe Leu Ile Arg Gln Leu Arg Asn Leu Leu Ile
                245                 250                 255 tgg cta tac gac ggc tgc aga acc tta ctg ttg aag acc ttc caa acc              816
Trp Leu Tyr Asp Gly Cys Arg Thr Leu Leu Leu Lys Thr Phe Gln Thr
            260                 265                 270 ctc caa cca gct ctc caa cca ctc agg ctc ctg ttt gcg tac ctc caa              864
Leu Gln Pro Ala Leu Gln Pro Leu Arg Leu Leu Phe Ala Tyr Leu Gln
        275                 280                 285 tat ggg atc ggc tgg ttc caa gaa gca gtc caa gca gca gcg ggg gct              912
Tyr Gly Ile Gly Trp Phe Gln Glu Ala Val Gln Ala Ala Ala Gly Ala
    290                 295                 300 acg gga gag act ctt gcg agc aca ggg agg acc tta tgg gag gct ctc              960
Thr Gly Glu Thr Leu Ala Ser Thr Gly Arg Thr Leu Trp Glu Ala Leu
305                 310                 315                 320 agg agg acg gcg agg gga atc atc gca gtc ccc aga aga atc aga cag             1008
Arg Arg Thr Ala Arg Gly Ile Ile Ala Val Pro Arg Arg Ile Arg Gln
                325                 330                 335 ggg ctt gaa ctc gcc ctc ctg tga                                             1032
Gly Leu Glu Leu Ala Leu Leu  *
            340

<210> SEQ ID NO 35
<211> LENGTH: 343
<212> TYPE: PRT
<213> ORGANISM: Artificial Sequence
```

```
<220> FEATURE:
<223> OTHER INFORMATION: chimeric polypeptide comprising the gp41 from
      HIV-2 7312A and a heterologous MPER epitope from
      HIV-1 (construct C5 of Figure 11)

<400> SEQUENCE: 35

Gly Val Phe Val Leu Gly Phe Leu Gly Phe Leu Thr Thr Ala Gly Ala
 1               5                  10                  15

Ala Met Gly Ala Ala Ser Leu Thr Leu Ser Ala Gln Ser Arg Thr Leu
                20                  25                  30

Leu Ala Gly Ile Val Gln Gln Gln Gln Leu Leu Asp Val Val Lys
            35                  40                  45

Arg Gln Gln Glu Met Leu Arg Leu Thr Val Trp Gly Thr Lys Asn Leu
        50                  55                  60

Gln Ala Arg Val Thr Ala Ile Glu Lys Tyr Leu Lys Asp Gln Ala Gln
 65                  70                  75                  80

Leu Asn Ser Trp Gly Cys Ala Phe Arg Gln Val Cys His Thr Thr Val
                85                  90                  95

Pro Trp Val Asn Asp Ser Leu Thr Pro Asp Trp Asp Asn Met Thr Trp
            100                 105                 110

Gln Gln Trp Glu Lys Gln Ile Arg Asp Leu Glu Ala Asn Ile Ser Glu
        115                 120                 125

Ser Leu Glu Gln Ala Gln Ile Gln Gln Glu Lys Asn Met Tyr Glu Leu
130                 135                 140

Gln Lys Leu Asn Ser Trp Asp Val Phe Gly Asn Trp Phe Asp Ile Thr
145                 150                 155                 160

Ser Trp Val Lys Tyr Ile Gln Tyr Gly Val Tyr Ile Val Val Gly Ile
                165                 170                 175

Val Ala Leu Arg Val Ile Ile Tyr Val Val Gln Met Ile Gly Arg Leu
            180                 185                 190

Arg Arg Gly Tyr Arg Pro Val Phe Ser Ser Pro Pro Gly Tyr Phe Gln
        195                 200                 205

Gln Ile Arg Ile His Lys Asp Gln Glu Gln Pro Ala Asn Glu Glu Thr
210                 215                 220

Glu Glu Gly Gly Gly Asn Asp Gly Gly Tyr Arg Ser Trp Pro Trp Gln
225                 230                 235                 240

Ile Glu Tyr Ile His Phe Leu Ile Arg Gln Leu Arg Asn Leu Leu Ile
                245                 250                 255

Trp Leu Tyr Asp Gly Cys Arg Thr Leu Leu Leu Lys Thr Phe Gln Thr
            260                 265                 270

Leu Gln Pro Ala Leu Gln Pro Leu Arg Leu Leu Phe Ala Tyr Leu Gln
        275                 280                 285

Tyr Gly Ile Gly Trp Phe Gln Glu Ala Val Gln Ala Ala Ala Gly Ala
    290                 295                 300

Thr Gly Glu Thr Leu Ala Ser Thr Gly Arg Thr Leu Trp Glu Ala Leu
305                 310                 315                 320

Arg Arg Thr Ala Arg Gly Ile Ile Ala Val Pro Arg Arg Ile Arg Gln
                325                 330                 335

Gly Leu Glu Leu Ala Leu Leu
            340

<210> SEQ ID NO 36
<211> LENGTH: 1032
<212> TYPE: DNA
<213> ORGANISM: Artificial Sequence
<220> FEATURE:
<223> OTHER INFORMATION: chimeric polynucleotide encoding the gp41 from
```

HIV-2 7312A and a heterologous MPER epitope from
HIV-1 (construct C6 of Figure 11)
<220> FEATURE:
<221> NAME/

```
tat ggg atc ggc tgg ttc caa gaa gca gtc caa gca gca gcg ggg gct    912
Tyr Gly Ile Gly Trp Phe Gln Glu Ala Val Gln Ala Ala Ala Gly Ala
    290                 295                 300 acg gga gag act ctt gcg agc aca ggg agg acc tta tgg gag gct ctc    960
Thr Gly Glu Thr Leu Ala Ser Thr Gly Arg Thr Leu Trp Glu Ala Leu
305                 310                 315                 320 agg agg acg gcg agg gga atc atc gca gtc ccc aga aga atc aga cag   1008
Arg Arg Thr Ala Arg Gly Ile Ile Ala Val Pro Arg Arg Ile Arg Gln
                325                 330                 335 ggg ctt gaa ctc gcc ctc ctg tga                                   1032
Gly Leu Glu Leu Ala Leu Leu  *
                340
```

<210> SEQ ID NO 37
<211> LENGTH: 343
<212> TYPE: PRT
<213> ORGANISM: Artificial Sequence
<220> FEATURE:
<223> OTHER INFORMATION: chimeric polypeptide comprising the gp41 from
      HIV-2 7312A and a heterologous MPER epitope from
      HIV-1 (construct C6 of Figure 11)

<400> SEQUENCE: 37

```

```
                  275                 280                 285
Tyr Gly Ile Gly Trp Phe Gln Glu Ala Val Gln Ala Ala Gly Ala
            290                 295                 300

Thr Gly Glu Thr Leu Ala Ser Thr Gly Arg Thr Leu Trp Glu Ala Leu
305                 310                 315                 320

Arg Arg Thr Ala Arg Gly Ile Ile Ala Val Pro Arg Ile Arg Gln
                325                 330                 335

Gly Leu Glu Leu Ala Leu Leu
            340

<210> SEQ ID NO 38
<211> LENGTH: 23
<212> TYPE: PRT
<213> ORGANISM: Human Immunodeficiency Virus type 1 YU2
<220> FEATURE:
<221> NAME/KEY: DOMAIN
<222> LOCATION: (0)...(0)
<223> OTHER INFORMATION: Membrane Proximal External Region (MPER) of gp
      41 from HIV-1 YU2.

<400> SEQUENCE: 38

Leu Ala Leu Asp Lys Trp Ala Ser Leu Trp Asn Trp Phe Asp Ile Thr
1               5                   10                  15

Lys Trp Leu Trp Tyr Ile Lys
            20

<210> SEQ ID NO 39
<211> LENGTH: 343
<212> TYPE: PRT
<213> ORGANISM: Human Immunodeficiency Virus Type 2 7312A

<400> SEQUENCE: 39

Gly Val Phe Val Leu Gly Phe Leu Gly Phe Leu Thr Thr Ala Gly Ala
1               5                   10                  15

Ala Met Gly Ala Ala Ser Leu Thr Leu Ser Ala Gln Ser Arg Thr Leu
            20                  25                  30

Leu Ala Gly Ile Val Gln Gln Gln Gln Gln Leu Leu Asp Val Val Lys
        35                  40                  45

Arg Gln Gln Glu Met Leu Arg Leu Thr Val Trp Gly Thr Lys Asn Leu
50                  55                  60

Gln Ala Arg Val Thr Ala Ile Glu Lys Tyr Leu Lys Asp Gln Ala Gln
65                  70                  75                  80

Leu Asn Ser Trp Gly Cys Ala Phe Arg Gln Val Cys His Thr Thr Val
                85                  90                  95

Pro Trp Val Asn Asp Ser Leu Thr Pro Asp Trp Asp Asn Met Thr Trp
            100                 105                 110

Gln Gln Trp Glu Lys Gln Ile Arg Asp Leu Glu Ala Asn Ile Ser Glu
        115                 120                 125

Ser Leu Glu Gln Ala Gln Ile Gln Gln Glu Lys Asn Met Tyr Glu Leu
    130                 135                 140

Gln Lys Leu Asn Ser Trp Asp Val Phe Gly Asn Trp Phe Asp Leu Ala
145                 150                 155                 160

Ser Trp Val Lys Tyr Ile Gln Tyr Gly Val Tyr Ile Val Val Gly Ile
                165                 170                 175

Val Ala Leu Arg Val Ile Ile Tyr Val Val Gln Met Ile Gly Arg Leu
            180                 185                 190

Arg Arg Gly Tyr Arg Pro Val Phe Ser Ser Pro Pro Gly Tyr Phe Gln
        195                 200                 205
```

-continued

```
Gln Ile Arg Ile His Lys Asp Gln Glu Gln Pro Ala Asn Glu Glu Thr
    210                 215                 220
Glu Glu Gly Gly Gly Asn Asp Gly Gly Tyr Arg Ser Trp Pro Trp Gln
225                 230                 235                 240
Ile Glu Tyr Ile His Phe Leu Ile Arg Gln Leu Arg Asn Leu Leu Ile
                245                 250                 255
Trp Leu Tyr Asp Gly Cys Arg Thr Leu Leu Leu Lys Thr Phe Gln Thr
            260                 265                 270
Leu Gln Pro Ala Leu Gln Pro Leu Arg Leu Leu Phe Ala Tyr Leu Gln
        275                 280                 285
Tyr Gly Ile Gly Trp Phe Gln Glu Ala Val Gln Ala Ala Ala Gly Ala
    290                 295                 300
Thr Gly Glu Thr Leu Ala Ser Thr Gly Arg Thr Leu Trp Glu Ala Leu
305                 310                 315                 320
Arg Arg Thr Ala Arg Gly Ile Ile Ala Val Pro Arg Arg Ile Arg Gln
                325                 330                 335
Gly Leu Glu Leu Ala Leu Leu
            340
```

MOLECULAR SCAFFOLDS FOR HIV-1 EPITOPES

CROSS REFERENCE TO RELATED APPLICATIONS

This application is a §371 U.S. National Stage of International Application No. PCT/US2005/011928, filed Apr. 8, 2005, which claims the benefit of U.S. Provisional Application Ser. No. 60/562,824, filed Apr. 16, 2004, U.S. Provisional Application Ser. No. 60/606,053, filed Aug. 31, 2004, and U.S. Provisional Application Ser. No. 60/649,551, filed Feb. 3, 2005, the contents of which are herein incorporated by reference in their entirety.

FEDERALLY SPONSORED RESEARCH OR DEVELOPMENT

The research underlying a portion of this invention was supported in part with funds from National Institute of Health grant no. U01 AI41530. The United States Government may have an interest in the subject matter of this invention.

FIELD OF THE INVENTION

The invention relates to the field of retroviruses, particularly lentivirus.

BACKGROUND OF THE INVENTION

The antibody response to HIV-1 infection is typically vigorous and sustained but its effectiveness in virus containment in vivo is uncertain. We and others have shown in acutely infected individuals the rapid development of HIV-1 strain-specific neutralizing antibodies (Nab), and the equally rapid emergence of virus escape mutations (Albert et al. (1990) *AIDS* 4:107-112; Moog et al. (1997) *J Virol* 71:3734-3741; Wei et al. (2003) *Nature* 422:307-312; Richman et al. (2003) *Proc Natl Acad Sci USA* 100:4144-41492). Such strain-specific antibody responses are common, and they clearly drive virus selection in vivo (Wei et al. (2003) *Nature* 422:307-312; Richman et al. (2003) *Proc Natl Acad Sci USA* 100:4144-41492). More broadly reactive Nabs develop over longer periods (Pilgrim et al. (1997) *J Infect Dis* 176:924-932; Montefiori et al. (2001) *J Virol* 75:10200-10207; Parren et al (1999) *Aids* 13 Suppl A:S137-162). HIV-1 has evolved a variety of defense mechanisms to avoid antibody recognition, including epitope variation, oligomeric exclusion, conformational masking, glycan cloaking, and steric interference at the virus:cell interface (Kwong et al. (1998) *Nature* 393:648-659; Wyatt et al. (1998) *Nature* 393:705-711; Wyatt et al. (1998) *Science* 280:1884-1888; Kwong et al. (2002) *Nature* 420:678-682; Labrijn et al. (2003) *J Virol* 77:10557-10565; Burton et al. (2004) *Nat Immunol* 5:233-236; Zolla-Pazner et al (2004) *Nat Rev Immunol* 4:199-210), and together, they contribute to virus persistence in the face of an evolving antibody repertoire (Wei et al (2003) *Nature* 422:307-312; Richman et al. (2003) *Proc Natl Acad Sci USA* 100:4144-41492). But the precise nature of this evolving antibody response in vivo is incompletely understood. Analysis of HIV-1 specific monoclonal antibodies has revealed variable loop, CD4 binding site, chemokine co-receptor binding site, surface glycan, and membrane proximal gp41 domains as neutralization targets (reviewed in Burton et al. (2004) *Nat Immunol* 5:233-236; Zolla-Pazner et al (2004) *Nat Rev Immunol* 4:199-210), but the prevalence, titers, and breadth of polyclonal antibody responses to these epitopes in humans are generally unknown. This is in part a consequence of technical difficulty in identifying epitope-specific neutralizing antibody responses within a larger context of polyclonal neutralizing and non-neutralizing antibody reactivities (Broliden et al. (1992) *Proc Natl Acad Sci USA* 89:461-465; Scala et al. (1999) *J Immunol* 162:6155-6161; Opalka et al. (2004) *J Immunol Methods* 287:49-65).

It is clear that methods and compositions are needed to identify immunogenic, broadly-cross reactive epitopes on the HIV-1 envelope glycoprotein that might serve as targets of the adaptive humoral immune response in naturally-infected humans. Further needed are methods and compositions that allow for the detection of neutralizing HIV-1 antibodies.

BRIEF SUMMARY OF THE INVENTION

Methods and compositions are provided to detect and identify HIV-1 binding antibodies. In specific methods and compositions, the HIV-1 binding antibody is a neutralizing antibody and/or a CD4-induced antibody. Such methods and compositions are capable of inducing a broadly protective response against HIV.

Methods are provided for detecting an HIV-1 binding antibody in a subject infected with human immunodeficiency virus-1 (HIV-1). The method comprises providing an envelope polypeptide or a functional variant thereof from a lentivirus that is not HIV-1, wherein the envelope polypeptide comprises at least one epitope recognized by an HIV-1 binding antibody. In specific methods, the envelope polypeptide is selected from the group consisting of an HIV-2 envelope polypeptide, a functional variant of the HIV-2 envelope, a Simian Immunodeficiency virus (SIV) envelope polypeptide or a functional variant of the SIV envelope polypeptide. The envelope polypeptide is contacted with an amount of bodily fluid from the subject. The HIV-1 binding antibody is detected. In specific methods, the method is capable of detecting the binding antibody present in the bodily fluid when present at a concentration of less than 0.1 µg/ml.

Methods are further provided for detecting CD4-induced antibodies in a subject infected with HIV-1. The method comprises providing an effective concentration of a soluble CD4/envelope complex. The complex comprises a soluble CD4 or a functional variant thereof and an envelope polypeptide from a lentivirus that is not HIV-1. The complex is contacted with an amount of bodily fluid from the subject; and, the CD4-induced antibodies are detected.

Methods for a diagnostic assay to monitor HIV disease in a subject or to monitor the response of a subject to immunization by an HIV vaccine are provided. The method comprises providing an envelope polypeptide or a functional variant thereof that is not from HIV-1 and comprises at least one epitope recognized by an HIV-1 binding antibody. The envelope polypeptide is contacted with an amount of bodily fluid from the subject, and the HIV-1 binding antibody in the bodily fluid of the subject is detected and HIV disease in the subject is thereby monitored or the response of the subject to immunization by an HIV vaccine is monitored. In specific methods, the envelope polypeptide is associated with a retrovirus.

Additional methods comprise providing an effective concentration of soluble CD4/envelope complex; contacting the complex with an amount of bodily fluid from the subject; and, detecting the CD4-induced antibodies in the bodily fluid of the subject and thereby monitoring HIV disease in the subject or the response of the subject to immunization by an HIV vaccine.

Additional methods include an assay for an HIV-1 binding antibody. The method comprises providing an envelope polypeptide or a functional variant thereof that is not from HIV-1 and the envelope polypeptide comprises an epitope recognized by an HIV-1 binding antibody. The envelope polypeptide is contacted with a composition comprising a candidate HIV-1 binding antibody; and, it is determined if the candidate antibody is an HIV-1 binding antibody.

Methods are also provided to determine an epitope for an HIV-1 binding antibody. The method comprises providing a population of envelope polypeptides or functional variants thereof that are not from HIV-1 and, wherein members of the envelope polypeptides in the population comprise at least one epitope recognized by the HIV-1 binding antibody and the envelope polypeptides in the population are substantially identical to one another. The population of envelope polypeptides is contacted with a composition comprising the HIV-1 binding antibody; and, the envelope polypeptide in the population that is recognized by the HIV-1 binding antibody is determined and the epitope for the HIV-1 binding antibody is thereby determined.

Methods are also provided to identify a soluble CD4 (sCD4) mimic. The method comprises providing an envelope polypeptide from a lentivirus that is not HIV-1; contacting the envelope polypeptide or a variant thereof with a candidate compound; and determining if the candidate compound interacts with the envelope polypeptide or functional variant thereof, wherein the interaction of the candidate compound and the envelope polypeptide or functional variant thereof increases the accessibility of an epitope or creates the epitope on the envelope polypeptide or the functional variant thereof, wherein the epitope is recognized by a CD4-induced antibody. In other methods, the CD4-induced antibody is from a subject infected with HIV-1, or the CD4-induced antibody was developed against an HIV-1.

A method to neutralize HIV-2 or SIV is also provided. The method comprises providing a composition comprising the HIV-2 or the SIV; providing to the composition an effective concentration of sCD4 or a functional variant thereof, wherein the sCD4 or the functional variant thereof is provided under conditions that allow for the interaction of the sCD4 or the functional variant thereof with the envelope polypeptide or the functional variant thereof of the HIV-2 or the SIV; and, providing to the composition an isolated CD4-induced antibody. In specific methods, the CD4-induced antibody is from a subject infected with HIV-1. In other methods, an effective concentration of the sCD4 is provided, and is some methods, the effective concentration of sCD4 comprises a concentration of about 1 nM to about 1000 nM.

Methods to alter the neutralization potential of a CD4-induced antibody elicited by HIV-1 are also provided. The method comprises providing an effective concentration of a soluble CD4/envelope complex; providing to the soluble CD4/envelope complex a CD4-induced antibody elicited by a HIV-1; and, thereby altering the neutralization potential of the CD4-induced antibody.

In specific methods, the envelope polypeptide employed in the methods is associated with a retrovirus. In other methods, the retrovirus is HIV-2 or SIV. In still other methods, the HIV-2 comprises the HIV-2 isolate 7312A or the ST isolate or a molecular clone thereof. In other methods, the retrovirus comprises a pseudotyped primate lentivirus. In other methods, the envelope polypeptide comprises an amino acid sequence having at least 70% sequence identity to the sequence set forth in SEQ ID NO: 2, 3, 4, or 5.

In yet other methods, the epitope recognized by the HIV-1 binding antibody is found within gp41, gp120 or the membrane proximal external region of gp41. In still further methods, the epitope recognized by the HIV-1 binding antibody comprises a 4E10 epitope, a 2F5 epitope, or a Z13 epitope. The epitope recognized by the HIV-1 binding antibody can be homologous or heterologous to the envelope polypeptide.

Compositions of the invention include a chimeric polynucleotide comprising a nucleotide sequence encoding an envelope polypeptide or functional variant thereof that is not from HIV-1, wherein the amino acid sequence further comprises a heterologous epitope recognized by an HIV-1 neutralization antibody.

Additional compositions include a chimeric polypeptide comprising an amino acid sequence of an envelope polypeptide or a functional variant thereof that is not from HIV-1, wherein the amino acid sequence further comprises a heterologous epitope recognized by an HIV-1 neutralization antibody.

Cells, viruses, kits, and directs for their use comprising the various compositions of the invention are further provided. Additional compositions include a kit comprising a soluble CD4/envelope complex and directions for use.

BRIEF DESCRIPTION OF THE DRAWINGS

FIG. 4 shows the envelope gp120 alignments for HIV-2 (7312A (SEQ ID NO:2) and UC1 (SEQ ID NO:7)), SIV (Mac239 (SEQ ID NO:11) and Ver-Tyo1 (SEQ ID NO:12)), and HIV-1 (YU2 (SEQ ID NO:13) and HXB2 (SEQ ID NO:16)). Bridging sheet, variable loops, amino acid identities, and site-directed mutations (H419R, Q422L, and V434M) are indicated. The signal peptide-gp120 cleavage position for HIV-1 is shown. Variable loops (V1/V2, V3, and V4) have conventionally been defined by disulfide-linked cysteine residues at their bases, as depicted. However, the actual limits of variable loops have been resolved structurally in the HXB2-CD4-17b crystal complex (Kwong (1998)*Nature* 393:648-659), and these sequences are indicated by green bars. It is possible that structural details diverge in the more distantly related HIV/SIV sequences. The amino acids contributing to the bridging sheet are highlighted in yellow. Blue dots indicate residues contributing to chemokine co-receptor binding based on site-directed mutagenesis studies (Rizzuto (1998) *Science* 280:1949-1953; Rizzuto (2000) *AIDS Res Hum Retroviruses* 16:741-749). Additional amino acids within the stem of V3, including 298R, 301N, 303T, 323I, 325N, 326M and 327R, may contribute to gp120 interaction with CCR5 (Cormier (2001) *J Virol* 75:5541-5549). Red dots indicate HIV-1 contact residues for CD4 based on crystal structure analyses (Kwong (1998) *Nature* 393:648-659). Asterisks below the sequence indicate conservation of amino acid identity across all five virus strains. Overall gp120 sequence identity was calculated based on amino acid residues exclusive of the initiator methionine of the (cleaved) signal peptide and a gap-stripped alignment of the sequences shown. Except for SIVverTYO1, sequences were obtained from the *HIV Sequence Compendium* 2002 (*HIV Sequence Compendium* (2002) Kuiken et al. Eds. Los Alamos National Laboratory, Los Alamos, NM, LA-UR 03-3564). We determined experimentally the nucleotide sequence of the SIVverTYO1 clone used in our studies (lambda phage SAH12) and found that it differed from the reported sequence of the same clone in the Compendium at positions 171(-), 172(N), 402 (D), 418(C) and 427(W). Numbering is according to the HXB2 sequence.

FIG. 7 provides an alignment of the amino acid sequences of various envelope polypeptides from HIV-2 viruses including, 7312A (SEQ ID NO:2), UC1 (SEQ ID NO:7), UC2 (SEQ ID NO:8) and ROD-B.14 (SEQ ID NO:9) and the amino acid sequence of envelope from HIV-1 virus HXB2 (SEQ ID NO:10).

FIG. 8 provides the location of 2F5 (single underline) and 4E10 (double underline) Epitopes in HIV-1 (YU-2 and HXB-2c) gp41 and corresponding sequences in HIV-2 (ST, 7312A, and UC1). This alignment shows the conservation of the 4E10 epitope at a sequence level and as a target of 4E10-mediated neutralization between HUV-1 and HIV-2. The envelope polypeptides comprises ST (SEQ ID NO:14), 7312A (SEQ ID NO:2); UC1 (SEQ ID NO:7), HXB-2c (SEQ ID NO:10), and YU-2 (SEQ ID NO:13). The amino acid numbering shown in this figure refers to number of the HXB-2c sequence.

FIG. 11 provides the amino acids sequence of 6 chimeric envelope polypeptides from HIV-2 7312A. Amino acids 647 to 687 of the 7312A envelope polypeptide (SEQ ID NO:2) is shown with a region of the MPER double underlined. The constructs designated as 7312A-C1, 7312A-C2, 7312A-C3, 7312A-C4 (SEQ ID NO:27, 29, 31, and 33, respectively) are chimeric 7312A envelope polypeptides in which a region of the MPER domain from an HIV-1 envelope polypeptide has been substituted for the native HIV-2 sequence. The heterologous domain derived from HIV-1 is in bold and highlighted. Similarly, constructs 7312A-C5 and 7312A-C6 (SEQ ID NO:35 and 37, respectively) represent chimeric 7312A envelope polypeptides in which specific amino acid substitutions were made to introduce HIV-1 epitopes into the HIV-2 envelope polypeptide.

DETAILED DESCRIPTION OF THE INVENTION

Figure 1A:
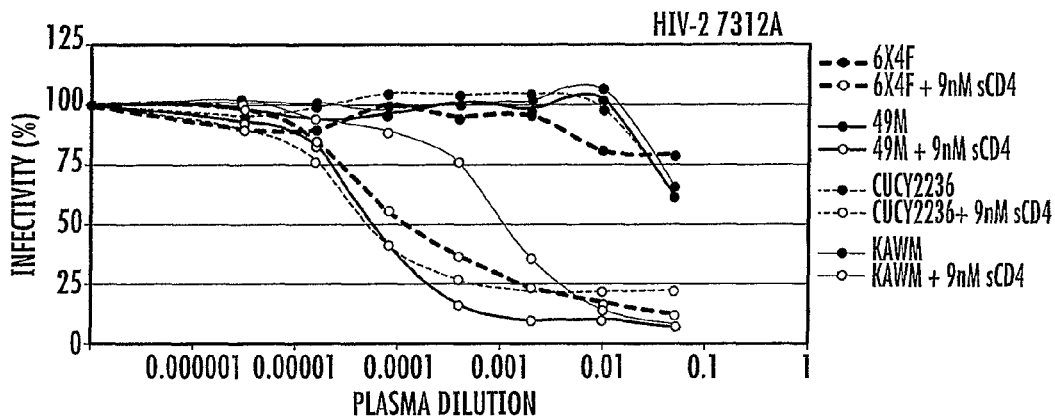
FIG. 1 shows the neutralization of HIV-$2_{7312A}$ (panels a, b) and HIV-$2_{7312A/V434M}$ (panel c) infectivity in JC53BL-13 cells (3) by plasma from patients with HIV-1 clade A (6X4F), B (CUCY2236), C (49M), or D (KAWM) infection or by the HIV-1 CD4i monoclonal antibodies 21c, 19e, or 17b. sCD4 concentrations correspond to the $IC_{50}$ values specific for each virus.

The present inventions now will be described more fully hereinafter with reference to the accompanying examples, in which some, but not all claims of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The article "a" and "an" are used herein to refer to one or more than one (i.e., to at least one) of the grammatical object of the article. By way of example, "an element" means one or more than one element.

With many HIV-1 vaccine candidates currently in the research pipeline, methods are needed for detecting and quantifying epitope-specific neutralizing antibody responses in naturally-infected individuals and vaccinated subjects. HIV-1 and HIV-2 share less than 50% sequence similarity in envelope and they generally exhibit little cross-neutralization. The present invention demonstrates the successful identification of HIV-1 neutralization epitopes in, or molecularly engineered into, functional envelope glycoproteins from non-HIV-1 envelope polypeptides. Accordingly, various methods and compositions are provided for the detection and/or characterization of an HIV-1 binding antibody, particularly HIV-1 neutralizing antibodies.

As used herein an "HIV-1 binding antibody" comprises an antibody that specifically interacts with an epitope of HIV-1. In specific embodiments, the HIV-1 binding antibody interacts with an epitope of the envelope polypeptide of HIV-1. An HIV-1 binding antibody that can neutralize a virus is referred to herein as an "HIV-1 neutralizing antibody." Additional HIV-1 binding antibodies include CD4-induced antibodies, and in more specific embodiments, the CD4-induced antibodies are neutralizing antibodies.

By "specifically interacts" is intended that the antibody that recognizes the epitope of an HIV-1 envelope polypeptide forms a specific antibody-antigen complex with that epitope (either in an in vitro or in vivo setting) when the epitope is contained in an envelope polypeptide that is not from HIV-1. Thus, the HIV-1 binding antibody binds preferentially to the non-HIV-1 envelope polypeptide comprising the HIV-1 epitope. By "binds preferentially" is meant that the antibody immunoreacts with (binds) substantially more of the non-HIV-1 envelope polypeptide comprising the HIV-1 epitope than the non-HIV-1 envelope polypeptide lacking the epitope, when both polypeptides are present in an immunoreaction admixture. Substantially more typically indicates at least greater than 10%, 20%, 30%, 40%, 50%, 60%, 70%, 80%, 90%, 95%, or greater of the immunoprecipitated material is the non-HIV-1 envelope polypeptide comprising the HIV-1 epitope.

Methods are provided for the detection of an HIV-1 binding antibody (i.e., a neutralizing antibody) in a subject infected with HIV-1. The method comprises providing an envelope polypeptide or a functional variant thereof from a lentivirus that is not HIV-1, where the envelope polypeptide comprises at least one epitope recognized by an HIV-1 binding antibody. The envelope polypeptide is contacted with an amount of bodily fluid from the subject, and the HIV-binding antibodies are detected. Methods for contacting the envelope polypeptide with the HIV-1 binding antibody include in-vitro binding studies such as those discussed in Xiang et al. (2002) *AIDS Res Hum Retroviruses* 18:1207-17; Cavacini et al. (2003) *AIDS* 17:1863; and Xiang et al. (2003) *Virology* 315: 124-34, each of which is herein incorporated by reference. Alternatively, the envelope polypeptide can be in association with a lipid bilayer in a number of different ways, so long as the envelope polypeptide exists in one or more confirmation that is similar to the envelope protein in its native environment. In one method, the envelope polypeptide is associated with a retrovirus. By "associated" is intended the envelope polypeptide is present on the surface of the retrovirus. In this method, a composition comprising a retrovirus having an envelope polypeptide from a primate lentivirus that is not HIV-1 is provided. An amount of bodily fluid from the subject is contacted with the envelope polypeptide, and the HIV-1 binding antibodies are detected. Any bodily fluid can be employed in the methods of the invention, including, but not limited to, serum, plasma, semen, milk, etc. If the HIV-1 binding antibodies are present in the patient bodily fluid, the antibodies will interact with the epitope. In specific embodiments, the interaction of the antibody with the epitope results in the neutralization of the virus in the sample.

Methods to assay for an interaction of an HIV-1 binding antibody with an epitope on the envelope polypeptide are known. For example, formation of an antibody-antigen complex using a number of well-defined diagnostic assays can be used including conventional immunoassay formats to detect and/or quantitate antigen-specific antibodies. Such assays include, for example, enzyme immunoassays, e.g., ELISA, cell-based assays, flow cytometry, radioimmunoassays, and immunohistochemical staining. Numerous competitive and non-competitive protein binding assays are known in the art and many are commercially available. Representative assays include, for example, various binding assays with chemokine receptors (CCR5 or CXCR4), gp41, characterized domains of these polypeptides, and competitive binding assays with characterized HIV-1 binding antibodies. In addition, if the envelope polypeptide is associated with a retrovirus, "neutralization" of the virus and thereby reducing the establishment of HIV infection and/or reducing subsequent HIV disease progression (i.e., reduces the severity of the symptoms of the HIV infection) in a sample when compared to a control virus lacking the HIV-1 binding antibody can also be assayed. A reduction in the establishment of HIV infection and/or a reduction in subsequent HIV disease progression encompasses any statistically significant reduction in HIV activity in the sample. Such HIV-1 binding antibodies that neutralize the virus are referred to herein as "HIV-1 neutralizing antibodies." Methods to assay for the neutralization activity include, but are not limited to, a single-cycle infection assay as described in Martin et al. (2003) *Nature Biotechnology* 21:71-76. In this assay, the level of viral activity is measured via a selectable marker whose activity is reflective of the amount of viable virus in the sample, and the IC50 is determined. In other assays, acute infection can be monitored in the PM1 cell line or in primary cells (normal PBMC). In this assay, the level of viral activity can be monitored by determining the p24 concentrations using ELISA. See, for example, Martin et al. (2003) *Nature Biotechnology* 21:71-76, herein incorporated by reference. Further methods include those employing the adherent HeLa cell-derived JC53BL-13 cell line (NIH AIDS Research and Reference Reagent Program Catalogue No. 8129, TZM-bl) as described in Wei et al. (2003) *Nature* 422:307-312, herein incorporated by reference.

The method of detecting the HIV-1 binding antibodies is very sensitive and is capable of detecting HIV-1 binding antibody concentrations of less than about 1 µg/ml, less about 0.5 µg/ml, less than about 0.3 µg/ml, less than about 0.2 µg/ml, less than about 0.1 µg/ml, less than about 0.09 µg/ml, less than about 0.08 µg/ml less than about, 0.07 µg/ml, less than about 0.06 µg/ml, less than about 0.05 µg/ml, less than about 0.04 µg/ml, less than about 0.03 µg/ml, less than about 0.02 µg/ml, less than about 0.01 µg/ml, less than about 0.009 µg/ml, less than about 0.005 µg/ml, or less than about 0.001 µg/ml or less.

In other methods the HIV-1 binding antibody is a CD4-induced antibody. In specific embodiments, the CD4-induced antibody is a neutralizing antibody. Accordingly, methods are also provided for the detection of CD4-induced antibodies in a subject infected with HIV-1. The method comprises providing an effective concentration of a soluble CD4/envelope complex. The complex comprises a soluble CD4 or a functional variant thereof and an envelope polypeptide from a lentivirus that is not HIV-1 or a functional variant thereof. The soluble CD4/envelope complex is contacted with an amount of bodily fluid from the subject and the CD4-induced antibodies are detected.

As used herein, a "soluble CD4/envelope complex" comprises a soluble CD4 or a functional variant thereof and an envelope polypeptide from a primate lentivirus that is not HIV-1 (i.e., HIV-2, SIV, SRV-1, SUV-2, Simian human immunodeficiency virus, and HIV-3) or a functional variant thereof. The components of the complex can interact through covalent or non-covalent interactions. In specific embodiments, the interactions between the sCD4 and the envelope polypeptides are non-covalent. Methods for forming such a complex include those discussed in Xiang et al. (2002) *AIDS Res Hum Retroviruses* 18:1207-17; Cavacini et al. (2003) *AIDS* 17:1863; and Xiang et al. (2003) *Virology* 315:124-34, each of which is herein incorporated by reference.

As used herein, the term "CD4-induced antibody" comprises an antibody that interacts with an epitope of the envelope polypeptide of a primate lentivirus, where the epitope is created or exposed or the accessibility of the epitope is increased in the presence of an effective concentration of soluble CD4 or a functional variant of soluble CD4. The created epitope or the epitope having the increased accessibility under these conditions is referred to herein as a "CD4-induced epitope." Methods to measure the creation of an epitope or an increase in exposure or accessibility of an epitope are discussed elsewhere herein. Briefly, binding assays with compounds that interact with the exposed epitope can be performed. Such compounds include, for example, characterized CD4-induced antibodies and chemokine receptors. In the method described above, soluble CD4 interacts with the envelope polypeptide and increases the accessibility of a CD4-induced epitope. If CD4-induced antibodies are present in the patient bodily fluid, the antibody will interact with the epitope. In specific embodiments, the interaction of the antibody with the epitope results in the neutralization of the virus in the sample. It is recognized that specific methods of the invention can be performed in-vitro or in-vivo.

Methods to assay for an interaction of a CD4-induced antibody with an epitope on the envelope polypeptide include, for example, various binding assays with chemokine receptors (CCR5 or CXCR4) or with characterized CD4 induced antibodies. In addition, if the envelope polypeptide is associated with a retrovirus, "neutralization" of the virus can be assays. Such methods are discussed in detail elsewhere herein.

In specific methods of the invention, the HIV-1 binding antibody, neutralizing antibody, and/or CD4-induced antibody is isolated. An "isolated" antibody is substantially or essentially free from components that normally accompany or interact with the antibody as found in its naturally occurring environment. Thus, an isolated or purified antibody is substantially free of other cellular material or culture medium. An antibody that is substantially free of cellular material or culture medium includes preparations of antibody having less than about 30%, 20%, 10%, 5%, or 1% (by dry weight) of contaminating protein.

The envelope polypeptide employed in the methods may be in the either in the glycosylated or deglycosylated form. In addition, the envelope of the invention can be an envelope polypeptide from any lentivirus or any primate lentivirus. In specific methods, the envelope polypeptide is from any primate lentivirus that is not HIV-1. Such primate lentivirus include, for example, HIV-2 (Isolate BEN), HIV-2 (Isolate CAM2), HIV-2 (Isolate D194), HIV-2 (Isolate D205,7), HIV-2 (Isolate GHANA-1), HIV-2 (Isolate ROD); Simian AIDS retrovirus (SRV-1) such as, SIV (AGM155), SIV (AGM266 isolate), SIV (AGM3 isolate), SIV (AGM385 isolate), SIV (F236/SMH4 isolate, Sooty Mangabey), SIV (TyO-1 isolate) and SIVagm; Simian immunodeficiency virus, such as, SIV (1A11 isolate), SIV (isolate African mandril), SIV (AGM/clone Gri-1), SIV (vervet), SIV (Tantalus), SIV, STM isolate, SIV, 17E-Cl, SIV Qu, SIVdeb, SIVmac, SIVMND, SIVmon, SIVsm; Simian immunodeficiency virus 2; and Simian-Human immunodeficiency virus.

In specific methods, the envelope polypeptide is from HIV-2. For example, in one method, an HIV-2 envelope polypeptide or functional variants thereof is used. By "HIV-2 envelope polypeptide" or "envelope encoded by an HIV-2 polynucleotide" is intended the form of the HIV-2 envelope polypeptide or polynucleotide encoding the same in the HIV-2 viral isolate 7312A. The amino acid of the envelope polypeptide of the HIV-2 isolate 7312A is set forth in FIGS. 4 and 7 and SEQ ID NO:2. The nucleotide sequence encoding the envelope polypeptide of the HIV-2 isolate 7312A is set forth in SEQ ID NO:21.

Variants of the HIV-2 envelope polypeptide are biologically active, that is they continue to possess the desired biological activity of the native protein, that is, they continue to interact with CD4 and/or facilitate virus fusion and/or facilitate viral entry into a permissive cell. It is further recognized that the viral envelope polypeptide is produced as a precursor (gp160) that is subsequently cleaved into two parts, gp120 which binds CD4 and chemokine receptors, and gp41, which is anchored in the viral membrane and mediates viral fusion. Variants of the HIV-2 envelope polypeptide encompass fragments of HIV-2 envelope including, for example, gp41, gp120 or any other fragment that retains the necessary activity. The amino acid sequence comprising gp41 and gp120 is denoted in FIGS. 4, 6, 7 and 8. Various domains of the HIV-2 envelope polypeptide include gp41 (about amino acids 515-857 of SEQ ID NO:2), gp120 (about amino acids 20-514 of SEQ ID NO:2). Additional domains of HIV envelope polypeptides are discussed in further detail in Burton et al. (2004) *Nature Immunology* 5:233 and Zwick et al. (2004) *Nature Medicine* 10: 133, both of which are herein incorporated by reference.

Variants of HIV-2 envelope polypeptide are known. See, for example, FIGS. 4 and 7 which provides the amino acid sequence of envelope polypeptides from various HIV-2 strains, including UC1, UC2, and ROD-B. Assays to measure HIV-2 envelope activity include, for example, envelope binding assays to CD4 and cell fusion assays. Such methods are described in detail in Martin et al. (2003) *Nature Biotechnology* 21:71-76, herein incorporated by reference in its entirety.

In another method an SIV envelope polypeptide or functional variants thereof is used. By "SIVsm envelope polypeptide" or "envelope encoded by an SIVsm envelope polynucleotide" is intended the form of the SIVsm envelope polypeptide or polynucleotide encoding the same in SIVsm PBJ1.9. The amino acid of the envelope polypeptide of the SIVsm PBJ1.9 is set forth in SEQ ID NO:3 and the nucleotide sequence encoding this polypeptide is set forth in SEQ ID NO:22. In other methods, a SIVsm envelope polypeptide, polynucleotide, or a functional variant thereof. See, also, Israel et al. (1993) *AIDS Res. Hum. Retroviruses* 9:277-286; Hirsch et al. (1998) *Nat. Med.* 4(12):1401-8; Mahalingam et al. (2001) *J. Virol.* 75(1):362-74, each of which is herein incorporated by reference.

By "SIVagm envelope polypeptide" or "envelope encoded by an SIVagm polynucleotide" is intended the form of the SIVagm envelope polypeptide or polynucleotide encoding the same in SIVagmVer155. The amino acid sequence of the envelope polypeptide of SIVagmVer155 is set forth in SEQ ID NO:4. See, also, Johnson et al. (1990) *J. Virol.* 64 (3), 1086-1092, herein incorporated by reference. Other envelope polypeptides from SIVagm are known. For example, the amino acid sequence for the envelope polypeptide from SIVagmTAN is provided in SEQ ID NO:5. See, also, Soares et al. (1997) *Virology* 228 (2): 394-399.

Variants of the SIV envelope polypeptide are biologically active, that is they continue to possess the desired biological activity of the native protein, that is, they continue to interact with CD4 and/or facilitate virus fusion and/or facilitate viral entry into a permissive cell. Variants of the SIV envelope polypeptides encompass fragments of SIV envelope including, for example, gp41, gp120 or any other fragment that retains the necessary activity. The amino acid sequence of gp41 and gp120 are denoted in FIGS. 4, 6, 7 and 8.

In still other methods, the envelope polypeptide is associated with a retrovirus. Any retrovirus can be used including lentiviruses and primate lentiviruses. The term HIV refers to all strains, isolates, and molecular clones of human immunodeficiency virus. Many different retroviruses can be used in the methods of the invention. For example, in one method, the retrovirus having the HIV-2 envelope polypeptide comprises an HIV-2 virus, including any primary HIV-2 isolates, laboratory strains, or molecular clones derived there from. In addition, the HIV-2 can be infectious or non-infectious. HIV-2 viruses include, but are not limited to, UC1, HIV-2 MS, CBL 20. In another method, the HIV-2 virus employed is HIV-2 7312A one of its molecular clones including, for example, pJK7312A or V434M. V434M has a single amino acid change from V→M at amino acid 434 in the envelope polypeptide. The clone has particular sensitivity in the detection of CD4 induced antibodies. In still other methods, the HIV-2 virus is HIV-ST or its molecular clone pJSP4-27(ST/SXB1). See, the Experimental section for a complete description of these particular molecular clones. See, also Gao et al. *Nature* (1992) 358:495-499 and found in GenBank Accession No. L36874 and in the Los Alamos HIV database operated by the University of California at ".hiv.land.gov/content/index", herein incorporated by reference. Similarly, a retrovirus having the SIV or SRV-1 envelope polypeptide can comprise an SIV or an SRV-1 virus, including any primary SIV or SRV-1 isolates, laboratory strains, or molecular clones. In addition, the SIV or SRV-1 can be infectious or non-infectious.

In still other methods, the retrovirus having the envelope polypeptide or the functional variant thereof comprises a retrovirus that has been pseudotyped with the envelope polypeptide from the primate lentivirus that is not HIV-1 or functional variant thereof. Retrovirus that can be used in these methods include, but are not limited to, lentiviruses, such as, bovine lentivirus, equine lentivirus, feline lentivirus, ovine/caprine lentivirus, and primate lentivirus. Primate lentivirus that can be used include, HIV-1, HIV-2, HIV-3, SRV-1, SIV, SIV-2 and simian-Human immunodeficiency virus. In specific methods, the SIVsm and SIVagm are used.

In addition, the retrovirus employed in the methods may be infectious or non-infectious. For example, non-infectious HIV-1 strains include 8E5/LAV virus (Folks et al. (1986) *J. Exp. Med.* 164:280-290; Lightfoot et al. (1986) *J. Virol.* 60:771-775 and Gendelman et al. (1987) *Virology* 160:323-329), and HIV-1 JR-FL. In still other methods, the virus pseudotyped with the envelope polypeptide from the primate lentivirus or the functional variant thereof is an infectious laboratory-adapted or a primary isolate of HIV-1, HIV-2, SIV, or SRV-1. See, for example, Haddrick et al. (1996) *J. Virol. Methods* 61:89-93 and Yamshchikov et al. (1995) *Virology* 21:50-58. It is further recognized that sequences from many strains of retroviruses are publicly available on Genbalik and primary field isolates of HIV are available from the National Institute of Allergy and Infectious Diseases (NIAID). Such strains are also available from the World Health Organization (WHO) [Network for HIV Isolation and Characterization, Vaccine Development Unit, Office of Research, Global Programme on AIDS, CH-1211 Geneva 27, Switzerland]. Methods of pseudotyping viruses are known in the art. See, for example, US Application No. 20040033604, U.S. Application No. 200330203489, Schauber et al. (2004) *Gene Ther* 11:266-75, and Kafri et al. (2004) *Methods Mol. Biol.* 246: 376-90.

The envelope polypeptide employed in specific methods of the invention comprises at least one epitope that is recognized by an HIV-1 binding antibody. Various methods to determine if such an epitope is present in the envelope polypeptide are discussed in detail elsewhere herein. It is recognized that the epitope recognized by the HIV-1 binding antibody can be homologous or heterologous to the envelope polypeptide that it is contained in. A homologous epitope for an HIV-1 binding antibody is present in the native envelope polypeptide. A heterologous epitope for an HIV-1 binding antibody is not present or found in an alternative location in the native envelope polypeptide. Polypeptides comprising such heterologous epitopes are referred to herein as "chimeric polypeptides."

A variety of epitopes for HIV-1 binding antibodies are known in the art. Such epitopes are found both in gp160, gp120, gp41. See, for example, *HIV Molecular Immunology* (2002) Korber et al. ed., Los Alamos National Laboratory, Theoretical Biology and Biophysics, Los Alamos, N. Mex. LA-UR 03-5816, which is herein incorporated by reference in its entirety. In specific embodiments, the epitope of the HIV-1 binding antibody is in gp41. For example, the epitope in the N-terminal hydrophobic fusion peptide of gp41 (about amino acids 512 to about 527 of SEQ ID NO:10), the disulfide-loop region of gp41 that links the N-HR and C-HR regions (about amino acids 581 to about 628 of SEQ ID NO:10), the N-HR region of gp41 (about amino acids 546 to about 581 of SEQ ID:10), the C-HR of gp41 (about amino acids 628 to about 661 of SEQ ID NO: 10), the membrane proximal region of gp41 (about amino acids 657 to about amino acids 684 of SEQ ID NO:10).

As used herein, an "MPER region" comprises the MPER region found in HIV-1 YU-2 (i.e., N-LALDKWASLWN-WFDITKWLWYIK-C (SEQ ID NO:38)). A functional variant of an MPER region will continue to be recognized by an HIV-1 binding antibody. Method to assay for the binding of the HIV-1 binding antibody are discussed elsewhere herein as are methods to determine if the variant sequence is immunologically equivalent. Such variants can include internal and/or terminal additions, deletions, and/or substitutions. The variants can differ by 1, 2, 3, 4, 5, 6, 7, 8, 9, 10, 11, 12, 13, 14, 15, or more amino acids. Variants of the MPER region are known. See, for example, FIG. 8 which provides the MPER region of HXB2C, ST, and UC1. Additional variants of the MPER region are shown in FIG. 11.

Functional variants of the MPER region comprise substitutions, additions, and/or deletions (including internal or terminal alterations or both).

Epitopes within the membrane proximal region of gp41 can be found, for example, between about amino acids 657 to 675, about amino acid 670 to 684, about amino acids 665 to about 680, or about amino acids 667 to about 681 of SEQ ID NO:10. See, Follis et al. (2002) *J. of Virology* 76:7356-7362 for additional domains of gp41 that are of interest. In other embodiments, epitope of the HIV-1 binding antibody is found in the bridging sheet, variable loop 1, variable loop 2, variable loop 3, variable loop 4, the chemokine receptor binding site, or the CD4 binding site. See, for example, FIG. 4 which outlines the various domains of gp120 in the HXB2 HIV-1 isolate. It is recognized an entire domain of the HIV-1 envelope protein may be inserted into the heterologous envelope polypeptide or alternatively, any fragment of the domain from the HIV-1 envelope polypeptide can be used as the epitope for the HIV-1 binding antibody.

While any epitope for an HIV-1 binding antibody may be used, of particular interest is a neutralizing epitope found in the HIV-1 envelope polypeptide. Epitopes of interest include, but are not limited to, the 4E10 epitope (SEQ ID NO:15), the Z13 epitope (SEQ ID NO:15) and the 2F5 epitope (SEQ ID NO:16). See, for example, U.S. Publication No. 20030157063, Muster et al (1993) *J. Virol.* 67:6642-6647, Zwick et al. (2001) *J. Virology* 75:10892-10905, Ferrantelli et al. (2002) *Curr. Opin. Immunol.* 14:495-502, and Wang et al. (2003) *Curr. Phamm. Des.* 9:1771-87. Each of these epitopes is denoted in FIG. 8. Alternatively, the entire neutralization 2F5/4E10/Z13 cluster could be employed. Additional epitopes for HIV-1 binding antibodies include the epitope located at amino acid number 662 to 667 of gp41 of the HIV-1 isolate BH10 (GenBank Acc No. M1565) with the number as described in the Swissprot database entry ENV$HIV10; the epitope located at amino acid position 79 to 184 or amino acid position 326 to 400 of the processed gp120 of HIV-1 isolate BH10 (GenBank Acc. No. M15165, with numbering as described in Swissprot database entry ENV$SHIV10). See, for example, U.S. Pat. No. 6,268,484. See, also, Rizzuto et al. (2000) *AIDS Res Hum Retroviruses* 16:741-749 and Xiang et al. (2002) *AIDS Res Hum Retroviruses* 18:1207-1217 which characterize the HIV-1 gp120 structures implicated in the CCR5 and CD4-induced antibodies. Epitopes for 17b, 48d, b12, and 2G12 are also known. See, for example, Rizzuto et al. (1998) *Science* 280:1949-1953, Thali et al. (1993) *J. Virol.* 67:3978-3988, and Trkola et al. (1996) *J. Virol.* 70:1100-1108. A review of additional characterized epitopes for HIV-1 binding antibodies and their location in the HIV-1 envelope polypeptide can be found in *HIV Molecular Immunology* (2002) Bette et al. eds., Los Alamos National Laboratory, Theoretical Biology and Biophysics, Los Alamos, N. Mex. LA-UR 03-5816. The contents of each of these references in herein incorporated by reference in their entirety.

It is further recognized that immunological equivalent epitopes for the HIV-1 binding antibodies discussed above are known and can be used in the methods and compositions of the invention. Immunologically equivalent epitopes for 2F5 are known. See, for example, U.S. Application Publication No. 20030157063, Kattinger et al. (1992) Septime Colloque des Cent Gardes, 299-303, EP-0570357, and Zwick et al. (2001) *J. Virology* 75:10892-10900 which disclose immunologically equivalent epitopes of the 2F5 epitope. Such immunologically equivalent epitopes, while differing in their amino acid sequence continue to be recognized by the 2F5 monoclonal antibody (Virus Testing Systems, Houston, Tex., USA). Immunologically equivalent epitopes for 4E10 and Z13 are also known. See, for example, Zwick et al. (2001) *J. Virology* 75:10892-10900. Again, such immunologically equivalent epitopes, while differing in their amino acid sequence continue to be recognized by the 4E10 monoclonal antibody or the Z13 antibody. Accordingly, immunologically equivalent epitopes can differ from the epitope set forth in SEQ ID NO: 15 and 16 by at least 1, 2, 3, 4, 5, 6, 7, 8 or more amino acids. The differences can be generated by amino acid substitutions, deletions and insertions. Method to determine if two epitopes are immunologically equivalent are known in the art. See, for example, U.S. Application Publication No. 20030157063, EP-0570357 and Zwick et al. (2001) *J. Virology* 75:10892-10900, all of which are herein incorporated by reference.

Many HIV-1 binding antibodies are known in the art and can be employed in the methods and compositions of the invention. The term "antibody" as used herein includes monoclonal, polyclonal, chimeric, single chain, bispecific, simianized, and humanized or primatized antibodies as well as Fab fragments, such as those fragments which maintain the binding specificity of the antibodies to the epitope of the HIV-1 envelope polypeptide. Accordingly, the invention contemplates the use of single chains such as the variable heavy and light chains of the antibodies. Generation of any of these types of antibodies or antibody fragments is well known to those skilled in the art. Various CD4-induced antibodies are known in the art and can be employed in the methods of the invention, including, but not limited to 17b (Zhang et al. (1999) *Biochemistry* 38:9405-16), 21c, 19e, E51 (Xiang et al. (2003) *Virology* 315:124), X5 (Darbha et al. (2004) *Biochemistry* 43:1410), ED49, and ED47.

In the methods of the invention, the envelope polypeptide or the functional variant thereof is contacted with composi-tions that may comprise the HIV-1 binding antibody. It is recognized that such methods of the invention will be carried out in an appropriate buffer and at the appropriate temperature to promote the desired interaction and to allow the necessary activities to be measured. One of skill will be capable of determining the appropriate buffers and temperatures that will promote the desired interaction. See, for example, Moore et al. (1990) *AIDS* 4:297-303 and Dey et al. (2003) *Journal of Virology* 77:2859-2865. In one embodiment, the detection of HIV-1 binding antibodies is performed under the conditions outlined in Wei et al. (2003) *Nature* 422:307-312, herein incorporated by reference.

As discussed above, in one method of the invention, HIV-1 binding antibodies (i.e., binding antibodies, neutralizing antibodies, and/or CD4-induced antibodies) in a subject infected with HIV-1 are detected. In other methods, the titer of the HIV-1 binding antibody in a sample is determined. In still other methods, the HIV-1 binding antibody is isolated and characterized. The subject can be any mammal infected with HIV-1 including humans and non-humans, such as, monkeys. Several methods can be used to detect the presence of the HIV-1 binding antibodies. For example, detection of the antibodies can be determined by assaying for a decrease in infectivity of the retrovirus (i.e., the neutralization of the retrovirus). Any statistically significant decrease when compared to the appropriate control indicates that HIV-1 neutralizing antibodies are present in the bodily fluid of said patient. Methods to determine the infectivity of the retrovirus having the envelope polypeptide have been discussed in detail elsewhere herein. Other methods to detect the HIV-1 binding antibodies include competitive binding assays with the chemokine receptors (i.e., CCR5 and CXCR4) or with characterized HIV-1 binding antibodies, or the use of cell fusion assays. Each of these assays is described in detail, for example, in Martin et al. (2003) *Nature Biotechnology* 21:71-77.

As discussed above, methods are provided for the detection of CD4-induced antibodies, which employs the use of an effective concentration of a soluble CD4/envelope complex. CD4 is a member of the immunological superfamily and it comprises an extracellular region comprising four immunoglobulin-like domains (D1-D4), a membrane spanning region, and a charged cytoplasmic domain. The cDNA encoding CD4 is found in Maddon et al. (1985) *Cell* 42:93 and in Genbank Accession No. RWHUT4, both of which are herein incorporated by reference. The full length CD4 is set forth in SEQ ID NO:6. In human CD4, amino acid residues from about 30 to about 60 play a role in the interaction of CD4 with HIV-1 gp120. Residue Phe-43 of hCD4 is believed to play a role in the CD4/gp120 interaction. See, for example, Clayton et al. (1988) *Nature* 22:363-6, Jameson et al (1998) *Science* 240:1335-1339, Piatier-Toneua et al. (1991) *PNAS* 88:6858-6862.

As used herein, "soluble CD4" or "sCD4" refers to the human form of CD4 that comprises a CD4 polypeptide that lacks a portion of the hydrophobic anchor domain such that the soluble CD4 or biologically active variants thereof are soluble in water-based pharmaceutical preparations (or pharmaceutically acceptable solvents or compositions which include components in addition to water) and in physiological fluids, including plasma, at a level which is sufficient to achieve an effective concentration. As used herein, by "sCD4" is intended the form of sCD4 set forth in SEQ ID NO:1.

Variants of the soluble CD4 polypeptide are biologically active, that is they continue to possess the desired biological activity of the native sCD4 protein, that is, they continue to interact with the envelope polypeptide and/or a functional variant thereof, wherein the interaction of the sCD4 variant with the envelope polypeptide or the functional variant thereof exposes or increases the accessibility of a sCD4-inducible epitope on the envelope polypeptide or the functional variant thereof. Variants of sCD4 proteins include those in which part or the entire transmembrane domain of the primary structure of CD4 has been deleted, for example through truncation of the coding sequence. The cytoplasmic domain of the protein may likewise be deleted without the loss of the desired biological activity of HIV envelope binding.

CD4 and recombinant CD4 that is synthesized in recombinant eukaryotic cells is a glycoprotein. It is recognized that the native full-length CD4, the sCD4, or the functional variant thereof can be glycosylated. See, Maddon et al. (1985) *Cell* 42:93 and U.S. Pat. No. 5,234,905. It is further recognized that the exact oligosaccharide structure of the glycoprotein may vary with respect to sugars present, the glycosylation enzymes present and the relative proportions of each according to the choice of the particular eukaryotic cell in which the recombinant CD4 (or soluble CD4) is synthesized. Soluble CD4 molecules capable of being glycosylated when synthesized in appropriate host cells are described in Smith et al. (1987) *Science* 238:1704; Fisher et al. (1988) *Nature* 331:76; Hussey et al. (1988) *Nature* 331:78; EP Publication No. 385 909; Deen et al. (1988) *Nature* 331:82-84; all of which are incorporated by reference herein.

Functional variants of soluble CD4 include, for example, conservative amino acid alterations to the polypeptide of SEQ ID NO:1 along with functional variants that interact with the external envelope glycoprotein, gp120, derived from HIV. Additional functional variants of sCD4 include various peptide variants such as CD4M9 (a 28 amino acid peptide) and CD4M33. See, for example, Martin et al. (2003) *Nature Biotechnology* 21:71-76, herein incorporated by reference. In addition, a tetrameric form of sCD4 (Allway et al. (1995) *AIDS Res. Hum. Retroviruses* 69:6609-6617) and a dodecameric form of sCD4 (Arthos et al. (2002) *J. Biol. Chem.* 277:11456-11464) can also be employed. Other functional variants are disclosed in WO-97/08574, Chao et al. (1989) *J. Biol. Chem.* 264:5812, Peterson and Seed (1988) *Cell* 54:65-72, U.S. Pat. Nos. 5,767,022, and 5,234,905, all of which are herein incorporated by reference.

As used herein, an "effective concentration" of a sCD4/envelope complex or of a soluble CD4 or a functional variant thereof comprises a concentration sufficient to create, expose and/or increase the accessibility of an epitope recognized by a soluble CD4-induced antibody. An effective concentration of soluble CD4 or an active variant thereof include final soluble CD4 concentrations of about 0.1 nM, 1 nM, 5 nM, 10 nM, 20 nM, 30 nM, 40 nM, 50 nM, 60 nM, 70 nM, 80 nM, 90 nM, 100 nM, 120 nM, 140 nM, 160 nM, 180 nM, 200 nM, 220 nM, 220 nM, 260 nM, 280 nm, 300 nM, 350 nM, 400 nM, 500 nm, 600 nm, 700 nm, 800 nm, 900 nm, 1000 nm, 1200 nm, 1500 nm, 1800 nm, 2000 nm, 2500 nm, 4000 nm or greater. In other embodiments, the effective concentration of soluble CD4, or the functional variants or mimic thereof include final concentrations between about 0.1 nM and about 1 mM, between about 1 nM and 5000 nM, between about 1 nM and 4000 nM, between about 1 nM and 2000 nM, between about 1 nm and 10001 nM, between about 280 nM and 450 nm, and between about 1 nm and 100 nm. One of skill will recognize that depending on the sCD4 or functional variant thereof and the specific assay employed, the effective concentration of may vary.

Methods to determine if an effective concentration of soluble CD4 has been provided include, but are not limited to, performing a neutralization assay in which the target virus is incubated in the presence of soluble CD4 or a functional variant thereof. The mixture is exposed to a CD4-induced antibody. The infectivity of the target virus is determined in the presence and absence of the soluble CD4 or the functional variant thereof. An effective concentration of soluble CD4 or its functional variant will be sufficient to neutralize the virus. Methods to assay for viral neutralization are discussed elsewhere herein. Alternatively, methods to determine if an effective concentration of soluble CD4 or an effective concentration of a sCD4/envelope complex has been provided also includes various binding assays, for example, with the chemokine receptors or with a characterized CD4-induced antibody. Such methods are discussed elsewhere herein.

When CD4-induced antibodies are to be detected, the sCD4 or the functional variant thereof is provided under conditions that allow for the interaction of the sCD4 or the functional variant thereof with the envelope polypeptide or the functional variant thereof from the non-HIV-1 primate lentivirus. Thus, methods of the invention will be carried out in an appropriate buffer and at the appropriate temperature to promote the desired interaction and to allow the necessary activities to be measured. In the methods disclosed herein, the order in which the sCD4 or variant thereof and the sample containing the CD4-induced antibodies are provided in the methods disclosed herein can be varied. For example, in some methods, the sCD4/envelope complex is formed prior to the addition of a sample bodily fluid sample or a sample having the CD4-induced antibody. In specific methods, the sCD4 is incubated with the envelope polypeptide to form the sCD4/envelope complex for any period of time sufficient to allow for the desired interaction including, for example, 0.1 hr, 0.5 hr, 1 hr, 1.5 hr or greater. In other methods, the sample having the CD4-induced antibody is contacted with the envelope polypeptide prior to the addition of the sCD4 or the variant thereof. In yet other methods, the addition of sCD4, the envelope polypeptide, and the CD4-induced antibodies occurs simultaneously.

In still further methods, soluble CD4 is not required to expose, create or increase the accessibility of the epitope that is recognized by the CD4-induced antibody. In this method, a variant of an HIV envelope is employed which is capable of interacting with the CD4-induced antibody in the absence of sCD4. For example, the variant envelope polypeptide could have the first, the second, or both variable loops removed. This variant would expose, create or increase the accessibility of an epitope recognized by a CD4-induced antibody in the absence of sCD4.

As discussed above, the methods and compositions disclosed herein can employ variant polynucleotides and polypeptides of the envelope polypeptide and of the soluble CD4 peptide. As used herein, "variants" is intended to mean substantially similar sequences. A "variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. As used herein, a "native" polynucleotide or polypeptide comprises a naturally occurring nucleotide sequence or amino acid sequence, respectively. As defined herein, the "native" envelope polypeptide of HIV-2 or polynucleotide encoding the same is from the HIV-2 isolate 7312A (SEQ ID NO:2 and 21), the "native" envelope polypeptide of SIVsm or the polynucleotide encoding the same from SIVsmPBj1.9 (SEQ ID NO:3 and 22), the "native" envelope polypeptide of SIVagm or the polynucleotide encoding the same is from SIVagmVer155 (SEQ ID NO:4) and 22 or SIVagmTAN (SEQ ID NO:5 and 24), and the "native" sCD4 polypeptide is set forth in SEQ ID NO:1. Variant proteins encompassed by the present invention are biologically active, that is they continue to possess the desired biological activity of the native protein activity as described herein for envelope and sCD4. Such variants may result from, for example, genetic polymorphism or from human manipulation. Biologically active variants of a native envelope polypeptide and/or a native soluble CD4 polypeptide employed in the methods of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

A fragment of a biologically active portion of an envelope polypeptide and/or a soluble CD4 polypeptide of the invention will encode at least 15, 25, 30, 50, 100, 150, 200, or 250, 300, 350, 400, 450, 500, 550, 600, 650, 700, 750, 800, 850, 900, 1000, 1,200 contiguous amino acids, or up to the total number of amino acids present in a full-length HIV-2 envelope polypeptide and/or a soluble CD4 polypeptide of the invention.

For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the envelope polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode an envelope protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO:21, 22, 23, or 24 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

A fragment of an envelope polynucleotide may encode a biologically active portion of an envelope polypeptide. A biologically active portion of an envelope polypeptide can be prepared by isolating a portion of one of the envelope polynucleotide of the invention, expressing the encoded portion of the envelope protein (e.g., by recombinant expression in vitro), and assessing the activity of the portion of the envelope polypeptide. Polynucleotides that are fragments of an envelope nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, or 1,400 more contiguous nucleotides, or up to the number of nucleotides present in a full-length envelope polynucleotide disclosed herein.

Variant envelope polypeptides and/or a soluble CD4 polypeptide of the invention, as well as polynucleotides encoding these variants, are known in the art and are discussed in further detail elsewhere herein. The polypeptide employed in the methods of the invention may be altered in various ways including amino acid substitutions, deletions, truncations, and insertions. Methods for such manipulations are generally known in the art. As discussed below, variant polypeptides or polynucleotides of the invention can comprise heterologous epitopes for HIV-1 binding antibodies. For example, amino acid sequence variants and fragments of the envelope polypeptide and/or a soluble CD4 polypeptide can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the polypeptides and polynucleotides employed in the methods of the invention encompass naturally occurring sequences as well as variations and modified forms thereof. Such variants will continue to possess the desired activity for envelope or sCD4 as discussed elsewhere herein. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated for sCD4 functional variants by the ability to create, expose or render accessible CD4-induced epitopes on the envelope polypeptide. The activity can be evaluated for functional variants of the envelope polypeptides by the ability to interact with CD4 and/or facilitate virus fusion and/or facilitate viral entry into a permissive cell. See, for example, Martin et al (2003) *Nature Biotechnology* 21:71-76, herein incorporated by reference.

Methods of alignment of sequences for comparison are well known in the art. Thus, the determination of percent sequence identity between any two sequences can be accomplished using a mathematical algorithm. As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSLUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

Methods are further provided for a diagnostic assay to monitor HIV-induced disease in a subject and/or to monitor the response of the subject to immunization by an HIV vaccine. By "HIV-induced disease" is intended any disease caused, directly or indirectly, by HIV. An example of an HIV-induced disease is acquired autoimmunodeficiency syndrome (AIDS). The method comprises providing an envelope polypeptide or a functional variant thereof that is not from HIV-1 where the envelope polypeptide further comprises at least one epitope recognized by an HIV-1 binding antibody (i.e., binding, neutralizing, CD4-induced). The envelope polypeptide is contacted with an amount of bodily fluid from the subject; and, the HIV-1 binding antibodies in the bodily fluid of the subject are detected. The detection of the HIV-1 binding antibodies allows the HIV disease in the subject to be monitored. In addition, the detection of the HIV-1 binding antibody also allows the response of the subject to immunization by a HIV vaccine to be monitored. In still other methods, the titer of the HIV-1 binding antibodies is determined. In other methods, the envelope polypeptide is associated with a retrovirus. In this method, a composition comprising a retrovirus having the non-HIV-1 primate lentivirus envelope polypeptide or a functional variant thereof is provided and contacted with the bodily fluid from the subject, and the HIV-1 binding antibodies in the bodily fluid of said patient are detected.

In specific embodiments, the response of the subject to immunization against HIV comprises a 4E10 neutralization response. By "4E10 neutralization response" is intended the increased presence, when compared to an appropriate control, of HIV-1 binding antibodies that interact with the 4E10 epitope. Similarly, a 2F5 or Z13 neutralization response could also be detected.

When a CD4-induced antibody is to be detected, an effective concentration of a soluble CD4/envelope complex which comprises a soluble CD4 or a functional variant thereof and the envelope polypeptide or a functional variant thereof is contacted with an amount of bodily fluid from said subject. The CD4-induced antibodies are detected, and HIV disease in the subject or the response of the subject to immunization by a HIV vaccine is thereby monitored.

Further provided are methods to determine an epitope for an HIV-1 binding antibody. The method comprises providing a population of envelope polypeptides which are not from HIV-1, in which members of the population of the envelope polypeptides comprise at least one epitope recognized by an HIV-1. Members of the population are substantially identical to one another. In specific embodiments, each of the envelope polypeptides in the population is selected from the group consisting of an HIV-2 envelope polypeptide and a functional variant of the HIV-2 envelope polypeptide. In other embodiments, each of the envelope polypeptides in the population is selected from the group consisting of a SIV envelope polypeptide and a functional variant of the SIV envelope polypeptide. The population of envelope polypeptides is contacted with the HIV-1 binding antibody, and the envelope polypeptide or polypeptides in the population that is/are recognized by the HIV-1 binding antibody are determined. The envelope polypeptides in the population can be mixed together and contacted with the HIV-1 binding antibody or alternatively, each envelope polypeptide in the population can be contacted separately by the HIV-1 binding antibody. A comparison of at least one of the amino acid sequences of the envelope polypeptide in the population that binds the HIV-1 antibody with at least one of the amino acid sequences of the envelope polypeptides in the population that do not bind the HIV-1 antibody will allow the epitope for the HIV-1 binding antibody to be determined.

By "substantially identical" is intended the polypeptides in the population have at least 70%, 75%, 80%, 85%, 90%, 91%, 92%, 93%, 94%, 95%, 96%, 97%, 98%, or 99% amino acid sequence identity to one another. Methods to determine percent identity are discussed elsewhere herein. In other embodiments, substantially identical polypeptides will differ by 20, 15, 14, 13, 12, 11, 10, 9, 8, 7, 6, 5, 4, 3, 2, or 1 amino acids.

Additional methods include an assay to determine the binding characteristics of an HIV-1 binding antibody (i.e., the epitope that the HIV-1 binding antibody interacts with). The method comprises providing an envelope polypeptide or a variant thereof that is not from HIV-1, which comprises an epitope recognized by an HIV-1 binding antibody and contacting the envelope polypeptide with a composition comprising a candidate HIV-1 binding antibody. Assays are performed to determine if the candidate HIV-1 binding antibody recognizes the HIV-1 epitope present in the envelope polypeptide. In this manner, one can characterize the binding properties of the candidate HIV-1 binding antibody. Various candidate HIV-1 binding antibodies are known in the art. Methods are also known to isolate candidate HIV-binding antibodies from a variety of sources including naïve libraries, modified libraries, and libraries produced directly from human donors exhibiting an HIV-specific immune response. See, for example, U.S. Application No. 0030187247.

Methods are also provided to neutralize non-HIV-1 primate lentiviruses, such as HIV-2, SIV, and SRV-1. The method comprises providing a compositions comprising the non-HIV-1 primate lentiviruses and providing an isolated HIV-1 neutralizing antibody. In specific methods, the neutralizing antibody was elicited by HIV-1. In other methods, the neutralizing antibody is from a patient infected with HIV-1. In specific embodiments, the HIV-1 neutralizing antibody is a CD4-induced antibody. In this embodiment, the method comprises providing a composition comprising said HIV-2 or said SIV and providing to the composition an effective concentration of soluble CD4 (sCD4) or a functional variant thereof. An isolated CD4-induced antibody is provided to the composition. Methods to assay for viral neutralization are described elsewhere herein.

Methods are further provided to alter the neutralization potential of a CD4-induced antibody elicited by HIV-1. The method comprises providing a soluble CD4/envelope complex and providing to the soluble CD4/envelope complex a CD4-induced antibody elicited by a HIV-1, and, thereby altering the neutralization potential of the CD4-induced antibody. In still other methods the envelope polypeptide is associated with a retrovirus. In this method, a composition comprising a retrovirus having a non-HIV-1 primate lentivirus envelope polypeptide or a functional variant thereof and an effective concentration of a soluble CD4 polypeptide or a functional variant thereof is provided. A CD4-induced antibody elicited by HIV-1 is also provided to the composition, and the neutralization potential of the CD4-induced antibody is thereby altered. By an "altered" neutralization potential of a CD4-induced antibody is intended any modification (an increase or a decrease) in the ability of the antibody to neutralize a retrovirus having the non-HIV-1 primate lentivirus envelope polypeptide or an active variant thereof when compare to the neutralization activity of the antibody in the absence of soluble CD4 or the functional variant of sCD4. Alteration of neutralization potential can be assayed using the various assays described herein. In specific methods, the sCD4 inducible antibody is from a subject infected with HIV-1.

Further included is a method to identify a soluble CD4 mimic. By "soluble CD4 mimic" is intended any compound that mimics the activity of soluble CD4 (i.e., the compound interacts with the envelope polypeptide or a functional variant thereof, wherein the interaction exposes a CD4-induced epitope on the envelope polypeptide or the functional variant thereof). The compound can include a small inorganic molecule or any organic molecule.

The method comprises providing an envelope polypeptide or a functional variant from a non-HIV-1 lentivirus, contacting the envelope polypeptide or a variant thereof with a candidate compound; and determining if the candidate compound interacts with the envelope polypeptide or functional variant thereof. The interaction of the candidate compound and the envelope polypeptide or functional variant thereof increases the accessibility of an epitope or creates the epitope on the envelope polypeptide or the functional variant thereof. In this method, the created or exposed epitope is recognized by a CD4-induced antibody. Methods of determining whether a particular compound mimics soluble CD4 have been described elsewhere herein. See, also, in Martin et al. (2003) *Nature Biotechnology* 21:71-76, herein incorporated by reference.

In other methods, the envelope polypeptide is associated with a retrovirus. In this method, a composition comprising a retrovirus having the non-HIV-1 primate lentivirus envelope polypeptide or a functional variant thereof is provided. The retrovirus is contacted with a candidate compound; and it is determined if the candidate compound interacts with the retrovirus. The interaction of the candidate compound and the retrovirus creates, exposes and/or increases the accessibility of a CD4-induced epitope on the envelope polypeptide or the functional variant thereof.

Candidate compounds that may be screened to identify soluble CD4 mimics according to the methods of the invention include any molecule, for example, small inorganic molecules and small organic molecules (e.g., molecules obtained from combinatorial and natural product libraries). Such molecules include, for example, polypeptides (including antibodies and peptides), as well as, nucleic acid molecules, or polysaccharides. It is recognized that the candidate compounds encompass numerous chemical classes.

As will be appreciated by those in the art, candidate compounds can be obtained from a wide variety of sources, including libraries of synthetic and natural compounds. Thus, the methods disclosed herein provide a rapid and easy method for screening any library of candidate compounds. Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al (1993) *Science* 261:1303; Carell et al. (1994) *Angew. Chem. Int. Ed. Engl.* 33:2059; Carell et al. (1994) *Angew. Chem. Int. Ed. Engl.* 33:2061; Gallop et al (1994) *J. Med. Chem.* 37:1233; and Ghose and Vishwanadhan, eds. (2001) *Combinatorial Library Design and Evaluation: Principles, Software Tools, and Applications in Drug Discovery* (Marcel Dekker, New York), WO94/24314, and WO94/24314, each of which is herein incorporated by reference in its entirety.

Compositions of the invention include chimeric polypeptides comprising an amino acid sequence encoding an envelope polypeptide or a variant thereof that is not from HIV-1, wherein the amino acid sequence further comprises a heterologous epitope recognized by an HIV-1 binding antibody. In specific embodiments, the epitope recognized by the HIV-binding antibody is a neutralizing HIV-1 epitope, a CD4-induced epitope, or a neutralizing CD4-induced epitope. As used herein, a "heterologous epitope" refers to a domain that is not present in or is found in an alternative location in the native form of the polypeptide or polynucleotide it is contained in. The heterologous epitope can be native to the HIV-1 envelope polypeptide or alternatively, the epitope can be synthetically derived, so long as the epitope continues to be recognized by the HIV-1 binding antibody. Polypeptides or polynucleotides comprising such heterologous epitopes are referred to herein as "chimeric polypeptides" or "chimeric polynucleotides," respectively. Heterologous epitopes which can be employed in the chimeric polypeptides of the invention are discussed elsewhere herein.

The heterologous epitope or the heterologous domain containing the epitope can be of any length including about 2 to 7 amino acids, about 5 to about 10 amino acids, about 11 to about 20 amino acids, about 21 to about 30 amino acids, about 31 to about 40 amino acids, about 41 to about 50 amino acids, about 51 to about 60 amino acids, about 61 to about 70 amino acids, about 71 amino acids to about 80 amino acids, about 81 to about 90 amino acids, about 91 to about 100 amino acids, about 101 to about 110 amino acids, or longer. The heterologous epitope can be placed anywhere in the envelope sequence, as long as the chimeric polypeptide retains the activity of the envelope polypeptide. Assays to measure envelope activity include, for example, envelope binding assays to CD4, cell fusion assays, and virus entry assays. Such assays are discussed in further detail elsewhere herein. It is recognized that the various methods can be employed to generate the chimeric polypeptide having the heterologous epitope including amino acid substitutions, deletions, truncations, and insertions. Methods for such manipulations are generally known in the art.

As discussed above, the envelope polypeptide comprising the heterologous epitope may be from any lentivirus that is not HIV-1. Such envelope polypeptides include, but are not limited to, an HIV-2 envelope polypeptide, a functional variant of the HIV-2 envelope polypeptide, a SIV envelope polypeptide, or a functional variant of the SIV envelope polypeptide. Other non-HIV-1 envelope polypeptides are discussed elsewhere herein. Cells and viruses comprising the chimeric polypeptide are encompassed by the invention. In one embodiment, the cell comprising the chimeric polynucleotide or polypeptide comprises a packaging cell line that can be used to generate a viral particle having the chimeric polynucleotide or polypeptide of the invention. Such packaging cell lines are known in the art.

Compositions of the invention further include chimeric polynucleotides. Such chimeric polynucleotides comprises a envelope nucleotide sequence or a variant thereof that is not from HIV-1, wherein the nucleotide sequence further comprises a heterologous epitope encoding an epitope recognized by an HIV-1 binding antibody. In specific embodiments, the heterologous epitope recognized by the HIV-binding antibody is a neutralizing HIV-1 epitope, a CD4-induced epitope, or a neutralizing CD4-induced epitope. Cells and viruses comprising the chimeric polypeptide are further provided.

The nucleotide sequence encoding the heterologous epitope or the domain it is contained in can be of any length including about 15 to about 30 nucleotides, about 31 to about 60 nucleotides, about 61 to about 90 nucleotides, about 91 to about 120 nucleotides, about 121 to about 150 nucleotides, about 151 to about 180 nucleotides, about 181 to about 210 nucleotides, about 210 to about 240 nucleotides, about 241 to about 270, about 271 to about 300, about 301 to about 330 nucleotides, or longer. It is recognized that the various methods can be employed to generate the chimeric polynucleotide having the heterologous epitope including amino acid substitutions, deletions, truncations, and insertions. Methods for such manipulations are generally known in the art.

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like. Methods of generating such sequences are discussed elsewhere herein.

Exemplary chimeric polynucleotides and polypeptides of the invention include sequences encoding non-HIV-1 envelope polypeptides, or variants thereof, which have been modified to have an HIV-1 MPER region, a 4E10, a Z13, or a 2F5 epitope or functional variants (immunologically equivalent epitopes) are discussed elsewhere herein. Non-limiting examples of such chimeric polynucleotides and polypeptides include the envelope polypeptide of HIV-2 7312A in which amino acids 675 and 676 (HXB-2c numbering system) are altered from L to I and from A to T, respectively. As shown in FIG. 8, these positions correspond to amino acids 673 and 674 of the envelope polypeptide of HIV-2 7312A. This chimeric polypeptide comprises a heterologous epitope that renders the virus sensitive to neutralization by 4E10 antibodies. In other embodiments, the chimeric envelope polypeptide, or nucleotide sequence encoding it, comprises the HIV-2 ST envelope polypeptide in which amino acids 675 and 676 (HXB-2c numbering system) are altered from L to A and from T to A. This alteration eliminates 4E10 binding. As shown in FIG. 8, these positions correspond to amino acid 664 and 665 of the HIV-2 ST envelope polypeptide (SEQ ID NO:14).

Additional non-limiting examples include the envelope polypeptide of HIV-2 7312A or HIV-2 ST in which the 2F5 epitope, or the immunologically equivalent epitope thereof, is engineered into the polynucleotide. One such chimeric polypeptide, and the chimeric polynucleotide encoding it, includes the polypeptide having site-directed mutations in the HIV-2 7312A envelope polypeptide at positions 660 (K to A), 662 (N to D), 663 (S to K), and 665 (D to A) of SEQ ID NO:2, which together make the HIV-2 sequence identical to that of the 2F5 epitope region of HIV-1 YU2. As shown in FIG. 8, these positions correspond to amino acids 662, 664, 665, and 667, respectively, using the HXB-2c numbering system. Additional chimeric HIV-2 envelope polypeptides having a heterologous MPER domain or a variant or fragment thereof are set forth in FIG. 11.

The chimeric polynucleotide of the invention can be provided in expression cassettes for expression in a cell of interest. The cassette can include 5' and 3' regulatory sequences operably linked to the chimeric polynucleotide of the invention. "Operably linked" is intended to mean a functional linkage between two or more elements. For example, an operable linkage between a chimeric polynucleotide of interest and a regulatory sequence (i.e., a promoter) is functional link that allows for expression of the chimeric polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the cell of interest. Such an expression cassette is provided with a plurality of restriction sites and/or recombination sites for insertion of the chimeric polynucleotide to be under the transcriptional regulation of the regulatory regions. The expression cassette may additionally contain selectable marker genes.

The expression cassette will include in the 5'-3' direction of transcription, a transcriptional and translational initiation region (i.e., a promoter), a chimeric polynucleotide of the invention, and a transcriptional and translational termination region (i.e., termination region) functional in the cell type of interest. The regulatory regions (i.e., promoters, transcriptional regulatory regions, and translational termination regions) and/or the chimeric polynucleotide of the invention may be native/analogous to the host cell or to each other. Alternatively, the regulatory regions and/or the chimeric polynucleotide of the invention may be heterologous to the host cell or to each other.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Additional compositions of the invention comprise kits comprising a retrovirus having the envelope polypeptide or a functional variant thereof from a non-HIV-1 primate lentivirus. Additional compositions comprise kits comprising the retrovirus having the envelope polypeptide or a functional variant thereof from the non-HIV-1 primate lentivirus along with sCD4 of a functional variant thereof. Kits of the invention can also comprise the chimeric polypeptides and polynucleotides described herein. Any kit can further be accompanied by instructions for use as discussed elsewhere herein.

The following examples are offered by way of illustration and not by way of limitation.

EXPERIMENTAL

Example 1

Introduction

In the present study, we sought to identify immunogenic, broadly-cross reactive epitopes on the HIV-1 envelope glycoprotein that might serve as targets of the adaptive humoral immune response in naturally-infected humans. We hypothesized that conserved requirements for co-receptor binding among diverse lineages of human or simian immunodeficiency viruses might be reflected in conserved antigenicity at the corresponding envelope surface. As a strategy, we took advantage of the wide evolutionary distance that exists between HIV-1 and HIV-2 lineages to probe for conserved neutralization epitopes. The envelope glycoproteins of HIV-1 and HIV-2 are only about 40% homologous in amino acid sequence (*HIV Sequence Compendium* 2002. Kuiken et al. Eds. Los Alamos National Laboratory, Los Alamos, N. Mex., LA-UR 03-3564). As a consequence, they generally exhibit weak antigenic cross-reactivity, and sera from HIV-1 infected individuals cross-neutralize HIV-2 poorly if at all (Weiss et al. (1988) *Aids* 2:95-100; Bottiger et al. (1990) *J Virol* 64:3492-3499; Thomas et al. (2003) *AIDS* 17:291-300). Nonetheless, HIV-1 and HIV-2 each require chemokine co-receptor binding for cell entry, with primary non-T cell line adapted viruses of both types generally utilizing CCR5 (Deng et al. (1997) *Nature* 388:296-300; Zhang et al. (2000) *J Virol* 74:6893-6910). Binding of CD4 to HIV-1 gp120 induces conformational changes in the outer and inner envelope domains, the bridging sheet, and the positioning of variable loops V1/V2 and V3 (Sattentau et al. (1993) *J Virol* 67:7383-7393; Wu et al. (1996) *Nature* 384:179-183; Trkola et al. (1996) *Nature* 384: 184-187; Salzwedel et al. (2000) *J Virol* 74:326-333; Rizzuto et al. (1998) *Science* 280:1949-1953; Rizzuto (2000) *AIDS Res Hum Retroviruses* 16:741-749). These changes lead to exposure of the envelope co-receptor binding site, comprised of the bridging sheet, adjacent surfaces, and possibly the tip of V3. Antibodies that bind to HIV-1 gp120 preferentially (or only) after CD4 engagement are referred to as CD4-induced (CD4i). Typically, these antibodies bind to surfaces that include or are proximal to the bridging sheet where they compete with co-receptor binding and broadly (but not potently) neutralize different HIV-1 strains (Salzwedel et al (2000) *J Virol* 74:326-333; Rizzuto et al. (1998) *Science* 280:1949-1953; Rizzuto (2000) *AIDS Res Hum Retroviruses* 16:741-749; Xiang et al. (2002) *AIDS Res Hum Retroviruses* 18:1207-1217; Xiang et al. (2003) *Virology* 315:124-134; Huang et al. (2004) *Proc Natl Acad Sci USA* 101:2706-2711). Cross-reactivity between HIV-1 induced CD4i antibodies and HIV-2 has not been reported. Here, we explore the antigenic cross-reactivity and inherent immunogenicity of the co-receptor binding surfaces of HIV-1 and HIV-2 and assess whether HIV-2, in complex with sCD4, might be useful as a specific probe for HIV-1 elicited CD4i neutralizing antibodies in humans infected by HIV-1 or immunized with candidate HIV-1 vaccines.

Materials and Methods

Plasma Specimens. Pre-existing coded plasma samples from 189 HIV-1 infected subjects and 15 uninfected normal control individuals were analyzed. Blood was generally collected in acid citrate dextrose, platelet-free plasma prepared by sequential 10 min centrifugations at 200 g and 1000 g, and 1 ml aliquots stored at −20° C. or −70° C. Prior to use, plasma was thawed, heat-inactivated at 56° C. for 30 min, and clarified by centrifugation at 3000 g for 5 min. Human subjects gave informed consent and protocols received institutional review board approvals.

Cell Entry and Neutralization Assays. Plasma samples and monoclonal antibodies were assayed for Nab activity using a modification of a recently described HIV entry assay (3) that employs the surface adherent HeLa cell-derived JC53BL-13 cell line (NIH AIDS Research and Reference Reagent Program catalogue #8129, TZM-b1), which has been genetically-modified and selected so as to constitutively express CD4, CCR5 and CXCR4. The cells contain integrated luciferase and β-galactosidase (β-gal) genes under tight regulatory control of an HIV-1 LTR. Virus stocks were obtained by transfection of 293T cells and were titered by β-gal expression on JC53BL-13 cells, as described (Wei et al. (2003) *Nature* 422:307-312). $7 \times 10^3$ JC53BL-13 cells were plated in 96-well tissue culture plates (Falcon) and cultured overnight in DMEM supplemented with 10% fetal calf serum (FCS). 3,000 infectious units of virus were combined in a total volume of 60 µl with or without a 2× concentration of sCD4 in DMEM with 6% FCS and 80 ug/ml DEAE-dextran. After 1 hr at 37° C., an equal volume of test or control plasma (10% vol/vol in DMEM plus 6% FCS or five-fold dilutions thereof) or monoclonal antibody was added. This brought the final concentration of DEAE dextran to 40 µg/ml and that of human plasma to 5%. It is important to note that sufficient normal human plasma (NHP) was added to each well so as to maintain a constant final human plasma concentration of 5% in each virus +sCD4+ test plasma mixture. Concentrations of NHP (or test plasma) that exceed 5% commonly result in nonspecific inhibition of virus entry (Wei et al. (2003) *Nature* 422:307-312), and thus samples are not tested for neutralizing activity at dilutions less than 1:20. The concentration of sCD4 was chosen so that the final 1× concentration after the addition of test plasma corresponds to the $IC_{50}$ of sCD4 specific for each virus. The virus +sCD4+ test plasma (or monoclonal antibody) mixture was incubated for 1 hr at 37° C. Media was removed entirely from the adherent JC53BL-13 monolayer just before the addition of the virus +sCD4+ test plasma (or monoclonal antibody) to it. Cells were incubated at 37° C. for 2 days and then analyzed for luciferase expression, as described (Wei et al. (2003) *Nature* 422:307-312). Controls included cells exposed to no virus and to virus pretreated with NHP or control monoclonal antibodies only. Relative infectivity was calculated by dividing the number of luciferase units at each dilution of test plasma or monoclonal antibodies by values in wells containing NHP but no test plasma or monoclonal antibodies. Neutralization was assessed by 50% inhibitory concentration ($IC_{50}$) determined by linear regression using a least-squares method. All samples were tested in duplicate and all experiments repeated at least three times to ensure reproducibility.

A Cf2Th-synCCR5 cell assay was used to test viruses for CD4-independent cell fusion and entry. Envelope glycoproteins from plasma derived virion RNA/cDNA were expressed in 293T cells and used to pseudotype an env-defective HIV-1 reporter virus (pNLENG1-ES-IRES) containing an enhanced green fluorescent protein (GFP) gene (Levy et al. (2004) *Proc Natl Acad Sci USA* 101:4204-4209). Infectious titers of pseudotyped virus were determined first in JC53BL-53 cells so that virus inoculae could be standardized. Cf2Th-synCCR5 cells (Mirzabekov et al. (1999) *J Biol Chem* 274:28745-28750), which express human CCR5 but not CD4, were plated in 24-well tissue culture plates at a density of $4 \times 10^4$ cells/well and cultured overnight in standard medium (90% DMEM, 10% FBS, 0.5 mg/ml G418, 3.0 ug/ml puromycin, 100 units/ml penicillin, and 100 ug/ml streptomycin) at 37° C. and 5% $CO_2$. Virus, with or without pre-incubation with sCD4, and with or without pre-incubation with monoclonal antibodies or test plasma, was then added in a total volume of 0.25 ml of standard culture medium and incubated for 5 hours at 37° C. If neutralization assays were performed with human plasma, attention was again given to ensure that 5% vol/vol total concentration of plasma was maintained in all wells, as described above in the JC53BL-13 assay. An additional 0.25 ml of medium was then added and the cultures were maintained for 48 hours at 37° C. Thereafter, cells were washed in PBS and visualized directly for GFP expression or detached from the plates by trypsin-EDTA, collected in a 2 ml eppendorf tube, and washed once with PBS before resuspension in 0.3 ml PBS. GFP positive cells were then determined by FACS analysis (Mirzabekov et al. (1999) *J Biol Chem* 274:28745-28750). To test for CCR5-dependent, CD4-independent envelope-mediated fusion, the assay was modified by omitting the env-defective HIV-1 reporter virus (pNLENG1-ES-IRES) and quantifying syncytium formation resulting from co-culture of env-expressing 293T cells and Cf2Th-synCCR5 cells.

Virus stocks. For neutralization experiments in JC53BL-13 cells, HIV-2 proviral clones pJK7312A (GENBANK #L36874) (36-38), pJK7312A/V434M, pJK7312A/H419R, and pJK7312A/Q422L, each cloned in pBlueScript II SK at NotI/EcoRI sites, and pJSP4-27(ST/SXB1) (Deng et al. (1997) *Nature* 388:296-300; Kumar et al. (1990) *J Virol* 64:890-901), were used to transfect 293T cells. HIV-2 UC-1 env (Deng et al. (1997) *Nature* 388:296-300; Barnett et al. (1993) *J Virol* 67:1006-1014) and HIV-1133M env, cloned in pSM and pCR3.1, respectively, were co-transfected with pSG3deltaEnv or pJK7312AdeltaEnv to create infectious pseudovirions, as described (Wei et al. (2003) *Nature* 422: 307-312). For cell entry experiments using Cf2Th-synCCR5 cells (35), HIV-1 env genes cloned in pcDNA3.1 were co-transfected with an HIV-1 reporter virus (pNLENG1-ES-IRES) that contains an enhanced green fluorescence gene (Mirzabekov et al. (1999) *J Biol Chem* 274:28745-28750) using the FuGENE 6 transfection kit (Roche Diagnostics). For antibody binding studies, HIV and SIV envelope glycoproteins were obtained from 293T cells transfected with HIV-$2_{7312A}$; MT4 cells infected by HIV-$2_{MVP15132}$ (Beyl et al. (1987) *Munch Med Wochenschr* 129:895-896; Gao et al. (1993) *AIDS Res. Hum Retroviruses* 9:703-704), HIV-2CBL20 (Schulz et al. (1990) *J Virol* 64:5177-5182), or SIVmac239; and 293T cells infected with recombinant vaccinia viruses expressing HIV-1 JR-FL, HIV-1 Ba-L, or SIVmne gp160 genes.

Binding and Competition Assays. Biotinylated monoclonal antibodies were tested for binding to HIV-2, SIV or HIV-1 gp120 envelope glycoproteins captured in wells of microtiter plates coated with Mab 2.6C or EH21, as previously described (Xiang et al. (2002) *AIDS Res Hum Retroviruses* 18:1207-1217; Xiang et al. (2003) *Virology* 315:124-134). Prior to the addition of biotin-labeled antibodies, gp120 was pre-incubated with sCD4 (R&D Systems, catalogue #514D; 1-10 ug/ml) or a mock preparation. Binding was quantified by the reaction of peroxidase conjugated streptavidin and subsequent color development with substrate TMB-$H_2O_2$. Competition assays were performed by preincubating plasma samples with immobilized gp120-sCD4 complexes and then determining binding of biotin-labeled Mabs at subsaturating concentrations, as described (Xiang et al. (2002) *AIDS Res Hum Retroviruses* 18:1207-1217; Xiang et al. (2003) *Virology* 315:124-134).

Monoclonal antibodies. The prototypic CD4i monoclonal antibodies (Mabs) 17b and 48d, and several more recent CD4i Mabs, 23e, 21c, 4.11 g, 412d, E51 and CM51, have been described (Xiang et al. (2003) *Virology* 315:124-134; Huang et al. (2004) *Proc Natl Acad Sci USA* 101:2706-2711; Thali et al. (1993) *J Virol* 67:3978-3988; Choe et al. (2003) *Cell* 114:161-170; *HIV Immunology and HIV/SIV Vaccine Databases* 2003. Korber et al. Eds. Los Alamos National Laboratory, N. Mex. LA-UR 04-8162). Additional CD4i Mabs used in this study were isolated from HIV-1 infected subjects started on HAART during acute infection. These include 19e, ED47, ED49, ED10, ED11, 31H, 58H and 28d. All of the CD4i Mabs bind to the HIV-1 gp120 glycoprotein co-receptor binding surface that is created (or exposed) following sCD4 binding or deletion or repositioning of V1/V2 variable loop sequences. But three of the Mabs, 19e, ED47 and ED49, are unusual in that they bind poorly, or not at all, to V1/V2 deleted HIV-1 gp120. Hence, their binding is CD4-dependent. Further characteristics of these Mabs will be presented in a separate publication. The other Mabs specific for the HIV-1 CD4 binding site, variable loops, surface glycans, and other gp120 and gp41 epitopes have been described (*HIV Immunology and HIV/SIV Vaccine Databases* 2003. Korber et al. Eds. Los Alamos National Laboratory, N. Mex. LA-UR 04-8162). Human Mabs 1.7 and 2.6C have specificity for HIV-2 gp120 and were isolated from an HIV-2 infected West African patient, as previously described (Cole et al. (2001) *Virology* 290:59-73; Robinson et al. (1998) *AIDS Res Hum Retroviruses* 14:1253-1262). The anti-CD4 Mab from clone RPA-T4 was obtained from BD Biosciences (catalogue # 555344).

Molecular Cloning, Sequencing, and Mutagenesis. Full length gp160 envelope genes were amplified by nested PCR from plasma HIV-1 RNA. Virion-associated plasma RNA was prepared using the QIAmp Viral RNA Mini Kit (Qiagen) as previously described (Wei et al. (2003) *Nature* 422:307-312; Wei et al. (1995) *Nature* 373:117-122). From each timepoint, replicate plasma virus RNA preparations (4000-8000 RNA molecules per reaction) were subjected to cDNA synthesis using SuperScript II (Invitrogen). Replicate viral cDNA samples (1, 10, 100, or 1000 molecules each) were then subjected to nested PCR amplification as described, using the following primers: Outer sense primer (5'-TAGAGCCCTGGAAGCATCCAGGAAG-3', nt 5852-5876) (SEQ ID NO:17), outer anti-sense primer (5'-TTGCTACT-TGTGATTGCTCCATGT-3', nt 8912-8935) (SEQ ID NO: 18), inner sense primer (5'-GATCAAGCTTTAGGCATCTC-CTATGGCAGG AAGAAG-3', nt 5957-5982) (SEQ ID NO: 19), and inner anti-sense primer (5'-AGCTGGATC-CGTCTCGA GATACTGCTCCCACCC-3', nt 8881-8903) (SEQ ID NO: 20). Inner primers contain additional 5' sequences and restriction sites to facilitate cloning. The PCR products of the full-length env genes were cloned into pcDNA3.1 (Invitrogen) for expression. All clones, including those modified by site-directed mutagenesis, were sequenced using an ABI 3100 Genetic Analyzer and dideoxy methodology. Sequences have been deposited in GENBANK (accession numbers AY223761-90; AY223720-54; additional entries pending). To ensure that molecular clones of HIV-1 envelope amplified from plasma viral RNA were representative of plasma virus, replicate PCR reactions were performed on primary samples at varying endpoint titrations of viral cDNA and on separate days. Site-directed mutagenesis was done using the Quik-Change™ site-directed mutagenesis kit (Stratagene Inc.). 125 ng of complementary primers with mutant sequences and 20 ng of template pcDNA3.1-env were used for each PCR amplification. PCR conditions were as follows: 95° C. for 50 sec, 60° C. for 50 sec, and 68° C. for 10 min. After 16 cycles the PCR product was digested with 10 units of DpnI to cleave template DNA at 37° C. for 1 hr. Mutants were identified and confirmed by nucleotide sequencing.

Statistical Analyses. Linear regression, Pearson correlations, Fisher's exact test, and Wilcoxon rank sum test were performed on primary and log transformed data sets. Calculations were performed in SAS.

Figures 1, 6:
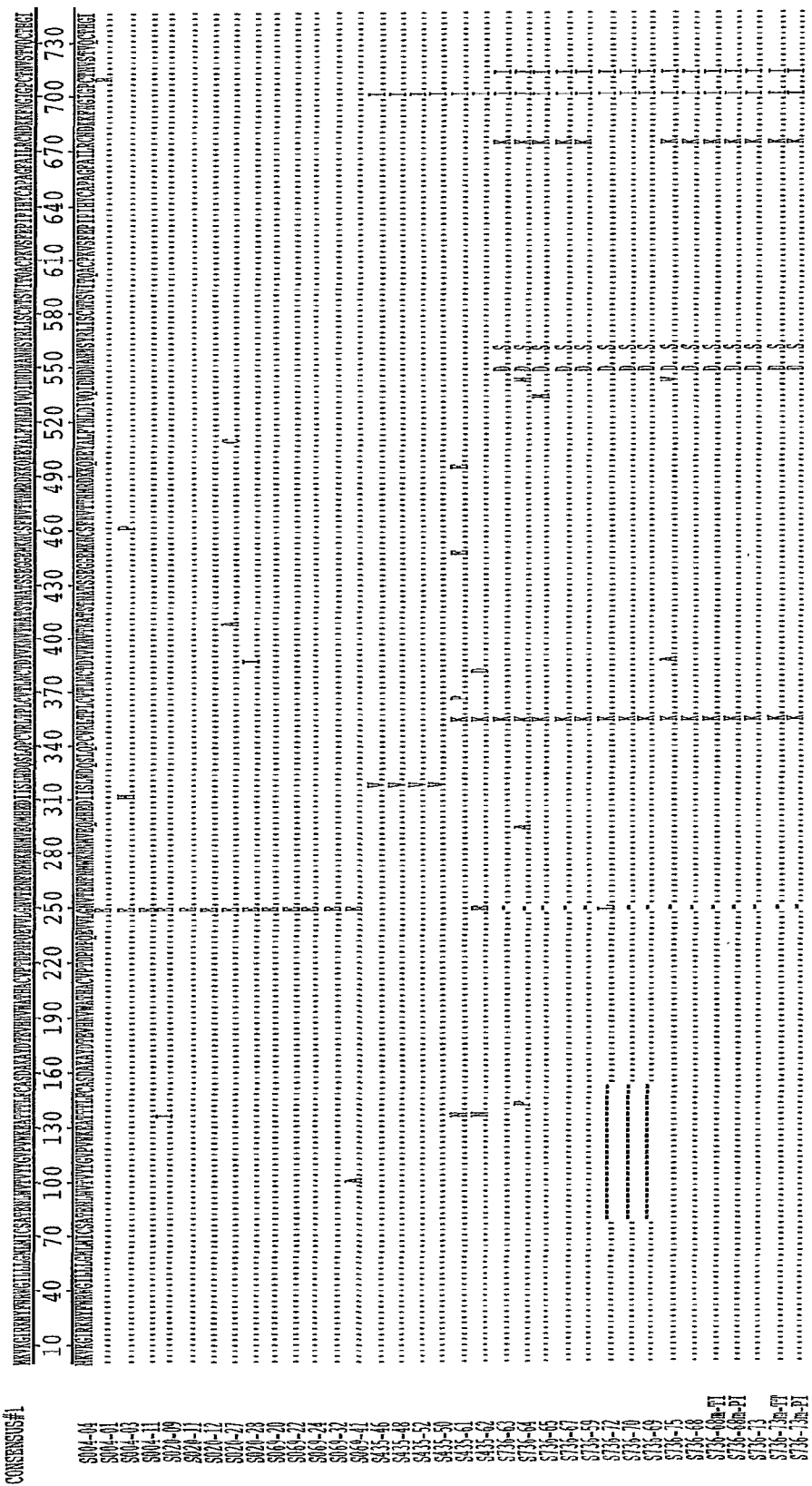
FIG. 6 shows the complete sequences for thirty-one gp160 envelope clones of plasma-virus from subject SUMA0874 with V3 region indicated. Clones are identified according to the day following onset of symptoms of the acute retroviral syndrome the plasma sample was obtained (e.g., S004-11 refers to clone number 04 from a plasma sample taken 11 days following symptom onset, a point when the patient was viral RNA positive and viral antibody negative by ELISA and immunoblot). A subset of the clones depicted was analyzed previously in a study of neutralizing antibody escape (Wei et al. (2003) *Nature* 422:307-312). Four additional gp160 sequences depicted correspond to wild-type clones S736-68 and S736-73 that were modified by site-directed mutagenesis to contain substitutions at the 308 or 309 positions. These are designated S736-68 m/TI, S736-68m/PI, S736-73m/TT, and S736-73m/PI. The critical amino acid substitution at position 309 (isoleucine to threonine) in clones S736-68 and S736-75 responsible for spontaneous co-receptor exposure is highlighted in yellow as is the site-directed mutation made in the wild-type clone S736-73 (S736-73m/TT).
Figures 2, 6:
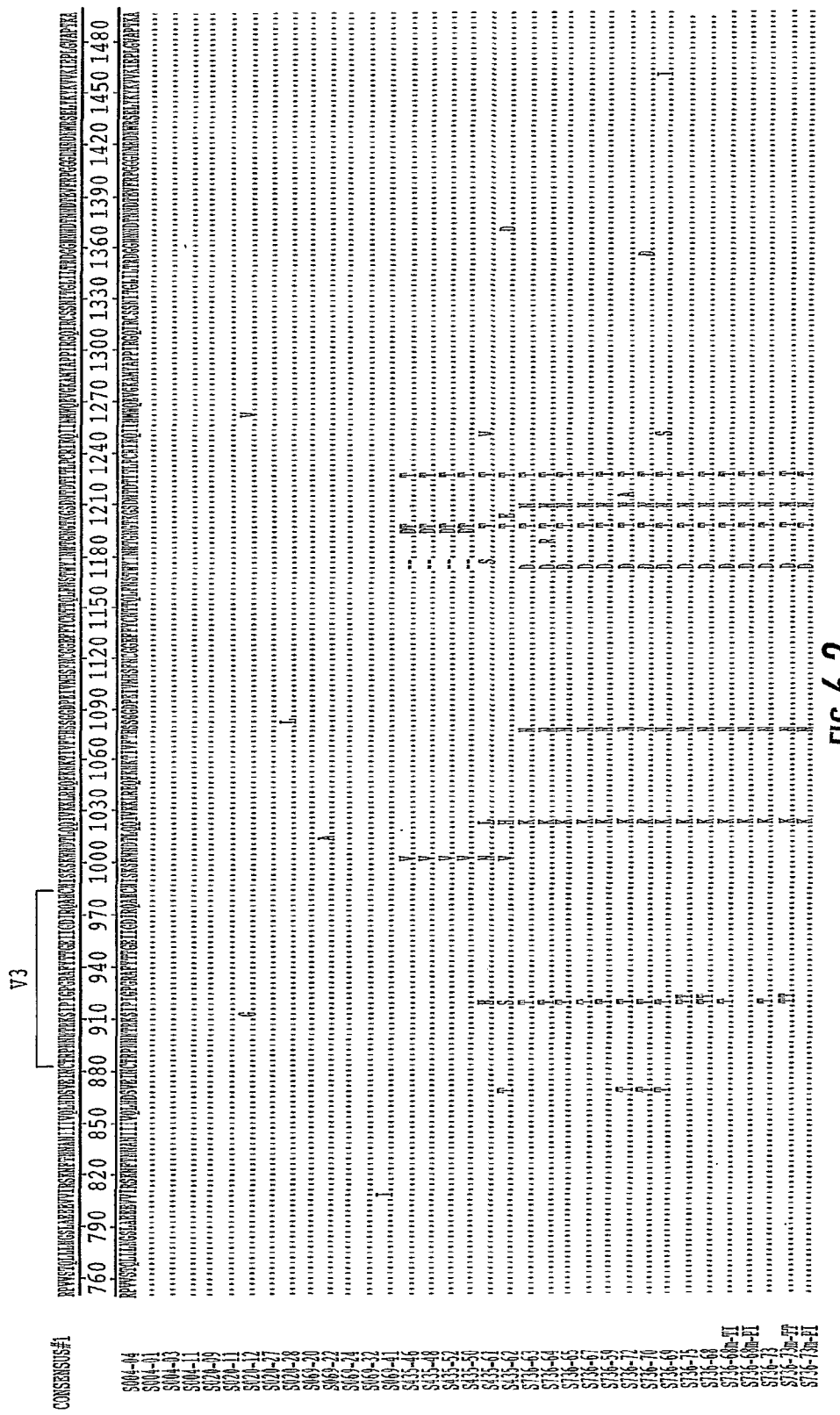

Supplementary Material. FIG. 6 shows the complete amino acid sequences for thirty-one gp160 envelope clones derived from plasma virus from subject SUMA0874 with V3 region indicated. Four additional gp160 sequences corresponding to site-directed mutants of wild-type clones S736-68 and S736-73 containing substitutions at positions 308 or 309 (HXB2 numbering system) are designated S736-68m/TI, S736-68m/PI, S736-73m/TT, and S736-73m/PI.

Results

Plasma from HIV-1 Infected Patients Neutralizes CD4-induced HIV-2. Table 1 shows the extent and kinetics of the Nab response to autologous HIV-1 virus in a patient (133M) following subtype C HIV-1 infection.

TABLE 1

Neutralization of HIV-1 and HIV-2 by sequential plasma specimens from an HIV-1 seroconverter.

| Patient 133M | HIV-1 133M Virus[a] | HIV-2 7312A Virus | HIV-2 7312A Virus + sCD4 |
|---|---|---|---|
| Month 2 | 22[b] | 0 | 154 |
| Month 6 | 250 | 0 | 63 |
| Month 8 | 333 | 0 | 105 |
| Month 11 | 2,500 | 0 | 833 |
| Month 14 | 1,667 | 0 | 2,000 |
| Month 18 | 1,429 | 0 | 5,556 |
| Month 20 | 1,136 | 0 | 7,143 |
| Month 23 | 1,053 | 0 | 11,111 |
| Month 26 | 556 | 0 | 12,500 |

[a]The HIV-1 gp160 env gene from patient 133M was PCR amplified and cloned from uncultured month 2 peripheral blood mononuclear cells and used to prepare pseudotyped virus.
[b]Reciprocal $IC_{50}$ titer of neutralizing antibodies as determined in JC53BL-13 cells (1).

[a]The HIV-1 gp160 evn gene from patient 133 M was amplified and cloned from uncultured month 2 peripheral blood mononuclear cells and used to prepare pseudotyped virus.
[2]Reciprocal $IC_{50}$ titer of neutralizing antibodies as determined in JC53BL-13 cells (1).

Nab titers against the earliest detectable virus reached 1:2, 500 (50% inhibitory concentration, $IC_{50}$) by 11 months of infection and then subsided. Such a response is typical of patients with newly acquired HIV-1 infection, and it is generally followed rapidly by virus mutation and escape from neutralization (Wei et al. (2003) *Nature* 422:307-312; Richmanetal. (2003) *Proc Natl Acad Sci USA* 100:4144-4149). To look for more broadly reactive Nabs in this subject, we applied these same plasma specimens to the HIV-2 strain 7312A, a primary CD4-dependent R5 virus (Deng et al. (1997) *Nature* 388:296-300; Zhang et al. (2000) *J Virol* 74:6893-6910; Deng et al. (1997) *Nature* 388:296-300; Zhang et al. (2000) *J Virol* 74:6893-6910). As expected, plasma from this HIV-1 infected patient (133M) exhibited no detectable neutralizing activity against HIV-$2_{7312A}$, a finding consistent with prior studies showing little neutralization cross-reactivity between these highly divergent viral lineages (Weiss et al (1988) *Aids* 2:95-100; Bottiger et al (1990) *J Virol* 64:3492-3499). However, when HIV-$2_{7312A}$ was pretreated for 1 hour with 9 nM sCD4 (equal to the $IC_{50}$ for this virus), the virus became remarkably susceptible to neutralization by 133M plasma, with titers of Nab reaching 1:12,500 by 26 months following infection (Table 1). Similar results were obtained in six additional subjects with primary subtype C HIV-1 infection whose Nab titers to sCD4-pretreated HIV-$2_{7312A}$ ranged from 1:53 to 1:3,361 and which peaked between 8 and 24 months following acute infection. To determine if the CD4-dependent Nab activity that we observed in plasma from subtype C patients was limited to this virus lade, we studied additional patients chronically infected with HIV-1 subtypes A, B, C or D. FIG. 1a depicts the neutralization profile of plasma from four such patients against HIV-$2_{7312A}$ in the absence or presence of sCD4. In each case, there was a dramatic sCD4-dependent shift of 100 to 10,000-fold in the susceptibility of HIV-2 to neutralization. $IC_{50}$ titers of CD4i Nab titers in these four individuals ranged from 1:750 to 1:20,000. Fifteen uninfected normal donors had no detectable Nabs to HIV-2$_{7312A}$ with or without sCD4.

Figure 1B:
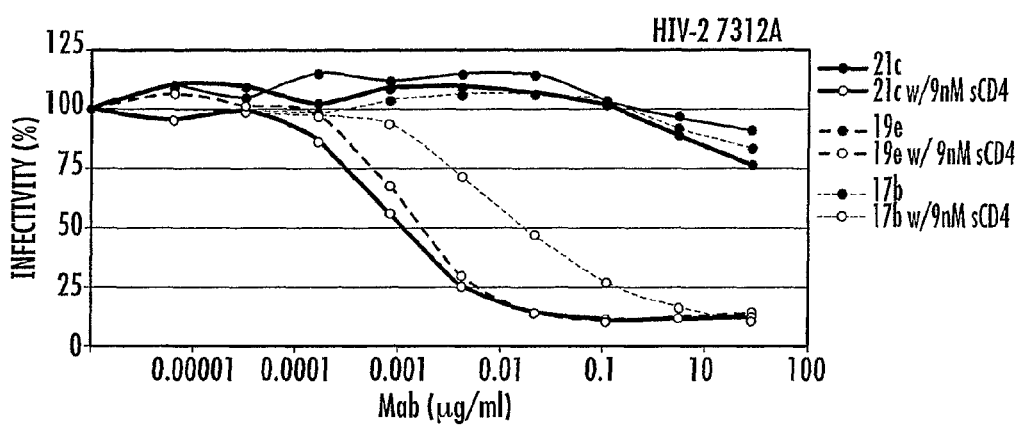
Figure 1C:
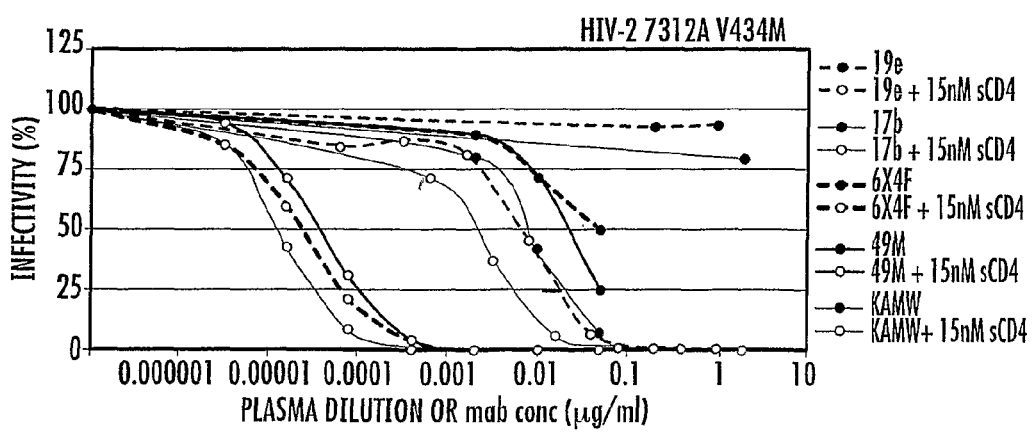

HIV-1 CD4i Monoclonal Antibodies Neutralize CD4-induced HIV-2. If the broadly cross-reactive neutralizing antibody activity that we observed in HIV-1 infected patient plasma is due to classical CD4i antibodies, then prototypic CD41 monoclonal antibodies derived from HIV-1 infected patients, which have been extensively characterized against HIV-1 envelope glycoproteins (Salzwedel et al. (2000) *J Virol* 74:326-333; Rizzuto et al. (1998) *Science* 280:1949-1953; Rizzuto (2000) *AIDS Res Hum Retroviruses* 16:741-749; Xiang et al. (2002) *AIDS Res Hum Retroviruses* 18:1207-1217; Xiang et al. (2003) *Virology* 315:124-134; Huang et al. (2004) *Proc Natl Acad Sci USA* 101:2706-2711), might be expected to cross-neutralize HIV-2 in a CD4-dependent fashion. FIG. 1b demonstrates this to be the case. Without sCD4, the CD4i monoclonals 17b, 21c and 19e failed to neutralize HIV-2$_{7312A}$. In the presence of sCD4, a dramatic shift in the neutralization curves was observed with all three antibodies neutralizing HIV-2$_{7312A}$ potently (FIG. 1b). It is notable that for both the CD4i polyclonal (FIG. 1a) and monoclonal (FIG. 1b) antibodies, the extent of neutralization reached only about 90%, and in the case of the clade D plasma KAWM, 80%. This is due in part to a time- and concentration-dependent interaction between sCD4 and the gp120 envelope glycoprotein, since higher sCD4 concentrations and more prolonged preincubation times (30-120 minutes) increased the extent of HIV-2$_{7312A}$ neutralization by both monoclonal and polyclonal CD4i antibodies (data not shown). Steric accessibility or affinity of CD41 antibodies to their cognate epitopes may also influence the extent of virus neutralization since a single mutation (V434M) in the bridging sheet of HIV-2$_{7312A}$, making this amino acid the same as in HIV-1 (see below), resulted in a marked shift of the neutralization curves of 17b and 19e and of three HIV-1 patient plasmas to the left and downward, resulting in 100% neutralization of infectious virus (FIG. 1c).

Multiple Primary HIV-2 Strains are Susceptible to HIV-1 CD4i Antibody Neutralization. Neutralization of HIV-2 by HIV-1 elicited CD4i antibodies is not restricted to HIV-2$_{7312A}$ and derivative strains. HIV-2$_{UC-1}$ and HIV-2$_{ST/SXB1}$, two other well-characterized HIV-2 R5-tropic viruses (Deng et al. (1997) *Nature* 388:296-300; Barnett et al. (1993) *J Virol* 67:1006-1014), also demonstrated striking neutralization susceptibility to HIV-1 elicited CD4i monoclonal antibodies and to HIV-1 infected patient plasma in patterns that were similar (but not identical) to HIV-2$_{7312A}$. Results for HIV-2$_{7312A}$ and HIV-2$_{UC-1}$ are compared in Table 2.

TABLE 2

Neutralization titers of HIV-1 monoclonal antibodies and patient plasma against different HIV-2 viruses.

| Moab | Epitope | 7312A | UC-1 | 7312A V434M | 7312A H419R | 7312A Q422L |
|---|---|---|---|---|---|---|
| E51 | CD4i | —/—$^a$ | —/13.0 | —/4.0 | —/22.0 | —/— |
| 17b | CD4i | —/0.16 | —/9.4 | 8.0/0.002 | 15.0/0.002 | —/— |
| 48d | CD4i | —/— | —/— | —/— | —/— | —/— |
| 31H | CD4i | —/3.71 | —/1.58 | —/0.62 | —/1.42 | —/— |
| 23e | CD4i | —/— | —/— | —/— | —/— | —/— |
| 21c | CD4i | —/0.011 | —/0.005 | —/0.94 | —/0.014 | —/0.03 |
| X5 | CD4i | —/— | —/— | —/2.5 | —/— | —/— |
| 412d | CD4i | —/— | —/— | —/— | —/— | —/— |
| 19e | CD4i | —/0.017 | —/0.009 | —/0.006 | —/0.005 | —/0.01 |
| ED47 | CD4i | —/— | —/— | —/— | —/4.7 | —/— |
| ED49 | CD4i | —/5.4 | —/12.0 | —/2.4 | —/3.3 | —/3.0 |
| b12 | CD4bs | —/— | —/— | n.d. | n.d. | n.d. |
| F105 | CD4bs | —/— | —/— | n.d. | n.d. | n.d. |
| F91 | CD4bs | —/— | —/— | n.d. | n.d. | n.d. |
| 15e | CD4bs | —/— | —/— | n.d. | n.d. | n.d. |
| 2F5 | gp41 | —/— | —/— | n.d. | n.d. | n.d. |
| 447-52D | V3 | —/— | —/— | n.d. | n.d. | n.d. |
| 19b | V3 | —/— | —/— | n.d. | n.d. | n.d. |
| C011 | V3 | —/— | —/— | n.d. | n.d. | n.d. |
| 2580 | V3 | —/— | —/— | n.d. | n.d. | n.d. |
| 2442 | V3 | —/— | —/— | n.d. | n.d. | n.d. |
| 2G12 | Glycan | —/— | —/— | n.d. | n.d. | n.d. |
| A32 | gp120 | —/— | —/— | n.d. | n.d. | n.d. |
| C11 | gp120 | —/— | —/— | n.d. | n.d. | n.d. |
| 2.6C | HIV-2/gp120 | —/— | —/— | n.d. | n.d. | n.d. |
| 1.7A | HIV-2/gp120 | 0.016/0.011 | 0.005/0.007 | 0.017/0.009 | 0.023/0.017 | 0.009/0.009 |

| Patient ID | HIV-1 Subtype | 7312A | UC-1 | 7312A V434M | 7312A H419R | 7312A Q422L |
|---|---|---|---|---|---|---|
| 6X4F | A | —/10,000 | 370/76,923 | 20/41,667 | 4,065/96,937 | n.d. |
| 21X0F | A | —/6,667 | 500/13,699 | 63/17,241 | 222/47,619 | n.d. |
| 37X4F | A | —/3,846 | —/1,333 | 59/68,027 | 435/65,240 | n.d. |
| BAMA0037 | B | 36/4,167 | 83/3,448 | 40/16,667 | 48/4,167 | n.d. |
| SMST1012 | B | 67/7,692 | 370/9,090 | 48/13,514 | 192/4,348 | n.d. |
| KIMA9001 | B | 31/1,136 | 36/1,563 | 37/6,250 | 21/1,612 | n.d. |
| 200M | C | —/2941 | 91/5,000 | 31/4,348 | 77/7,692 | n.d. |

TABLE 2-continued

Neutralization titers of HIV-1 monoclonal antibodies and patient plasma against different HIV-2 viruses.

| 49M  | C | —/17,241  | 385/17,241 | 45/27,027  | 333/65,189 | n.d. |
|------|---|-----------|------------|------------|------------|------|
| 42F  | C | —/5,000   | 263/6,251  | —/52,632   | —/18,181   | n.d. |
| KAWM | D | —/18,868  | 53/18,519  | 143/83,333 | 27/26,316  | n.d. |
| sCD4 |   | 9 nM      | 3 nM       | 15 nM      | 28 nM      | 6 nM |

[a]Values preceding the slash marks denote the $IC_{50}$ in µg/ml for monoclonal antibodies and in reciprocal dilutions for patient plasma specimens, each in the absence of sCD4. Values following the slash marks denote $IC_{50}$ values in the presence of sCD4. sCD4 concentrations were adjusted to correspond to the $IC_{50}$ specific for each virus as indicated in the bottom row. Dashes denote absent neutralization defined as $IC_{50}$ titers greater than 25 µgm/ml for monoclonal antibodies or less than 1:20 for human plasma. Neutralization assays were performed in JC53BL-13 cells (1).
n.d., not done.

Each virus was susceptible to 21c and 19e and to a lesser extent 17b, 31H and ED49. HIV-2$_{UC-1}$ was more susceptible to E51 and 31H, but much less susceptible to 17b, compared with HIV-2$_{7312A}$. Both viruses were completely resistant to neutralization by 13 different HIV-1 elicited non-CD4i human monoclonal antibodies, including those targeting the CD4 binding site (CD4bs), V3 loop, surface glycans, and gp41. HIV-2$_{UC-1}$ was also compared with HIV-2$_{7312A}$ in its susceptibility to neutralization by a subset of ten HIV-1 clade A, B, C and D patient plasmas (Table 2, bottom). CD4-dependent Nab titers against HIV-2$_{UC-1}$ were at least two-fold higher than for HIV-2$_{7312A}$ in two patients (6X4F and 21X0F), three-fold lower in one patient (37X4F), and not substantially different in seven others. For each HIV-1 antibody positive plasma specimen tested, there was a one to three log CD4-dependent shift in the HIV-2$_{UC-1}$ neutralization curve (Table 2, bottom).

Figure 2:
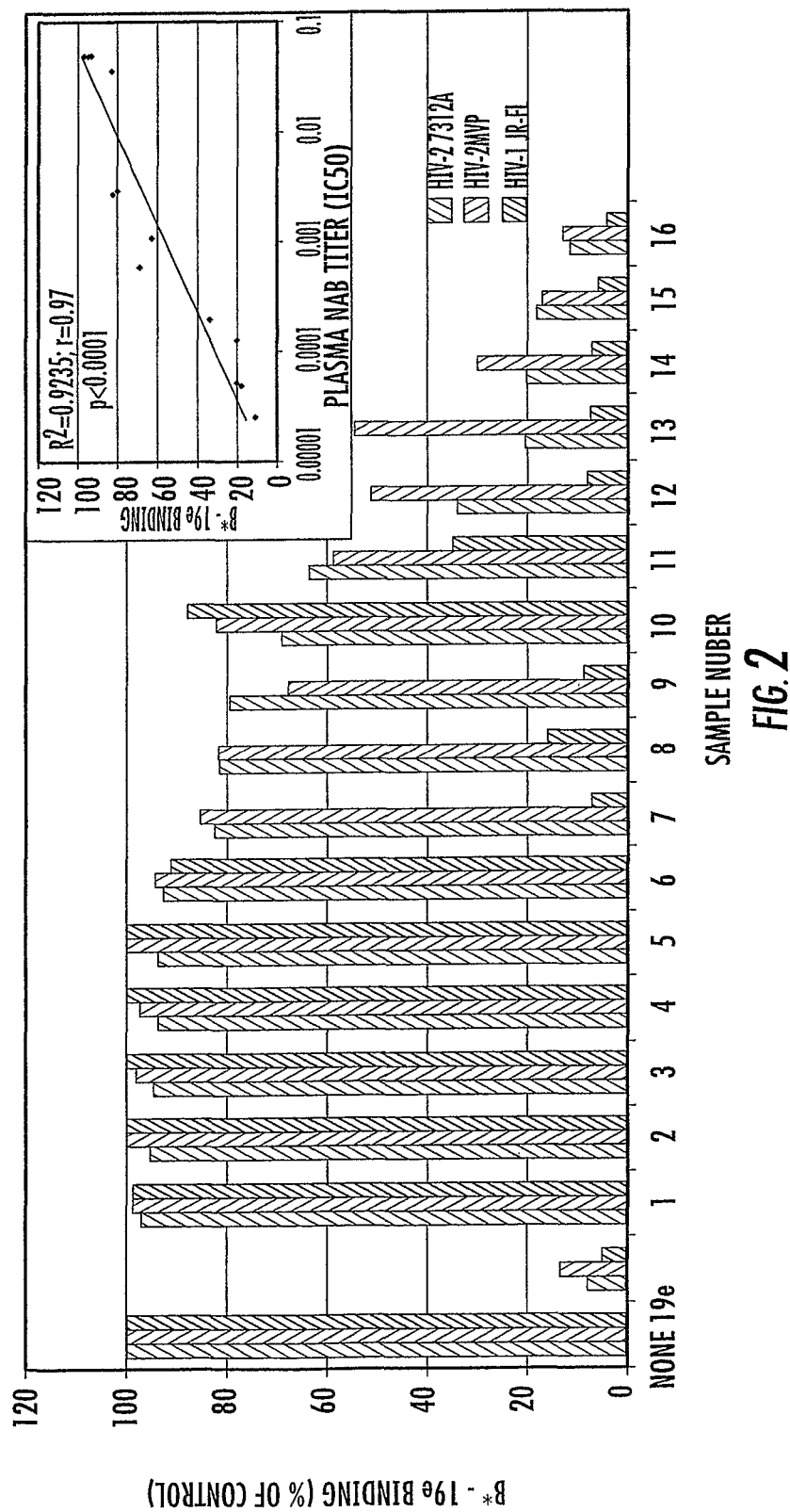
FIG. 2 shows the blocking of biotinylated 19e binding to HIV-1 and HIV-2 gp120-sCD4 complexes by human plasma samples from either normal uninfected donors (samples #1-5) or HIV-1 infected subjects (samples #6-16). Unlabelled 19e effectively competed with biotinylated 19e for binding to all gp120-sCD4 complexes and served as a positive control.

HIV-1 CD4i Antibody Binding to HIV-2 Glycoprotein Correlates With Neutralization. CD4i antibodies in HIV-1 plasma that neutralize HIV-2 infection might also be expected to compete directly with HIV-1 CD4i monoclonal antibodies for binding to HIV-2 gp120-sCD4 complexes. FIG. 2 shows the results of an assay using 16 human plasma samples (11 HIV-1 positive; 5 normal uninfected controls) to compete with biotin-conjugated 19e for binding to HIV-2$_{7312A}$, HIV-2HIV-2$_{MVP15132}$, or HIV-1$_{JR-FL}$ gp120-sCD4 complexes. A mock-treated sample did not inhibit biotin-labeled 19e binding, which was normalized to 100%. Unlabeled 19e competed efficiently with biotin-labeled 19e binding to each of the three HIV glycoproteins. The five normal control specimens (samples #1-5) showed no significant competition for biotinylated 19e binding to any of the three HIV envelope glycoproteins. The 11 HIV-1 positive patient specimens, however, competed variably with 19e for binding to both HIV-1 and HIV-2 glycoproteins. Samples #13-16 showed the strongest competition against 19e for HIV-2$_{7312A}$ binding, and these samples also exhibited the highest neutralization titers against HIV-2$_{7312A}$ (reciprocal mean $IC_{50}$=0.00007±0.00005). Samples #6-9 showed the least competition with 19e for binding HIV-2$_{7312A}$, and these had the lowest Nab titers against this virus ($IC_{50}$=0.023±0.024). Other samples were intermediate in binding and neutralization activity. There was a highly significant correlation between the titers of Nab measured against HIV-2$_{7312A}$ and the efficiency with which these plasma specimens competed with 19e for HIV-2$_{7312A}$ binding ($R^2$=0.94; r=0.97; p<0.0001). With the exception of sample #10, the HIV-1 positive patient plasma specimens competed for 19e binding to the HIV-1$_{JR-FL}$ glycoprotein more efficiently than to either of the two HIV-2 glycoproteins.

Figure 3A:
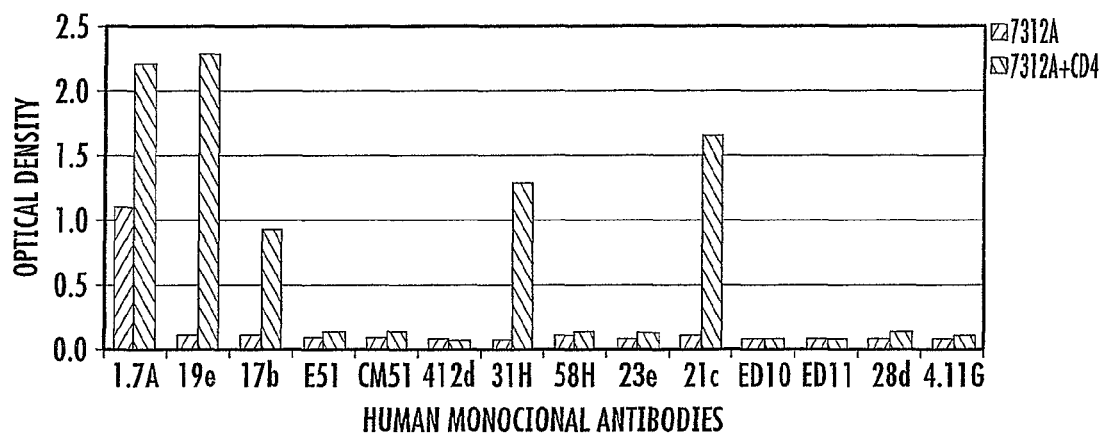
FIG. 3 shows the screening of CD4i monoclonal antibodies for binding to HIV-$2_{7312A}$ (panel a) and to additional HIV and SIV (panel b) gp120-sCD4 complexes. 1.7A is a human HIV-2 gp120 specific monoclonal antibody whereas all other monoclonal antibodies are CD4i antibodies derived from HIV-1 infected humans.
Figure 3B:
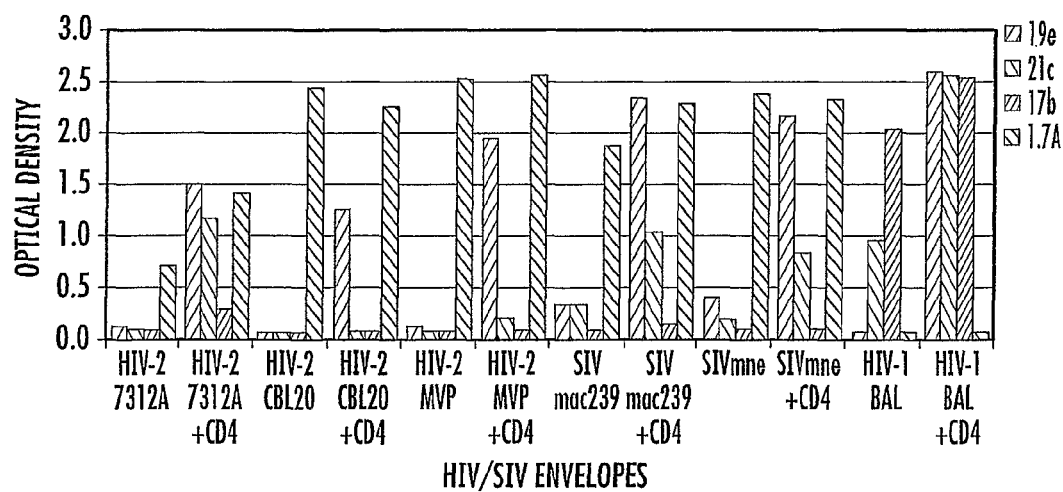
Figure 5A:
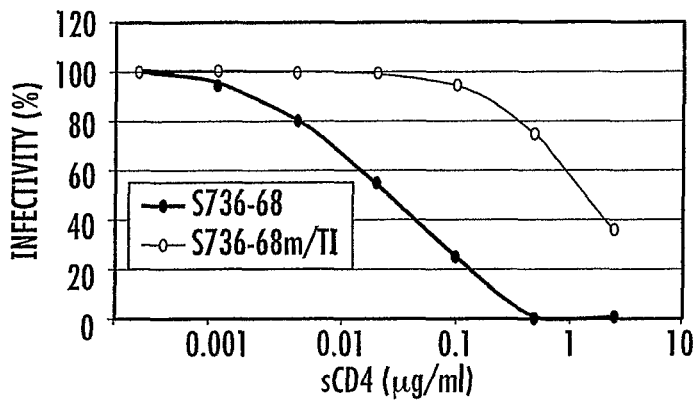
FIG. 5 shows the neutralization of S736-68 and S736-68m/TI infectivity in JC53BL-13 cells (Wei et al. (2003) *Nature* 422:307-312) by sCD4 (panel A), anti-CD4 monoclonal antibody RPA-T4 (panel B), CD4i monoclonal antibody 17b (panel C), and autologous patient plasma from day 278 following acute infection by HIV-1 (panel D).
Figure 5B:
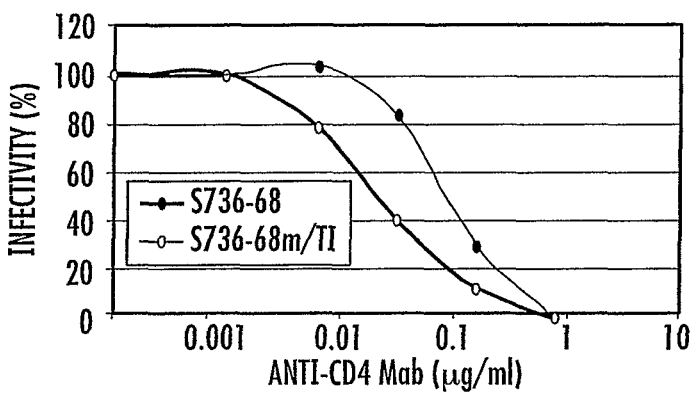
Figure 5C:
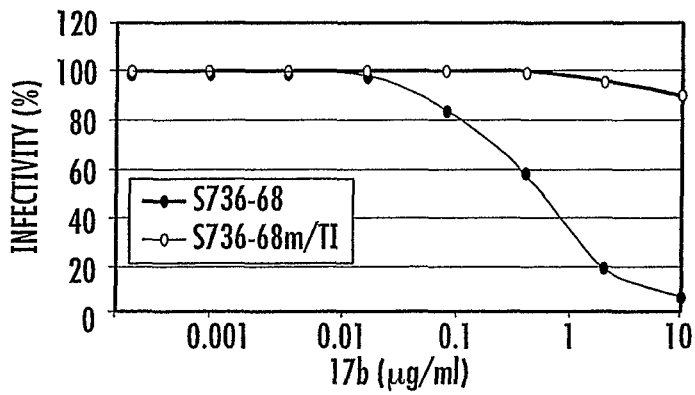
Figure 5D:
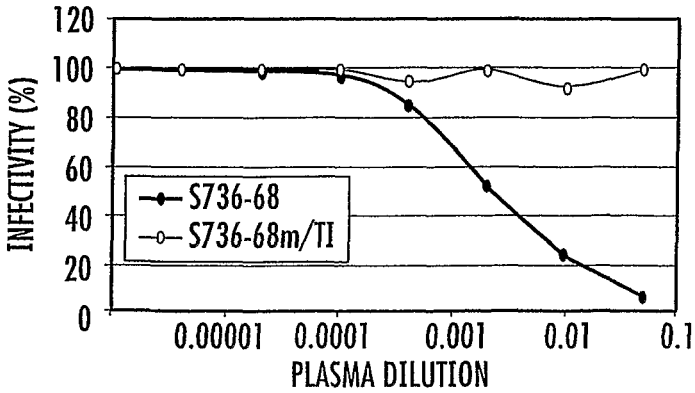

To further examine the correlation between antibody binding and neutralization, we tested a large number of biotin-labeled HIV-1 CD4i antibodies for binding to HIV-2$_{7312A}$ envelope glycoprotein with and without sCD4. FIG. 3a shows that the HIV-1 elicited CD4i antibodies that were found in Table 2 to neutralize HIV-2$_{7312A}$ most efficiently (19e, 17b, 31H, 21c), also bound the HIV-2$_{7312A}$ glycoprotein most efficiently in a CD4-dependent manner, while those antibodies that neutralized poorly, bound poorly. To further evaluate the breadth of HIV-1 CD4i monoclonal antibody binding, we tested three antibodies (19e, 21c, and 17b) for reactivity against additional primate lentiviruses (FIG. 3b). The HIV-1 CD4i monoclonal antibodies bound not only HIV-2$_{7312A}$ env-sCD4 complexes, but also HIV-2$_{CBL20}$, HIV-2$_{MVP15132}$ SIVmac239, SIVmne, and as a control, HIV-1$_{BAL}$. It is again noteworthy that gp120-sCD4 complexes from different HIV-2 and SIV strains were recognized variably by the three HIV-1 CD4i monoclonal antibodies, with 19e exhibiting the strongest reactivity to all viral envelopes, followed by 21c, and then 17b. These findings, together with the neutralization results, indicate that the CD4-induced chemokine receptor binding surfaces of HIV-2 strains 7312A, UC-1, ST/SXB1, CBL20 and MVP15132, as well as SIVmac239 and SIVmne, all share substantial antigenic cross-reactivity with each other and with HIV-1.

Site-directed Mutagenesis of the HIV-2 Bridging Street Alters HIV-1 CD4i Antibody Recognition. HIV-2 neutralization by HIV-1 CD4i monoclonal and polyclonal antibodies is best explained by antibodies binding to the conserved chemokine co-receptor binding surface, including the bridging sheet. To evaluate this hypothesis directly, we performed site-directed mutagenesis on the HIV-2 bridging sheet region (Reeves et al. (2002) *J Gen Virol* 83:1253-1265). The primary amino acid sequence of the bridging sheet of HIV-1 and the corresponding sequence of HIV-2 is conserved but not identical (FIG. 4). Substitutions were made at three positions in the HIV-2$_{7312A}$ sequence at or near the binding footprints of monoclonals 17b, 21c and 19e in the corresponding HIV-1 sequence (Kwong et al. (1998) *Nature* 393:648-659; Wyatt et al. (1998) *Nature* 393:705-711; Xiang et al (2002) *AIDS Res Hum Retroviruses* 18:1207-1217). The effects of these mutations on the susceptibility of the respective viruses to neutralization by HIV-1 monoclonal and polyclonal antibodies were substantial (FIG. 1c and Table 2). Mutations V434M and H419R (HXB2 numbering system; see FIG. 4) made the HIV-2 sequence at these positions the same as HIV-1, and thus would be expected to enhance HIV-1 CD4i-antibody binding. The V434M substitution led to an 80-fold enhancement of 17b neutralization, at least 10-fold enhancement of X5 neutralization, 6-fold increase in E51 and 31H neutralization, and 2-3-fold enhancement of ED49 and 19e neutralization. Neutralization enhancement was not global, however, since there was a concomitant 85-fold decrease in 21c susceptibility and no change in susceptibility to the HIV-2 monoclonal 1.7A, which binds a conserved epitope distant from the bridging sheet (Table 2). Similarly, the H419R mutation led to a 2 to 80-fold enhancement in neutralization by 17b, 31H, 19e, ED47, and ED49, but little or no change in susceptibility to E51, 21c or 1.7A. In addition to mutations expected to enhance HIV-1 CD4i antibody binding, we also tested a Q422L mutant, which had been shown in HIV-1 to reduce CD4I-antibody binding (e.g., 17b), while allowing the envelope to otherwise retain its normal receptor binding and entry functions (Xiang et al. (2002) *AIDS Res Hum Retroviruses* 18:1207-1217). The Q422L mutation in 7312A resulted in complete loss of 17b neutralization (>150-fold change), complete loss in 31H neutralization (>7-fold change), and a 3-fold decrease in 21c neutralization, but had little effect on 19e, ED49, or 1.7A mediated neutralization. Enhanced susceptibility of the V434M and H419R mutants to neutralization was also observed with most of the HIV-1 patient plasmas tested (Table 2).

Prevalence and Titers of CD4i Neutralizing Antibodies in Patients Infected by Diverse HIV-1 Subtypes. Plasma samples from 189 individuals infected by HIV-1 clades A, B, C, D, F, G or H, or by CRF01, CRF02 or CRF11, were tested for CD4i Nabs against HIV-2. In preliminary studies, we tested a subset of 69 of these specimens for reactivity against the wildtype HIV-2 strain 7312A and its derivative 7312A/V434M. This pilot study showed that the frequency of detection of HIV-2 cross-reactive CD4i Nabs was modestly higher for the V434M virus (94%) compared with 7312A (87%). Based on the enhanced sensitivity of HIV-2$_{7312A/V434M}$, we used this virus to test all 189 patient plasma specimens for CD4i Nabs (Table 3).

TABLE 3

Prevalence and Titers of CD4i Neutralizing Antibodies Against HIV-2$_{7312A/V434M}$ in Plasma of HIV-1 Infected Subjects

| HIV-1 Plasma | n | Positive (%) | CD4i Nab Titers[a] | | |
|---|---|---|---|---|---|
| | | | Mean | S.D. | Median |
| Clade A | 39 | 35 (90%) | 0.0029 | 0.0052 | 0.0007 |
| Clade B | 25 | 24 (96%) | 0.0047 | 0.0105 | 0.0003 |
| Clade C | 23 | 22 (96%) | 0.0051 | 0.0118 | 0.0004 |
| Clade D | 7 | 7 (100%) | 0.00007 | 0.00006 | 0.00007 |
| Clade F | 6 | 5 (83%) | 0.0008 | 0.0005 | 0.001 |
| Clade G | 5 | 3 (60%) | 0.0061 | 0.0092 | 0.0015 |
| Clade H | 2 | 2 (100%) | 0.002 | 0.0028 | 0.002 |
| CRF01 | 1 | 1 (100%) | 0.0003 | — | 0.0003 |
| CRF02 | 77 | 72 (94%) | 0.0053 | 0.0106 | 0.0008 |
| CRF11 | 4 | 3 (75%) | 0.00005 | 0.00002 | 0.00004 |
| Total | 189 | 174 (92%) | 0.004 | 0.0093 | 0.0004 |

[a]Reciprocal IC$_{50}$ titers of CD4i neutralizing antibodies against HIV-2$_{7312A/V434M}$ pretreated with 15 nM sCD4.

CD4i Nabs were detected in 174 (92%) of patients, with median IC$_{50}$ titers of 0.0004 (1:2,500) and mean titers of 0.004 (1:250). Titers of CD4i Nab in plasma from clade D and CRF11 patients, considered separately or as a group, were significantly greater than for patients in the remaining groups (p<0.0001). We considered the possibility that, despite the overall similarity in neutralization patterns observed for the HIV-2 strains depicted in Table 2, divergent HIV-2 strains might detect CD4i Nabs in some of the patient's plasmas that tested negative against HIV-2$_{7312A/V434M}$. Thus, we retested the 15 negative samples, first by western immunoblot to confirm HIV-1 positivity, and then by neutralization assay against two different HIV-2 strains: UC-1, ST/SXB1, and 7312A. All 15 samples were western immunoblot positive against HIV-1 proteins. Four samples were found to have CD4i Nabs against one or more of these viruses in titers ranging from 1:25 to 1:750. Thus, overall, out of 189 HIV-1 infected patients tested, 178 (94%) had detectable neutralizing CD4i antibodies against HIV-2.

Role of CD4i Antibodies in Natural HIV-1 Infection. Previous studies have shown that HIV-1 CD4i antibodies are largely excluded by steric hindrance from the virus:cell interface following CD4 engagement, and as a consequence, CD4Ii antibodies generally neutralize HIV-1 inefficiently (Labrijn et al. (2003) *J Virol* 77:10557-10565; Salzwedel et al. (2000) *J Virol* 74:326-333). However, this steric restriction could be overcome experimentally by using CD4i antibody fragments (Fab or sFv) or by disassociating (spatially or temporally) envelope-CD4 engagement from envelope-coreceptor engagement (Labrijn et al. (2003) *J Virol* 77:10557-10565; Salzwedel et al. (2000) *J Virol* 74:326-333). Given these constraints on CD4i antibody-mediated neutralization, we sought to examine what role CD4i antibodies might play in vivo. Sodroski and colleagues (Kolchinsky et al (2001) *J Virol* 75:2041-2050) first postulated that CD4i antibodies might constrain virus to CD4 dependence by selecting against envelope mutations that lead to spontaneous exposure of the viral co-receptor binding surface (Kolchinsky et al (1999) *J Virol* 73:8120-8126; Hoffman et al. (1999) *Proc Natl Acad Sci USA* 96:6359-6364). Our results support this hypothesis by showing in naturally-infected humans that CD4i antibodies are prevalent, high-titer, and so broadly cross-reactive that they neutralize even HIV-2. However, to test more directly if CD4i antibodies might be active in constraining HIV-1 to CD4 dependence in vivo, we examined sequential uncultured plasma specimens from four HIV-1 infected patients (133M, WEAU0575, SUMA0874, BORI0637) for evidence of viruses that contain mutations in envelope that result in greater spontaneous exposure of the receptor binding surfaces. Seventy-four full-length, functional gp160 envelope clones were derived by polymerase chain reaction (PCR) amplification of plasma virion RNA and used to pseudotype env-deficient HIV-1 virus for entry in JC53BL-13 cells. Two clones from patient SUMA0874 (S736-68 and S736-75) were found to be uniquely sensitive to neutralization by sCD4 (IC$_{50}$<0.05 ug/ml), indicating that they might exhibit greater spontaneous exposure of receptor binding surfaces than is generally observed in primary HIV-1 strains (Pugach et al. (2004) *Virology* 321:8-22). These same two clones were also distinguished from all others that we examined by an isoleucine (I) to threonine (T) substitution at position 309 (HXB2 numbering system) immediately 5' of the GPGR crown of the V3 loop (FIG. 6), a position reported by Quinnan and colleagues (Zhang et al. (2002) *J Virol* 76:644-655) to confer CD4-independent infectivity and enhanced susceptibility to neutralization in an unrelated primary HIV-1 strain. We therefore first tested clones S736-68 and S736-75, along with other SUMA clones lacking the I309T mutation (including S736-68 in/TI), for CD4-independent fusion and infectivity in Cf2Th-synCCR5 cells, a canine thymocyte cell line that expresses human CCR5 but lacks CD4 on its surface (Mirzabekov et al. (1999) *J Biol Chem* 274:28745-28750). The S736-68 and S736-75 envelopes, but not isogenic envelopes lacking the I309T mutation, supported CD4-independent virus fusion and entry, and this was abolished by treatment with 17b and other HIV-1 CD4i antibodies (data not shown). We next tested the S736-68 envelope clone, along with a site-directed mutant that restored the more common isoleucine at position 309 (S736-68m/TI), for their susceptibility to sCD4, to an anti-CD4 monoclonal antibody, to the CD4i monoclonal 17b, and to autologous SUMA plasma in JC53BL-13 cells (FIG. 5). The S736-68 pseudotyped virus was far more sensitive compared with the isogenic S736-

68m/TI mutant to neutralization by sCD4, 17b, and autologous plasma, and it was less sensitive to inhibition by anti-CD4 antibody. Similar findings were made with S736-75. These data suggest that the S736-68 and S736-75 envelopes, like those from some T-cell line adapted viruses, have a spontaneously exposed chemokine co-receptor binding site and is less dependent on CD4 binding for entry compared with most primary viruses. Thus, exposure of the co-receptor binding surface on primary HIV-1 viral envelopes occurs spontaneously in vivo, but such viruses are exquisitely sensitive to neutralization by antibodies including those targeting CD4-induced epitopes.

Discussion

Although much is already known about the structure, function, and antigenic properties of the HIV-1 envelope glycoprotein (Parren et al. (1999) *Aids* 13 Suppl A:S137-162; Kwong et al. (1998) *Nature* 393:648-659; Wyatt et al. (1998) *Nature* 393:705-711; Wyatt et al. (1998) *Science* 280:1884-1888; Kwong et al. (2002) *Nature* 420:678-682; Labrijn et al. (2003) *J Virol* 77:10557-10565; Burton et al. (2004) *Nat Immunol* 5:233-236; Zolla-Pazner et al (2004) *Nat Rev Immunol* 4:199-210; Broliden et al. (1992) *Proc Natl Acad Sci USA* 89:461-465; Scala et al. (1999) *J Immunol* 162:6155-6161; Opalka et al. (2004) *J Immunol Methods* 287:49-65; Sattentau et al. (1993) *J Virol* 67:7383-7393; Wu et al. (1996) *Nature* 384:179-183; Trkola et al. (1996) *Nature* 384:184-187; Salzwedel et al. (2000) *J Virol* 74:326-333; Rizzuto et al. (1998) *Science* 280:1949-1953; Rizzuto (2000) *AIDS Res Hum Retroviruses* 16:741-749; Xiang et al. (2002) *AIDS Res Hum Retroviruses* 18:1207-1217; Xiang et al. (2003) *Virology* 315:124-134; Huang et al. (2004) *Proc Natl Acad Sci USA* 101:2706-2711), the present study provides new insight into the immunogenicity and antigenic conservation of the envelope co-receptor binding site in natural human infection and the likely biological role of CD4i antibodies elicited against it. Previous studies, based largely on the identification and characterization of HIV-1 specific human monoclonal antibodies, suggested that the conformationally-dependent co-receptor binding surface on HIV-1 was only weakly immunogenic and CD41 antibodies relatively uncommon (Xiang et al. (2002) *AIDS Res Hum Retroviruses* 18:1207-1217; Xiang et al (2003) *Virology* 315:124-134; Huang et al. (2004) *Proc Natl Acad Sci USA* 101:2706-2711). However, the recent identification of increasing numbers of CD4i monoclonal antibodies from patients with acute and early HIV-1 infection (J.E.R., unpublished), together with findings described in this report, indicate quite the opposite to be the case. We find the vast majority (94%) of HIV-1 infected patients, infected by any one of ten different clades or CRFs, harbor HIV-specific CD4i Nabs with $IC_{50}$ titers ranging from 1:20 to greater than 1:100,000. The mean CD4i Nab titer against HIV-$2_{7312/V434M}$ among 189 subjects was 1:250 and the median titer 1:2,500. 114 subjects had Nab titers equal to or greater than 1:1,000, the highest reaching 1:143,000. Of interest, patients with subtype D and CRF11 infection had statistically higher titers of CD4i Nabs than did other individuals (p<0.0001). In a related study, we found that 8 of 10 healthy, uninfected human volunteers who were immunized with ALVAC vCP1452 HIV-1 gp140 alone or in combination with soluble monomeric HIV-1 gp120 (AIDSVAX B/B), developed HIV-1 CD41i neutralizing antibodies against HIV-$2_{7312A}$, compared with none of 5 control subjects who were vaccinated with placebo (J.M.D. and G.M.S., manuscript in preparation). To explain the elicitation of CD4i Nabs by soluble HIV-1 gp120 or expressed gp140, we suspect that envelope glycoprotein is bound to cell-surface-associated CD4, undergoes conformational change, and elicits a CD4i antibody response. Regardless of the mechanism, it is clear from our studies that the co-receptor binding site of the HIV-1 glycoprotein presented either in the context of natural infection or by vaccination with expressed or soluble glycoprotein, is inherently immunogenic and neutralization of sCD4-triggered HIV-2 is a sensitive and specific means for detecting these CD4-induced antibodies.

The observation that CD4i antibodies elicited by HIV-1 infection potently neutralized multiple strains of HIV-2 came as a surprise. While most primary human and simian lentiviruses use CCR5 as a co-receptor for cell attachment and entry (Zhang et al. (2000) *J Virol* 74:6893-6910), functionally important amino acids in the HIV-1 envelope co-receptor binding region identified by mutagenesis experiments (Rizzuto et al. (1998) *Science* 280:1949-1953; Rizzuto (2000) *AIDS Res Hum Retroviruses* 16:741-749; Kwong et al (1998) *Nature* 393:648-659) are only partially conserved in HIV-2, SIVmac and SIVagm (see FIG. 4). Moreover, conserved receptor binding would not necessarily be expected to be reflected in conserved receptor antigenicity, since there are numerous examples in other virus systems (Colman et al. (1997) *Structure* 5:591-593; Hewat (2001) *Curr Top Microbiol Immunol* 260:29-44; Bizebard et al. (2001) *Curr Top Microbiol Immunol* 260:55-64) where even a single amino acid substitution in a virus receptor binding region effectively abolishes antibody-antigen interaction while retaining receptor engagement functions. Thus, the finding that HIV-1 CD4i monoclonal antibodies such as 19e and 21c could bind viral glycoproteins as divergent as those from HIV-1, HIV-2, SIVmac, and SIVnme in a CD4-dependent fashion (FIG. 3a,b), and that monoclonal and polyclonal antibodies from HIV-1 infected humans routinely neutralized sCD4-triggered HIV-2 (Tables 2 and 3), was quite unexpected. We even found in preliminary studies extending beyond the phylogeny of HIV-1 and HIV-2 lineages that sCD4-treated SIVverTyo1 from African green monkey (FIG. 4) is susceptible to CD4i neutralization by some HIV-1 infected patient samples in titers as high as 1:1,400 (unpublished). In related studies, Berger and colleagues (Salzwedel et al. (2000) *J Virol* 74:326-333) have shown that the chemokine co-receptor binding surface of HIV-1 subtypes A, B, C, D, F and E (CRF01) is recognized by the HIV-1 CD4i monoclonal antibody 17b. Together, these observations highlight an extraordinary degree of antigenic conservation linked to co-receptor binding, and at the same time, an ability of the human humoral immune system to recognize and exploit these constraints.

It is of interest to consider the cooperative interactions that may be occurring among sCD4, the HIV-2 envelope glycoprotein, and CD4i antibody that result in potent virus neutralization. We have ruled out the possibility that HIV-1 elicited CD4i antibodies neutralize HIV-2 by binding directly to CD4, since a scorpion toxin-based CD4 mimetic that differs substantially in amino acid sequence from CD4 also results in conformational changes in HIV-2 gp120 leading to binding and neutralization by different monoclonal and polyclonal CD4i antibodies (J.M.D., P.D.K., J.A.R., G.M.S., unpublished). Moreover, the contact residues of several of the HIV-1 CD4i monoclonal antibodies that cross-neutralize HIV-2 have been resolved within antibody: HIV-1 gp120: sCD4 complexes, and they do not include contact points on CD4 (Kwong et al. (1998) *Nature* 393:648-659; Rizzuto (2000) *AIDS Res Hum Retroviruses* 16:741-749; Xiang et al. (2002) *AIDS Res Hum Retroviruses* 18:1207-1217; Darbha et al. (2004) *Biochemistry* 43:1410-1417). If sCD4 does not interact directly with CD4i antibodies in the context of the envelope trimer, then it must enhance the susceptibility of virus to neutralization by inducing conformational change and exposure of CD4i epitopes, but in a cooperative manner, since the magnitude of HIV-2 neutralization we observe is far greater than would be expected on the basis of additive stoichiometry. For example, in the CD4i Nab assay, we routinely use a concentration of sCD4 equal to its $IC_{50}$ for each virus (e.g., 9 nM for HIV-27312, 3 nM for HIV-$2_{UC-1}$, and 25 nM for HIV-$2_{ST/SXB1}$). This concentration of sCD4, by definition, reduces the number of infectious units (i.u.) measured by 50%, for example from 10,000 i.u. to 5,000 i.u., which corresponds to 100% infectivity (see FIG. 1, y-axis). The addition of HIV-1 CD4i monoclonal or polyclonal antibodies to HIV-2 in the absence of sCD4 results in little or no reduction in infectivity. But the addition of HIV-1 CD4i antibody together with sCD4 and results in as much as a 99.9% reduction in HIV-2 infectivity (10,000 i.u. reduced to background levels of <10 i.u.), far more than could be explained by a simple additive effect. An example of this cooperative effect is shown in FIG. 1c where a 1:1,000 dilution of each of three HIV-1 plasma specimens or a 0.5 ugm/ml concentration of 19e or 17b monoclonal antibody, in the presence of sCD4, leads to complete neutralization of HIV-$2_{7312A/V434M}$. Of note, Berger and colleagues (Salzwedel et al. (2000) *Proc Natl Acad Sci USA* 97:12794-12799) have demonstrated cooperative interactions between different gp120 protomers within a trimer complex of HIV-1 by complementing defects in CD4 and co-receptor binding and membrane fusion. These investigators observed that binding of CD4 to one gp120 protomer could induce conformational change not only within that protomer but also in a neighboring gp120 protomer, in each instance leading to exposure of the co-receptor binding site, chemokine receptor binding, and fusion. An analogous type of cooperative interaction may explain our findings, wherein sCD4 binds (perhaps transiently) to one protomer within the HIV-2 gp120 trimer complex, which in turn leads to enhanced CD4i antibody binding to the same or adjacent protomers, and ultimately virus neutralization.

The role that CD4i antibodies play in natural HIV-1 infection is becoming more clear. Our data, together with other results (Kolchinsky et al. (2001) *J Virol* 75:2041-2050; Zhang et al. (2002) *J Virol* 76:644-655), indicate that spontaneously-occurring HIV-1 variants that exhibit an exposed co-receptor binding surface and CD4 independence, are generated in vivo where they are almost certainly targeted for neutralization by CD4i or other HIV-1 specific antibodies. In fact, four studies have now shown that single amino acid substitutions in the HIV-1 glycoprotein, either at the base of V1/V2 (Kolchinsky et al. (2001) *J Virol* 75:3435-3443; Wei et al. (2003) *Nature* 422:307-312) or in the V3 loop (Zhang et al. (2002) *J Virol* 76:644-655 and this report), are sufficient to confer on the virus varying degrees of CD4 independence, greater spontaneous exposure of the co-receptor binding site, and enhanced susceptibility to CD4i Nabs. Principles of viral dynamics, coupled with the well documented error-prone nature of HIV-1 reverse transcriptase, indicate that such mutations must be occurring in vivo on a virtually continuous basis, as has been documented for comparable mutations leading to anti-retroviral drug resistance (Wei et al. (1995) *Nature* 373:117-122). Thus, CD4i antibodies may influence HIV-1 natural history and pathogenesis to a greater extent than is currently recognized by limiting the spectrum of cells available as targets of virus infection to those expressing surface CD4. In this context, three observations are of note: First, Gabuzda and colleagues have reported that HIV-1 virus within the central nervous system sanctuary (where circulating antibodies are relatively excluded) has less dependence on cell surface bound CD4 for its attachment and entry and such viruses may target CD4-negative astrocytes as well as $CD4^{lo}$ microglial cells for infection (Gorry et al. (2002) *J Virol* 76:6277-6292). Secondly, the three HIV-2 virus strains that we found to be susceptible to HIV-1 CD4i antibody neutralization (7312A, UC-1, ST/SXB1) all utilize CCR5 as a co-receptor, whereas three other HIV-2 strains (UC-2, ROD-B, $MVP_{15132}$) that we examined utilize X4 for cell entry and were not susceptible to HIV-1 CD4i antibody neutralization. Interestingly, monomeric envelope glycoprotein from one of these X4 tropic viruses, $MVP_{15132}$, bound HIV-1 CD4i monoclonal and polyclonal antibodies in a CD4-induced manner just as efficiently as did 7312A (FIGS. 2 and 3b). In this case it would seem that tertiary or quaternary interactions within the virion-associated envelope trimer spike prevent access of CD4i antibodies to the HIV-2 X4 co-receptor binding site even after sCD4 binding. If this were also true for HIV-1, it is conceivable that CD4i antibodies could play a role in selection for X4 viruses that is observed in natural human infection (Moore et al (2004) *AIDS Res Hum Retroviruses* 20:111-126). Thirdly, it has been reported that subtype C HIV-1 virus that is associated with heterosexual transmission between couples in Zambia exhibits an envelope glycoprotein with shorter variable loops, fewer glycans, and greater neutralization sensitivity than is typical of chronic HIV-1 strains (Derdeyn et al. (2004) *Science* 303:2019-2022); it is possible that these same features would make such viruses more susceptible to CD4i Nabs and this is an important area for future study.

The discovery that sCD4-triggered HIV-2 is susceptible to binding and neutralization by HIV-1 elicited CD4i antibodies has practical application in studies of HIV-1 natural history and vaccine assessment. A number of investigative groups have attempted to stabilize the HIV-1 envelope glycoprotein in a CD4-bound configuration in order to use it as an immunogen designed to elicit antibodies against viral receptor surfaces or other intermediate envelope structures (Xiang et al. (2002) *J Virol* 76:9888-9899; Liao et al. (2004) *J Virol* 78:5270-5278; Fouts et al. (2000) *J Virol* 74:11427-11436). But methods to selectively identify and titer Nabs specific for such epitopes have been limited. Here, we show that neutralization of sCD4 treated HIV-2 represents an extremely sensitive and specific assay to detect HIV-1 elicited CD4i antibodies. Investigators have also targeted the membrane-proximal external region (MPER) of HIV-1 gp41 for vaccine development, since conserved epitopes in this region are capable of eliciting broadly reactive Nabs in natural infection (Purtscher et al. (1994) *AIDS Res Hum Retroviruses* 10:1651-1658; Buchacher et al. (1994) *AIDS Res Hum Retroviruses* 10:359-369; Zwick et al. (2001) *J Virol* 75:10892-10905; Ho et al. (2002) *Vaccine* 20:1169-1180; Liang et al. (1999) *Vaccine* 17:2862-2872; McGaughey et al. (2003) *Biochemistry* 42:3214-3223; Tian et al. (2002) *J Pept Res* 59:264-276; Barnett et al. (2001) *J Virol* 75:5526-5540; Mascola et al. (1996) *J Infect Dis* 173:340-348; Binley et al. (2004) *J Virol* 78:13232-13252; Ofek et al. (2004) *J Virol* 78:10724-10737). But again, neutralization assays are lacking that allow for the sensitive and specific detection of MPER epitope-specific Nabs (Opalka et al. (2004) *J Immunol Methods* 287:49-65). We thus considered the possibility that HIV-2 could act more generally as a "molecular scaffold" on which to present these and other HIV-1 epitope-specific antigens in the context of a functional envelope glycoprotein that does not otherwise cross-react with HIV-1 neutralizing antibodies. In recent studies, we have identified and modified by site-directed mutagenesis HIV-2 strains that can be used to detect and quantify binding and neutralization by the HIV-1 gp41 MPER-elicited human monoclonal antibody 4E10 with high sensitivity and specificity (F.B.R., J.M.D. and G.M.S., unpublished data). Thus, the strategy described in this report of using HIV-2 envelope glycoproteins in the context of infectious virions or as isolated proteins to detect HIV-1 epitope-specific antibodies may find wider application in the assessment of candidate vaccines and in studies of HIV-1 natural history.

Example 2

With many HIV-1 vaccine candidates currently in the research pipeline, methods are needed for detecting and quantifying epitope-specific neutralizing antibody (Nab) responses in naturally-infected individuals and vaccinated subjects. HIV-1 and HIV-2 share less than 50% sequence similarity in envelope and they generally exhibit little cross-neutralization. We postulated that HIV-1 Nab epitopes could be identified in, or molecularly engineered into, functional HIV-2 env glycoproteins.

Sequence alignments of HIV-1 and HIV-2 viruses were examined to identify conserved regions in the membrane proximal external region (MPER) of gp41 and site-directed mutagenesis was used to change selected amino acids in this region of HIV-2 to resemble HIV-1. HIV-2 virions bearing envelopes with 4E10 core epitope amino acids, or control viruses containing wild-type HIV-1 or HIV-2 env, were analyzed for neutralization susceptibility to a panel of HIV-1 and HIV-2 monoclonal antibodies (Mab) or HIV-1 infected patient plasma using a JC53b1-13 HIV entry assay previously described (Nature 422:307, 2003).

Figure 9:
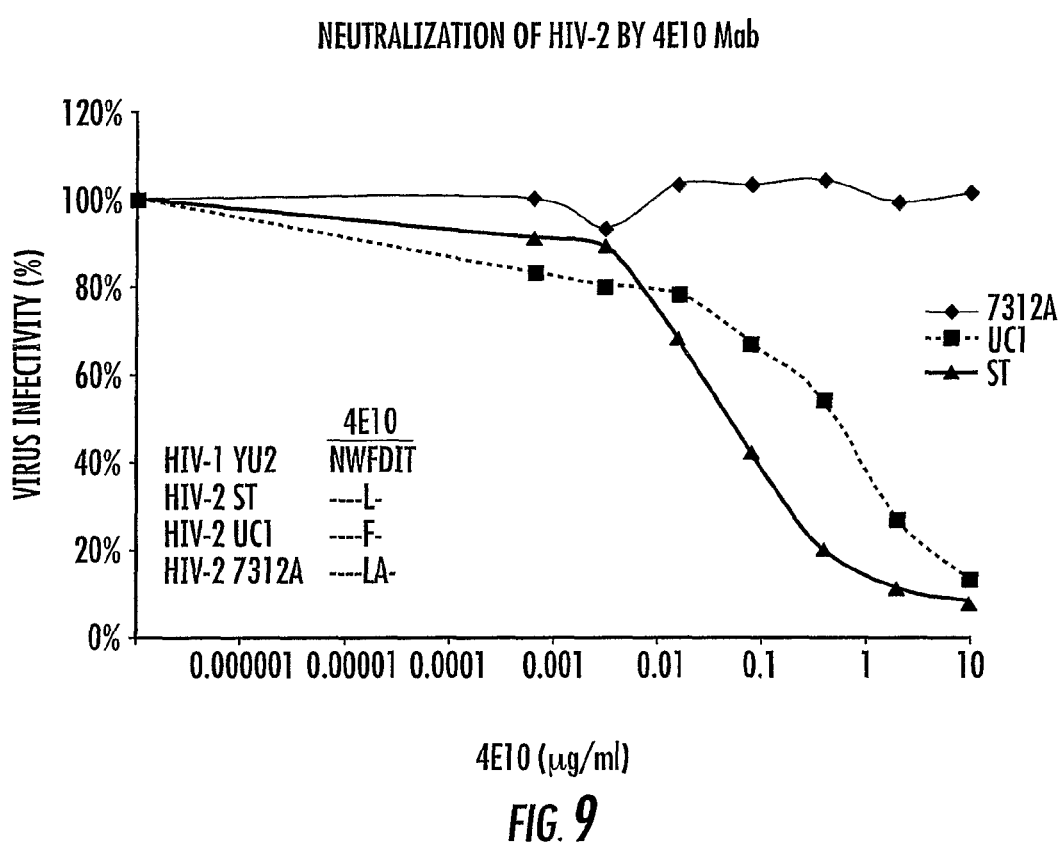
FIG. 9 shows the neutralization of HIV-1 by 4E10 monoclonal antibodies. These data show that certain naturally-occurring or genetically-modified strains of HIV-2 can be used to detect HIV neutralization by 4E10 and 4E10-like antibodies.
Figure 10:
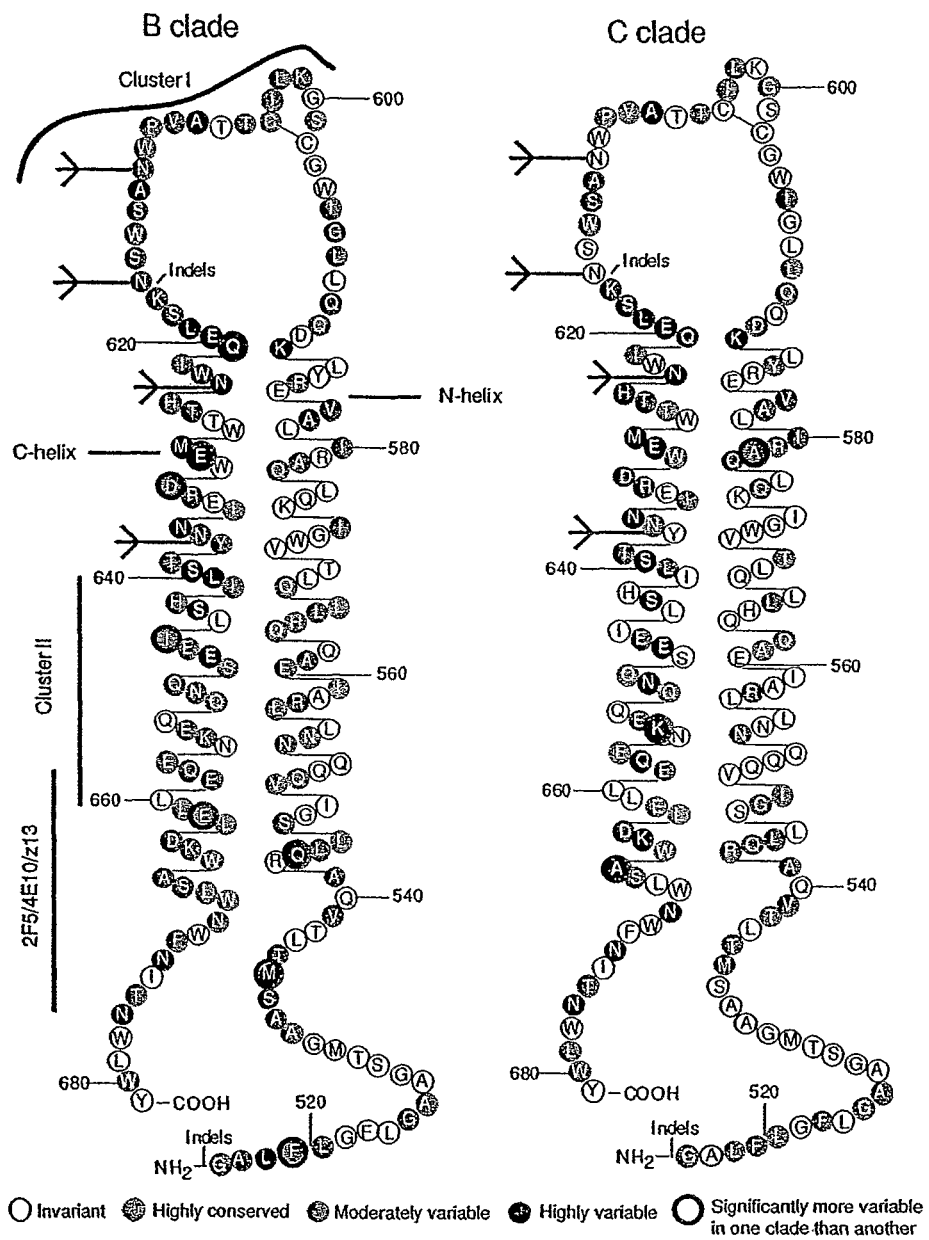
FIG. 10 provides a 2-D schematic of HXB2 gp41e from HIV *Molecular Immunology* (2002) Bette et al. eds., Los Alamos National Laboratory, Theoretical Biology and Biophysics, Los Alamos, N. Mex. LA-UR 03-5816. The figure illustrates the position of the 2F5/4E10/Z13 epitope cluster, epitope cluster II, the C-helix, N-helix, and epitope cluster I.

The neutralization of HIV-2 by 4E10 and 2F5 monoclonal antibody was demonstrated. HIV-2 viruses 7312A, UC1, and ST were pre-incubated for 1 hour at 37° C. with the indicated concentrations of 4E10 and 2F5 monoclonal antibody. They were then plated on JC53b1-13 cells and infectivity determined after 48 hrs, as described in Decker et al (submitted and incorporated into this patent application). Site-directed mutations in the HIV-2 7312A envelope at positions 675 (L to I) and 676 (A to T) making the sequence of the 4E10 epitope identical to that of HIV-1 YU2 (see inset of FIG. 9) rendered the virus susceptible to 4E10; conversely, altering these same two amino acids in the 4E10 sensitive HIV-2 ST virus to alanine residues rendered this virus resistant to 4E10 (data not shown).

More specifically, virus bearing a prototypic HIV-1 env glycoprotein (YU2) was intermediately sensitive to neutralization by 4E10 (IC50=25 ug/ml), 2F5 (IC50=25 ug/ml), and b12 (IC50=3 ug/ml). Virus containing the envelope of HIV-2 strain 7312A was resistant to neutralization by all three Mabs (IC50>50 ug/ml). Site-directed substitution of aa 675 (L to I) and aa 676 (A to T) in the 7312A MPER (HXB numbering) rendered the virus remarkably sensitive to neutralization by 4E10 (IC50=0.8 ug/ml) (See, FIG. 9) but not by 2F5 or b12. Conversely, altering these same two amino acids in the 4E10 sensitive HIV-2 ST virus to alanine residues rendered this virus resistant to 4E10 (data not shown). Two naturally-occurring strains of HIV-2 (ST and UC1) were found to be extremely sensitive to neutralization by 4E10 (IC50=0.1 and 1.2 ug/ml, respectively) but were resistant to 2F5 and b12. Twenty-four HIV-1 clade B patient plasmas were examined for 4E10-like Nabs; six showed evidence of neutralization with reciprocal IC50 titers between 0.028 and 0.001 (data not shown).

In a similar fashion, site-directed mutations in the HIV-2 7312A envelope at positions 660 (K to A), 662 (N to D), 663 (S to K), and 665 (D to A), which together make the HIV-2 sequence identical to that of the 2F5 epitope region of HIV-1 YU2, rendered the modified HIV-2 virus susceptible to 2F5 with an IC50 of <0.1 ug/ml; conversely, the wild-type HIV-2 7312A envelope-containing viruses were completely resistant to 2F5 (IC50>50.0 ug/ml) (data not shown). These data show that certain naturally-occurring or genetically-modified strains of HIV-2 can be used to detect HIV neutralization by 4E10 and 4E10-like antibodies and by 2F5 and 2F5-like antibodies.

Conclusions: Naturally occurring or genetically engineered variants of HIV-2 env glycoprotein can be used to detect and quantify HIV-1 elicited 4E10-like and 2F5 Nabs with great sensitivity (IC50=0.1 ug/ml) and specificity. We have evidence that an analogous approach is feasible for detecting HIV-1 elicited Nabs against other MPER epitopes as well as epitopes on gp120. Epitope-specific assays of HIV-1 Nab responses may play an important role in HIV vaccine development and clinical assessment.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for detecting an HIV-1 binding antibody in a subject infected with HIV-1, said method comprising:

a) providing a chimeric envelope polypeptide, wherein said chimeric envelope polypeptide comprises:

i): an amino acid sequence of an HIV-2 envelope polypeptide, a functional variant of the HIV-2 envelope polypeptide, a Simian Immunodeficiency virus (SIV) envelope polypeptide, or a functional variant of the SIV envelope polypeptide; and ii) a heterologous epitope selected from the group consisting of:

1) a heterologous epitope comprising the amino acid sequence set forth in SEQ ID NO:38, or a functional variant thereof, wherein the amino acid sequence of said functional variant differs from SEQ ID NO:38 by up to three amino acids;

2) a heterologous epitope comprising the amino acid sequence set forth in SEQ ID NO:15, or an immunologically equivalent epitope thereof, wherein the amino acid sequence of said immunologically equivalent epitope differs from SEQ ID NO:15 by one amino acid; and 3) a heterologous epitope comprising the amino acid sequence set forth in SEQ ID NO:16, or an immunologically equivalent epitope thereof, wherein the amino acid sequence of said immunologically equivalent epitope differs from SEQ ID NO:16 by up to two amino acids;

wherein said heterologous epitope is recognized by an HIV-1 binding antibody, and wherein said heterologous epitope is located at a position within the amino acid sequence of said HIV-2 envelope polypeptide, said functional variant of said HIV-2 envelope polypeptide, said Simian Immunodeficiency virus (SIV) envelope polypeptide, or said functional variant of said SIV envelope polypeptide;

b) contacting said envelope polypeptide with an amount of bodily fluid from said subject; and, c) detecting said HIV-1 binding antibody, wherein said method is capable of detecting the binding antibody present in said bodily fluid when present at a concentration of less than 0.1 μg/ml.

2. The method of claim 1, wherein said HIV-1 binding antibody is a neutralizing HIV-1 antibody.

3. The method of claim 1, wherein said chimeric envelope polypeptide is incorporated into an HIV-2 or SIV retrovirus.

4. The method of claim 3, wherein said retrovirus comprises an HIV-2, an SIV, or a pseudotyped primate lentivirus.

5. The method of claim 4, wherein said HIV-2 comprises the HIV-2 isolate 7312A or ST or a molecular clone derived therefrom.

6. The method of claim 3, wherein detecting said HIV-1 binding antibody in said bodily fluid comprises determining the infectivity of the HIV-1 or SIV retrovirus comprising said chimeric envelope polypeptide in the presence of said HIV-1 binding antibody.

7. The method of claim 1, wherein detecting said HIV-1 binding antibody comprises a competition binding assay.

8. The method of claim 1, wherein said envelope polypeptide comprises an amino acid sequence having at least 95% sequence identity to the sequence set forth in SEQ ID NO:2, 3, 4, or 5.

9. The method of claim 1, wherein the titer of the HIV-1 binding antibody is determined.

10. The method of claim 1, wherein the HIV-1 binding antibody is isolated and characterized.

11. The method of claim 1, wherein said heterologous epitope comprises the amino acid sequence set forth in SEQ ID NO:38.

12. The method of claim 1, wherein said heterologous epitope comprises the amino acid sequence set forth in SEQ ID NO:15.

13. The method of claim 1, wherein said heterologous epitope comprises the amino acid sequence set forth in SEQ ID NO:16.

* * * * *